(12) United States Patent
Wahl et al.

(10) Patent No.: US 11,918,292 B2
(45) Date of Patent: Mar. 5, 2024

(54) ORTHOPEDIC FIXATION CONTROL AND MANIPULATION

(71) Applicant: DePuy Synthes Products, Inc., Raynham, MA (US)

(72) Inventors: Michael Wahl, Wilmington, DE (US); Bernd Gutmann, Hassloch (DE); Kevin Clancy, West Chester, PA (US); Dana Heavey, Coatesville, PA (US); Tina Corey, Wallingford, PA (US); Todd Kent, Cherry Hill, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 177 days.

(21) Appl. No.: 17/078,629

(22) Filed: Oct. 23, 2020

(65) Prior Publication Data
US 2021/0077194 A1 Mar. 18, 2021

Related U.S. Application Data

(62) Division of application No. 15/247,333, filed on Aug. 25, 2016, now Pat. No. 10,835,318.

(51) Int. Cl.
*A61B 17/66* (2006.01)
*A61B 17/62* (2006.01)
(Continued)

(52) U.S. Cl.
CPC .............. *A61B 34/10* (2016.02); *A61B 34/25* (2016.02); *G06F 3/04847* (2013.01); *G06T 7/70* (2017.01);
(Continued)

(58) Field of Classification Search
CPC ... A61B 34/10; A61B 34/25; A61B 2034/104; A61B 2034/105; A61B 2034/107;
(Continued)

(56) References Cited

U.S. PATENT DOCUMENTS

| | | |
|---|---|---|
| 2,055,024 A | 9/1936 | Bittner, Jr. |
| 2,391,537 A | 12/1945 | Anderson |

(Continued)

FOREIGN PATENT DOCUMENTS

| | | |
|---|---|---|
| CN | 1494397 | 5/2004 |
| CN | 101296664 A | 10/2008 |

(Continued)

OTHER PUBLICATIONS

Changjiang Yang et al: "Planar conic based camera calibration", Proceedings / 15th International Conference on Pattern Recognition Barcelona, Spain, Sep. 3-7, [Proceedings of the International Conference on Pattern Recognition. (ICPR)], IEEE Computer Society, Los Alamitos, Calif. [U.A.], vol. 1, Sep. 3, 2000 (Sep. 3, 2000) pp. 555-558.

(Continued)

*Primary Examiner* — Nicholas J Plionis
(74) *Attorney, Agent, or Firm* — BakerHostetler

(57) ABSTRACT

A fixation apparatus may be attached to first and second anatomical structure segments. Images of the fixation apparatus and the attached anatomical structure segments may then be captured. In some examples, the images need not necessarily be orthogonal with respect to one another. Configuration information associated with the fixation apparatus may then be received. Additionally, first image information may be received, for example including indications of one or more locations, within the images, of at least part of one or more elements of the fixation apparatus. Additionally, second image information may be received, for example including indications of one or more locations, within the images, of at least part of the first and the second anatomical structure segments. Manipulations to the fixation apparatus for correction of the anatomical structure deformity may (Continued)

then be determined, and indications of the determined manipulations may then be provided to one or more users.

20 Claims, 38 Drawing Sheets
(33 of 38 Drawing Sheet(s) Filed in Color)

(51) Int. Cl.
  *A61B 34/00* (2016.01)
  *A61B 34/10* (2016.01)
  *G06F 3/04847* (2022.01)
  *G06T 7/70* (2017.01)
  *A61B 90/00* (2016.01)
(52) U.S. Cl.
  CPC .............. *A61B 17/62* (2013.01); *A61B 17/66* (2013.01); *A61B 2034/104* (2016.02); *A61B 2034/105* (2016.02); *A61B 2034/107* (2016.02); *A61B 2034/252* (2016.02); *A61B 2034/254* (2016.02); *A61B 2090/367* (2016.02); *A61B 2090/3966* (2016.02); *G06T 2207/10004* (2013.01); *G06T 2207/30008* (2013.01)
(58) Field of Classification Search
  CPC ...... A61B 2034/252; A61B 2090/3966; A61B 17/62; A61B 17/66
  See application file for complete search history.

(56) References Cited

U.S. PATENT DOCUMENTS

| | | |
|---|---|---|
| 3,977,397 A | 8/1976 | Kalnberz et al. |
| 4,081,686 A | 3/1978 | Nieuweboer |
| 4,450,834 A | 5/1984 | Fischer |
| 4,489,111 A | 12/1984 | Woodrum |
| 4,615,338 A | 10/1986 | Ilizarov et al. |
| 4,620,533 A | 11/1986 | Mears |
| 4,630,203 A | 12/1986 | Szirtes |
| 4,768,524 A | 9/1988 | Hardy |
| 4,784,125 A | 11/1988 | Monticelli et al. |
| 4,875,165 A | 10/1989 | Fencil et al. |
| 4,889,111 A | 12/1989 | Ben-Dov |
| 4,890,631 A | 1/1990 | Hardy |
| 4,930,961 A | 6/1990 | Weis |
| 4,964,320 A | 10/1990 | Lee, Jr. |
| 4,973,331 A | 11/1990 | Pursley et al. |
| 5,062,844 A | 11/1991 | Jamison et al. |
| 5,074,866 A | 12/1991 | Sherman et al. |
| 5,087,258 A | 2/1992 | Schewior |
| 5,095,919 A | 3/1992 | Monticelli et al. |
| 5,108,393 A | 4/1992 | Ruffa |
| 5,156,605 A | 10/1992 | Pursley et al. |
| 5,179,525 A | 1/1993 | Griffis et al. |
| 5,180,380 A | 1/1993 | Pursley et al. |
| 5,209,750 A | 5/1993 | Stef |
| 5,275,598 A | 1/1994 | Cook |
| 5,358,504 A | 10/1994 | Paley et al. |
| 5,437,668 A | 8/1995 | Aronson et al. |
| 5,443,464 A | 8/1995 | Russell et al. |
| 5,451,225 A | 9/1995 | Ross et al. |
| 5,458,599 A | 10/1995 | Adobbati |
| 5,540,686 A | 7/1996 | Zippel et al. |
| 5,601,551 A | 2/1997 | Taylor et al. |
| 5,630,814 A | 5/1997 | Ross et al. |
| 5,653,707 A | 8/1997 | Taylor et al. |
| 5,681,309 A | 10/1997 | Ross et al. |
| 5,702,389 A | 12/1997 | Taylor et al. |
| 5,728,095 A | 3/1998 | Taylor et al. |
| 5,746,741 A | 5/1998 | Kraus et al. |
| 5,766,173 A | 6/1998 | Ross et al. |
| 5,776,132 A | 7/1998 | Blyakher |
| 5,871,018 A | 2/1999 | Delp et al. |
| 5,885,282 A | 3/1999 | Szabo |
| 5,891,143 A | 4/1999 | Taylor et al. |
| 5,919,192 A | 7/1999 | Shouts |
| 5,951,556 A | 9/1999 | Faccioli et al. |
| 5,961,515 A | 10/1999 | Taylor et al. |
| 5,963,612 A | 10/1999 | Navab |
| 5,967,777 A | 10/1999 | Klein et al. |
| 5,968,043 A | 10/1999 | Ross et al. |
| 5,971,984 A | 10/1999 | Taylor et al. |
| 5,976,142 A | 11/1999 | Chin |
| 6,017,341 A | 1/2000 | Windhagen et al. |
| 6,021,579 A | 2/2000 | Schimmels et al. |
| 6,030,386 A | 2/2000 | Taylor et al. |
| 6,047,080 A | 4/2000 | Chen et al. |
| 6,129,727 A | 10/2000 | Austin et al. |
| 6,206,566 B1 | 3/2001 | Schuetz |
| 6,293,947 B1 | 9/2001 | Buchbinder |
| 6,320,928 B1 | 11/2001 | Vaillant et al. |
| 6,363,169 B1 | 3/2002 | Ritter et al. |
| 6,434,278 B1 | 8/2002 | Hashimoto |
| 6,501,848 B1 | 12/2002 | Carroll et al. |
| 6,510,241 B1 | 1/2003 | Vaillant et al. |
| 6,537,275 B2 | 3/2003 | Venturini et al. |
| 6,701,174 B1 | 3/2004 | Krause et al. |
| 6,711,432 B1 | 3/2004 | Krause et al. |
| 6,912,293 B1 | 6/2005 | Korobkin |
| 7,113,623 B2 | 9/2006 | Chen et al. |
| 7,187,792 B2 | 3/2007 | Fu et al. |
| 7,226,449 B2 | 6/2007 | Venturini et al. |
| 7,280,687 B2 | 10/2007 | Ban et al. |
| 7,306,601 B2 | 12/2007 | McGrath et al. |
| 7,388,972 B2 | 6/2008 | Kitson |
| 7,490,085 B2 | 2/2009 | Walker et al. |
| RE40,914 E | 9/2009 | Taylor et al. |
| 7,645,279 B1 | 1/2010 | Haupt |
| 7,657,079 B2 | 2/2010 | Lake et al. |
| 7,677,078 B2 | 3/2010 | Sauer et al. |
| 7,758,582 B2 | 7/2010 | Ferrante et al. |
| 7,828,801 B2 | 11/2010 | Mirza et al. |
| 7,837,621 B2 | 11/2010 | Krause et al. |
| 7,887,537 B2 | 2/2011 | Ferrante et al. |
| 7,955,334 B2 | 6/2011 | Steiner et al. |
| 8,029,505 B2 | 10/2011 | Hearn et al. |
| 8,057,474 B2 | 11/2011 | Knuchel et al. |
| 8,062,293 B2 | 11/2011 | Steiner et al. |
| 8,147,491 B2 | 4/2012 | Lavi |
| 8,157,800 B2 | 4/2012 | Vvedensky et al. |
| 8,202,273 B2 | 6/2012 | Karidis |
| 8,257,353 B2 | 9/2012 | Wong |
| 8,282,652 B2 | 10/2012 | Mackenzi et al. |
| 8,296,094 B2 | 10/2012 | Harrison et al. |
| 8,323,282 B2 | 12/2012 | Taylor |
| 8,333,766 B2 | 12/2012 | Edelhauser et al. |
| 8,377,060 B2 | 2/2013 | Vasta et al. |
| 8,419,732 B2 | 4/2013 | Mullaney |
| 8,425,512 B2 | 4/2013 | Vasta et al. |
| 8,430,878 B2 | 4/2013 | Vasta et al. |
| 8,439,914 B2 | 5/2013 | Ross et al. |
| 8,444,644 B2 | 5/2013 | Ross et al. |
| 8,454,604 B2 | 6/2013 | Wong |
| 8,469,958 B2 | 6/2013 | Stevens |
| 8,574,232 B1 | 11/2013 | Ross et al. |
| 8,654,150 B2 | 2/2014 | Haskell |
| 8,777,946 B2 | 7/2014 | Lindahl et al. |
| 8,834,467 B2 | 9/2014 | Singh et al. |
| 8,858,555 B2 | 10/2014 | Crozet et al. |
| 8,864,763 B2 | 10/2014 | Murray et al. |
| 8,906,021 B1 | 12/2014 | Lehmann et al. |
| 8,945,128 B2 | 2/2015 | Singh et al. |
| 8,951,252 B2 | 2/2015 | Steiner et al. |
| 8,952,986 B2 | 2/2015 | Haskell |
| 9,011,438 B2 | 4/2015 | Steiner et al. |
| 9,017,339 B2 | 4/2015 | Edelhauser et al. |
| 9,039,706 B2 | 5/2015 | Murray et al. |
| 9,044,271 B2 | 6/2015 | Edelhauser et al. |
| 9,066,756 B2 | 6/2015 | Wong |
| 9,078,700 B2 | 7/2015 | Ross et al. |
| 9,101,398 B2 | 8/2015 | Singh et al. |
| 9,155,559 B2 | 10/2015 | Ross et al. |

(56) References Cited

U.S. PATENT DOCUMENTS

| | | |
|---|---|---|
| 9,204,937 B2 | 12/2015 | Edelhauser et al. |
| 9,220,533 B2 | 12/2015 | Singh et al. |
| 9,642,649 B2 | 5/2017 | Nikonovas |
| 9,895,167 B2 | 2/2018 | Edelhauser et al. |
| 9,959,683 B2 | 5/2018 | Mikheev et al. |
| 10,932,713 B2 | 3/2021 | Lewis et al. |
| 2001/0018617 A1 | 8/2001 | Copf et al. |
| 2002/0010465 A1 | 1/2002 | Koo et al. |
| 2003/0106230 A1 | 6/2003 | Hennessey |
| 2003/0191466 A1 | 10/2003 | Austin et al. |
| 2004/0068187 A1 | 4/2004 | Krause et al. |
| 2004/0073211 A1 | 4/2004 | Austin et al. |
| 2004/0073212 A1 | 4/2004 | Kim |
| 2004/0082849 A1 | 4/2004 | Schweikard et al. |
| 2004/0111024 A1 | 6/2004 | Zheng et al. |
| 2004/0133199 A1 | 7/2004 | Coati et al. |
| 2004/0167518 A1 | 8/2004 | Mark |
| 2004/0208279 A1 | 10/2004 | Xiao et al. |
| 2005/0149018 A1 | 7/2005 | Cooper et al. |
| 2005/0215997 A1 | 9/2005 | Austin et al. |
| 2005/0256389 A1 | 11/2005 | Koga et al. |
| 2006/0276786 A1 | 12/2006 | Brinker |
| 2007/0043354 A1 | 2/2007 | Koo et al. |
| 2007/0043429 A1 | 2/2007 | Hegel et al. |
| 2007/0161983 A1 | 7/2007 | Cresina et al. |
| 2007/0161984 A1 | 7/2007 | Cresina et al. |
| 2007/0238069 A1 | 10/2007 | Lovald et al. |
| 2008/0012850 A1 | 1/2008 | Keating III |
| 2008/0114267 A1 | 5/2008 | Lloyd et al. |
| 2009/0036890 A1 | 2/2009 | Karidis |
| 2009/0036892 A1 | 2/2009 | Karidis et al. |
| 2009/0105621 A1 | 4/2009 | Boyd et al. |
| 2009/0143788 A1 | 6/2009 | Fang et al. |
| 2009/0161945 A1 | 6/2009 | Morgan-Mar et al. |
| 2009/0177198 A1 | 7/2009 | Theodoros et al. |
| 2009/0226055 A1 | 9/2009 | Dankowicz et al. |
| 2009/0275944 A1 | 11/2009 | Huebner et al. |
| 2009/0326532 A1 | 12/2009 | Schulze |
| 2009/0326560 A1 | 12/2009 | Lampropoulos et al. |
| 2010/0030219 A1 | 2/2010 | Lerner et al. |
| 2010/0039421 A1 | 2/2010 | Toyomura et al. |
| 2010/0087819 A1 | 4/2010 | Mullaney |
| 2010/0104150 A1 | 4/2010 | Saint et al. |
| 2010/0172567 A1 | 7/2010 | Prokoski |
| 2010/0179548 A1 | 7/2010 | Marin |
| 2010/0191239 A1 | 7/2010 | Sakkers et al. |
| 2010/0280516 A1 | 11/2010 | Taylor |
| 2010/0305568 A1 | 12/2010 | Ross et al. |
| 2011/0004199 A1 | 1/2011 | Ross et al. |
| 2011/0029093 A1 | 2/2011 | Bojarski et al. |
| 2011/0103676 A1 | 5/2011 | Mullaney |
| 2011/0313418 A1* | 12/2011 | Nikonovas ............ A61B 17/66 606/56 |
| 2011/0313419 A1 | 12/2011 | Mullaney |
| 2012/0029280 A1 | 2/2012 | Kucklick |
| 2012/0078251 A1 | 3/2012 | Benenati et al. |
| 2012/0136355 A1 | 5/2012 | Wolfson |
| 2012/0232554 A1 | 9/2012 | Shaevitz et al. |
| 2012/0259343 A1 | 10/2012 | Clark et al. |
| 2012/0330312 A1 | 12/2012 | Burgherr et al. |
| 2013/0041288 A1 | 2/2013 | Taylor et al. |
| 2013/0060146 A1 | 3/2013 | Yang et al. |
| 2013/0131675 A1 | 5/2013 | Vasta et al. |
| 2013/0138017 A1 | 5/2013 | Jundt et al. |
| 2013/0201212 A1* | 8/2013 | Haskell ................. A61B 34/10 345/632 |
| 2013/0211521 A1 | 8/2013 | Shenoy et al. |
| 2013/0245625 A1 | 9/2013 | Vasta et al. |
| 2013/0296857 A1 | 11/2013 | Barnett et al. |
| 2014/0135764 A1 | 5/2014 | Ross et al. |
| 2014/0236152 A1 | 8/2014 | Walberg et al. |
| 2014/0257286 A1 | 9/2014 | Lindahl et al. |
| 2014/0278325 A1 | 9/2014 | Burgherr et al. |
| 2014/0303670 A1 | 10/2014 | Colloca |
| 2014/0379038 A1 | 12/2014 | Dogramadzi et al. |
| 2015/0080892 A1 | 3/2015 | Lehmann et al. |
| 2015/0088135 A1 | 3/2015 | Singh |
| 2015/0112339 A1 | 4/2015 | Lindahl et al. |
| 2015/0223842 A1 | 8/2015 | Murray et al. |
| 2015/0238227 A1 | 8/2015 | Singh et al. |
| 2015/0257788 A1 | 9/2015 | Jay et al. |
| 2015/0265313 A1 | 9/2015 | Wong |
| 2015/0272624 A1 | 10/2015 | Singh |
| 2015/0305776 A1 | 10/2015 | Ross et al. |
| 2015/0305777 A1 | 10/2015 | Singh et al. |
| 2015/0313641 A1 | 11/2015 | Ross et al. |
| 2016/0022314 A1 | 1/2016 | Bordeaux et al. |
| 2016/0045225 A1 | 2/2016 | Edelhauser et al. |
| 2016/0092651 A1 | 3/2016 | Austin et al. |
| 2016/0113681 A1 | 4/2016 | Singh |
| 2016/0125603 A1 | 5/2016 | Tanji |
| 2016/0183979 A1 | 6/2016 | Del Deo et al. |
| 2017/0181800 A1 | 6/2017 | Nikonovas |
| 2017/0224520 A1 | 8/2017 | Karasahin |
| 2017/0303966 A1 | 10/2017 | Edelhauser et al. |
| 2017/0348054 A1 | 12/2017 | Kumar et al. |
| 2017/0348057 A1 | 12/2017 | Kumar et al. |
| 2017/0354439 A1 | 12/2017 | Mannanal et al. |
| 2018/0055569 A1 | 3/2018 | Wahl et al. |

FOREIGN PATENT DOCUMENTS

| | | |
|---|---|---|
| CN | 102883671 | 1/2013 |
| CN | 103270513 | 8/2013 |
| CN | 105852985 A | 8/2016 |
| EP | 1100048 A1 | 5/2001 |
| EP | 1690506 A1 | 8/2006 |
| EP | 2767252 A1 | 8/2014 |
| FR | 2576774 A1 | 8/1986 |
| FR | 2756025 A1 | 5/1998 |
| JP | 2001-523985 A | 11/2001 |
| JP | 2003-144454 A | 5/2003 |
| JP | 2003-530177 A | 10/2003 |
| JP | 2004-254899 A | 9/2004 |
| JP | 2006-507056 A | 3/2006 |
| JP | 2006-218298 A | 8/2006 |
| JP | 2009-505736 A | 2/2009 |
| JP | 2011-512883 A | 4/2011 |
| JP | 2013-526377 | 6/2013 |
| KR | 20-0443058 Y1 | 1/2009 |
| RU | 2159091 C2 | 11/2000 |
| RU | 2352283 C2 | 4/2009 |
| WO | 98/12975 A2 | 4/1998 |
| WO | 99/59100 A1 | 11/1999 |
| WO | 01/15611 A1 | 3/2001 |
| WO | 01/78015 A2 | 10/2001 |
| WO | 03/30759 A2 | 4/2003 |
| WO | 2007/024904 A2 | 3/2007 |
| WO | 2009/102904 A1 | 8/2009 |
| WO | 2010/002587 A1 | 1/2010 |
| WO | 2010/104567 A1 | 9/2010 |
| WO | 2011/026475 A1 | 3/2011 |
| WO | 2011/060264 A1 | 5/2011 |
| WO | 2011/060266 A1 | 5/2011 |
| WO | 2011/146703 A1 | 11/2011 |
| WO | 2012/021307 A2 | 2/2012 |
| WO | 2014/186453 A2 | 11/2014 |
| WO | 2019/040829 A1 | 2/2019 |
| WO | 2020/023686 A1 | 1/2020 |

OTHER PUBLICATIONS

Charlton, an Investigation into the Effect of Lateral Hillslope inputs on Floorplain Hydraulic Model Predictions, Diss.University of Bristol, Sep. 1995, 289 pages.

Decision to Grant (Translation) dated Mar. 2016 in Russian patent application 2012147835, 6 pages.

Durali M, Shameli E. Full order neural velocity and acceleration observer for a general 6-6 Stewart platform. InNetworking, Sensing and Control, 2004 IEEE International Conference on Mar. 2, 20041 (vol. 1, pp. 333-338).

(56) References Cited

OTHER PUBLICATIONS

Garreau et al., "A Knowledge-Based Approach for 3-D Reconstruction and Labeling of Vascular Networks from Biplane Angiographic Projections", IEEE Transactions on Medical Imaging, Jun. 1991, vol. 10, No. 2, 122-131.
Hartley, Euclidian Reconstruction from Uncalibrated Views, Applications of Invariance in Computer Vision, pp. 237-256, Springer Verlag, Berlin Heidelberg, 1994.
Kelly, "How to calculate 3D coordinates with two cameras, a calibration object, a java program, and a lot of MS Excel macros", Jun. 10, 2002, 9 pages.
Larionova, et al: "Roentgen absorptiometry for analyzing bone tissue mineral density in orthopaedic-and-traumatological patients", Genius Orthopedics, No. 3, 2009, pp. 98-102.
Maiocchi et al., "Operative Principles of Ilizarov", Chapter 2, 1991, 26 pages.
Nikonovas, Arkadijus. Taylor Spatial Frame: Kinematics, Mechanical Properties and Automation. Diss. University of Bristol, May 2005, 230 pages.
Ortho-SUV Frame—Art of Deformity Correction, Ortho-SUV Ltd, captured by https://web.archive.org from http://www.miito.org/download/ortho-suv-frame-eng.pdfon Jun. 13, 2010; 11 pages.
Orthofix, TL-HEX Software User's Guide: Software version 1.4, Nov. 2015, 60 pages.
Paley et al., "Deformity Correction by The Ilizarov Technique", Operative Orthopaedics, 1993, 883-948.
Paley, "The principles of deformity correction by the Ilizarov technique: Technical aspects", Techniques in Orthopaedics, 1989, vol. 4, Issue 1, 15-29.
Parikh PJ, Lam SS. A hybrid strategy to solve the forward kinematics problem in parallel manipulators. IEEE Transactions on Robotics. Feb. 2005; 21(1): 18-25.
Ren L, Feng Z, Mills JK. A self-tuning iterative calculation approach for the forward kinematics of a Stewart-Gough platform. In Mechatronics and Automation, Proceedings of the 2006 IEEE International Conference on Jun. 25, 2006, 2018-2023.
Russakoff et al., "Intensity-Based 2D-3D Spine Image Registration Incorporating a Single Fiducial Marker", Academic Radiology, Jan. 2005, vol. 12, No. 1, 37-50.
Simard et al., "The Ilizarov Procedure: Limb Lengthening and Its Implications", Physical Therapy, Jan. 1992, vol. 72, No. 1, 25-35.
Solomin et al., Deformity Correction and Fracture Treatment by software-based Ortho-SUV Frame User Manual Draft, Sep. 2011, 90 pages.
Solomin et al., Deformity Correction and Fracture Treatment by software-based Ortho-SUV Frame, User Manual, for SUV-Software vp 1.0 and vr 1.0, Vreden Russian Research Institute of Traumatology and Orthopedics, (Ortho-SUV) Ltd., Saint Petersburg, 2013, 144 pages.
Solomin et al., Deformity Correction and Fracture Treatment by software-based Ortho-SUV Frame, User Manual, for SUV-Software vp 2.1, Vreden Russian Research Institute of Traumatology and Orthopedics, (Ortho-SUV) Ltd., Saint Petersburg, Apr. 2016, 158 pages.
Solomin, The Basic Principles of External Fixation Using The Ilizarov Device, 2005, 371 pages.
Stoughton et al., "A Modified Stewart Platform Manipulator with Improved Dexterity", IEEE Transactions on Robotics and Automation, Apr. 1993, vol. 9, No. 2, 166-173.
Stryker, Hoffman LRF, Gradual Correction, Operative technique, Jul. 2016, 36 pages.
Styker, Hoffmann LRF Hexapod, Operative technique, Jul. 2016, 44 pages.
Trucco, Introductory Techniques of 3-D Computer Vision, Prentice Hall, 178-194, 1998.
Tsai, A Versatile Camera Calibration Technique for High-Accuracy 3D Machine Vision Metrology Using off-the-shelf TV Cameras and Lenses, IEEE Journal of Robotics & Automation, RA-3, No. 4, 323-344, Aug. 1987.
U.S. Appl. No. 13/111,180, filed May 19, 2011, entitled Orthopedic Fixation with Imagery Analysis, Final Rejection dated Feb. 14, 2014.
U.S. Appl. No. 13/111,180, filed May 19, 2011, entitled Orthopedic Fixation with Imagery Analysis, Final Rejection dated Oct. 23, 2015.
U.S. Appl. No. 13/111,180, filed May 19, 2011, entitled Orthopedic Fixation with Imagery Analysis, Non-final Rejection dated Apr. 9, 2015.
U.S. Appl. No. 13/111,180, filed May 19, 2011, entitled Orthopedic Fixation with Imagery Analysis, Non-final Rejection dated Jun. 6, 2013.
U.S. Appl. No. 13/111,180, filed May 19, 2011, entitled Orthopedic Fixation with Imagery Analysis, Notice of Allowability dated Nov. 17, 2016.
U.S. Appl. No. 13/111,180, filed May 19, 2011, entitled Orthopedic Fixation with Imagery Analysis, Notice of Allowance dated Aug. 26, 2016.
U.S. Appl. No. 13/111,180, filed May 19, 2011, entitled Orthopedic Fixation with Imagery Analysis, Notice of Allowance dated Dec. 16, 2016.
U.S. Appl. No. 13/111,180, filed May 19, 2011, entitled Orthopedic Fixation with Imagery Analysis, Notice of Allowance dated Sep. 17, 2014.
U.S. Appl. No. 15/461,969, filed Mar. 17, 2017, entitled Orthopedic Fixation with Imagery Analysis, Non-final Rejection dated Feb. 13, 2018.
Viceconti et al., "A software simulation of tibial fracture reduction with external fixator", Computer Methods and Programs in Biomedicine, 1993, 40, 89-94.
U.S. Appl. No. 15/247,333, filed Aug. 25, 2016.
Zhang, A Flexible New Technique for Camera Calibration, Technical Report, MSR-TR-98-71, Microsoft Research, Microsoft Corporation, Mar. 25, 1999, 22 pages.
Mur-Artal, et al., ORB-SLAM: A Versatile and Accurate Monocular SLAM System, IEEE Transactions on Robotics, vol., 31, No. 5, Oct. 2015, pp. 1147-1163.

* cited by examiner

ORTHOPEDIC FIXATION CONTROL AND MANIPULATION

CROSS REFERENCE TO RELATED APPLICATION

This application is a division of U.S. application Ser. No. 15/247,333 filed Aug. 25, 2016, the contents of which are hereby incorporated by reference in their entirety

BACKGROUND

Techniques used to treat fractures and/or deformities of anatomical structures, such as bones, can include the use of external fixators, such as hexapods and other fixation frames, which are surgically mounted to anatomical structure segments on opposed sides of a fracture site. A pair of radiographic images is taken of the fixator and anatomical structure segments at the fracture site. Data from the images is then manipulated with orthogonal projection techniques to construct a three dimensional representation of the fixator and the anatomical structures segments that can be used in developing a treatment plan, which may for example comprise realigning the anatomical structure segments through adjustments to the fixator.

Existing techniques for controlling fixator manipulation may, however, involve a number of limitations that may introduce inefficiency, complication, and unreliability. For example, some conventional techniques may require radiographic images to be orthogonal with respect to each other and aligned with anatomical axes of the patient. As yet another example, some conventional techniques may require fixator struts to be mounted into only standard ring holes or may require a reference ring to be orthogonal with respect to an anatomical structure segment to which it is mounted. Additionally, some conventional techniques may be limited with respect to how treatment plans are generated, providing few, if any, options for generating plans based on different needs and characteristics of the patient. Furthermore, some conventional techniques may be limited with respect to feedback provided to users, such as providing few, if any, confirmations of values and calculations. These and other limitations may unnecessarily increase the cost and complexity of the manipulation process. Additionally, these limitations may also reduce the reliability of the treatment plan, possibly resulting in improper alignment of anatomical structures segments during the healing process, compromised union between the anatomical structure segments, necessitating additional rounds of radiographic imaging to facilitate alignment corrections, or even necessitating additional surgical procedures.

SUMMARY

Techniques for orthopedic fixation control and manipulation, for example for correction of a deformity of an anatomical structure, such as a bone, are described herein. In particular, in some examples, a fixation apparatus may be attached to first and second anatomical structure segments. Images of the fixation apparatus and the attached anatomical structure segments may then be captured from different orientations with respect to the fixation apparatus.

In some examples, various manipulations to the fixation apparatus for correction of the anatomical structure deformity may be determined using one or more techniques. For example, in some cases, the manipulations to the fixation apparatus may be determined using a technique referred to hereinafter as Perspective Frame Matching (PFM). In the PFM technique, the images of the fixation apparatus and the attached anatomical structure segments need not necessarily be orthogonal (e.g., may be non-orthogonal) with respect to one another. In some examples of the PFM technique, configuration information associated with the fixation apparatus may be received, for example using one or more graphical user interfaces of the computing system. The received configuration information may include one or more geometric characteristics of one or more elements of the fixation apparatus, such as ring type, ring diameter, strut size, strut length, and other geometric characteristics. The captured images of the fixation apparatus and the attached anatomical structure segments may then be displayed, for example using one or more graphical user interfaces of a computing system. Upon displaying of the images, first image information may then be received, for example using the one or more graphical user interfaces of the computing system. The first image information may include indications of one or more locations, within the images, of at least part of one or more elements of the fixation apparatus. For example, the first image information may include indications of hinge locations, strut locations, and other fixation apparatus element locations within the images. Additionally, second image information may then be received, for example using the one or more graphical user interfaces of the computing system. The second image information may include indications of one or more locations, within the images, of at least part of the first and the second anatomical structure segments. For example, the second image information may include indications of reference points (e.g., end points) and center lines of the first and the second anatomical structure segments within the images. The configuration information, the first image information, and the second image information may then be used, for example, to determine positions and orientations of the first and the second anatomical structure segments in three-dimensional space. Manipulations to the fixation apparatus for correction of the anatomical structure deformity may then be determined, and indications of the determined manipulations may then be provided to one or more users. The manipulations to the fixation apparatus may include adjustments to the struts of the fixation apparatus, such as adjustments to the sizes and/or lengths of the struts.

As an alternative or in addition to the PFM technique, various other techniques may also be employed for determining manipulations to the fixation apparatus for correction of the anatomical structure deformity. For example, in some cases, a technique referred to hereinafter as the Standard technique may be employed, in which various deformity and mounting parameters may be calculated, for example by a surgeon, and entered manually into software. In some examples, in order to ensure accuracy of calculations for the Standard technique, the images of the fixation apparatus and the attached anatomical structure segments may be required to be orthogonal with respect to one another.

As another example, in some cases, yet another technique, referred to hereinafter as the Acute Intentional Deformation (AID) technique, may be employed for determining manipulations to the fixation apparatus for correction of the anatomical structure deformity. In some examples, the AID technique may be advantageous for correction of deformities, such as soft tissue injuries, in which a patient's anatomical structures and/or the fixation apparatus may be temporarily flexibly manipulated such that final strut positions may be more easily determined and obtained. In some examples of the AID technique, a user may enter deformed (e.g., initial) and aligned (e.g., final) strut positions, and the manipulations to the fixation apparatus for correction of the anatomical structure deformity may be determined based, at least in part, on the deformed and aligned strut positions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the preferred embodiments of the application, will be better understood when read in conjunction with the appended drawings. For the purposes of illustrating the methods and/or techniques of orthopedic fixation with imagery analysis, there are shown in the drawings preferred embodiments. It should be understood, however, that the instant application is not limited to the precise arrangements and/or instrumentalities illustrated in the drawings, in which:

Figure 18:
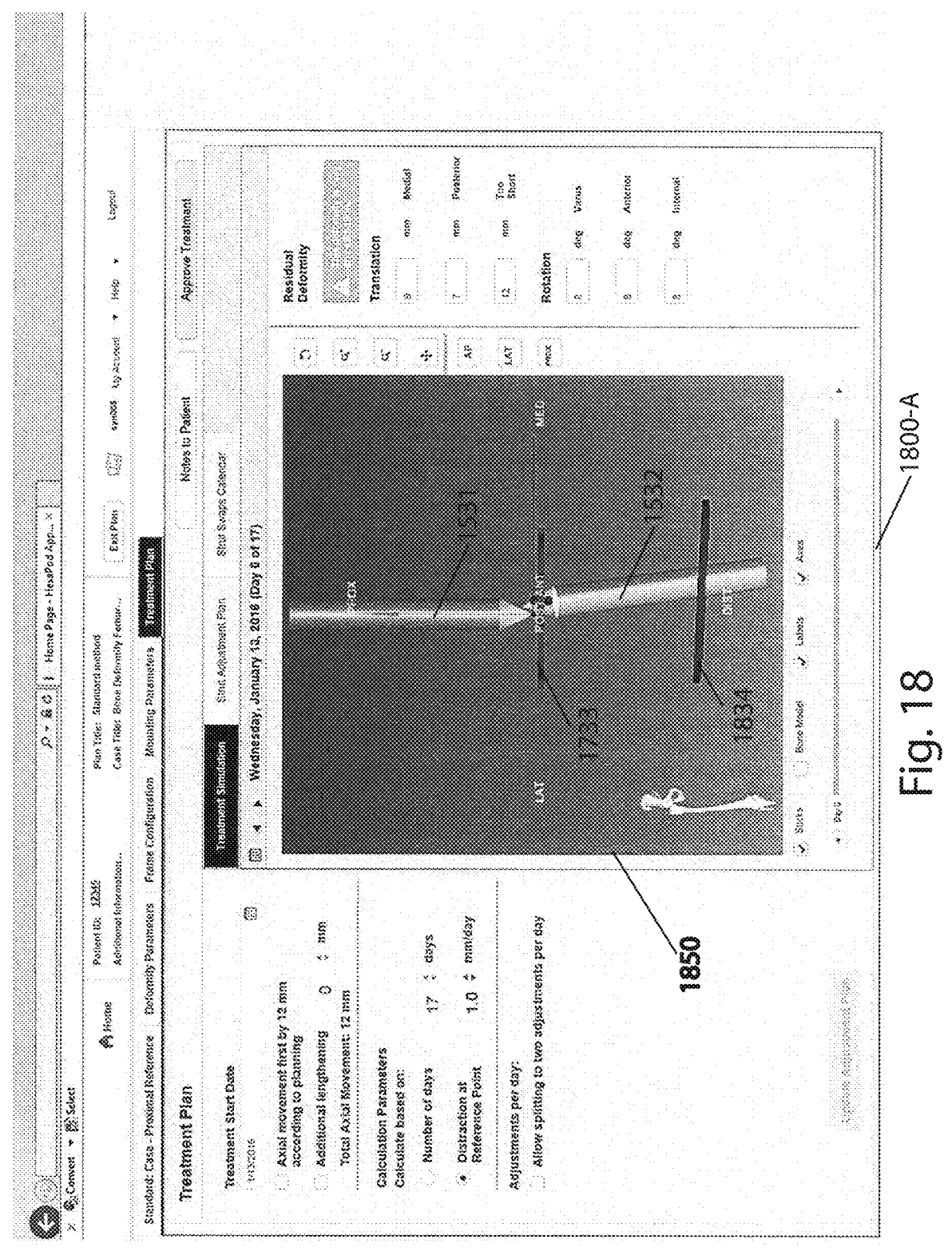

FIG. 18 is a screen shot of a first example treatment plan interface for the Standard technique;

Figure 19:
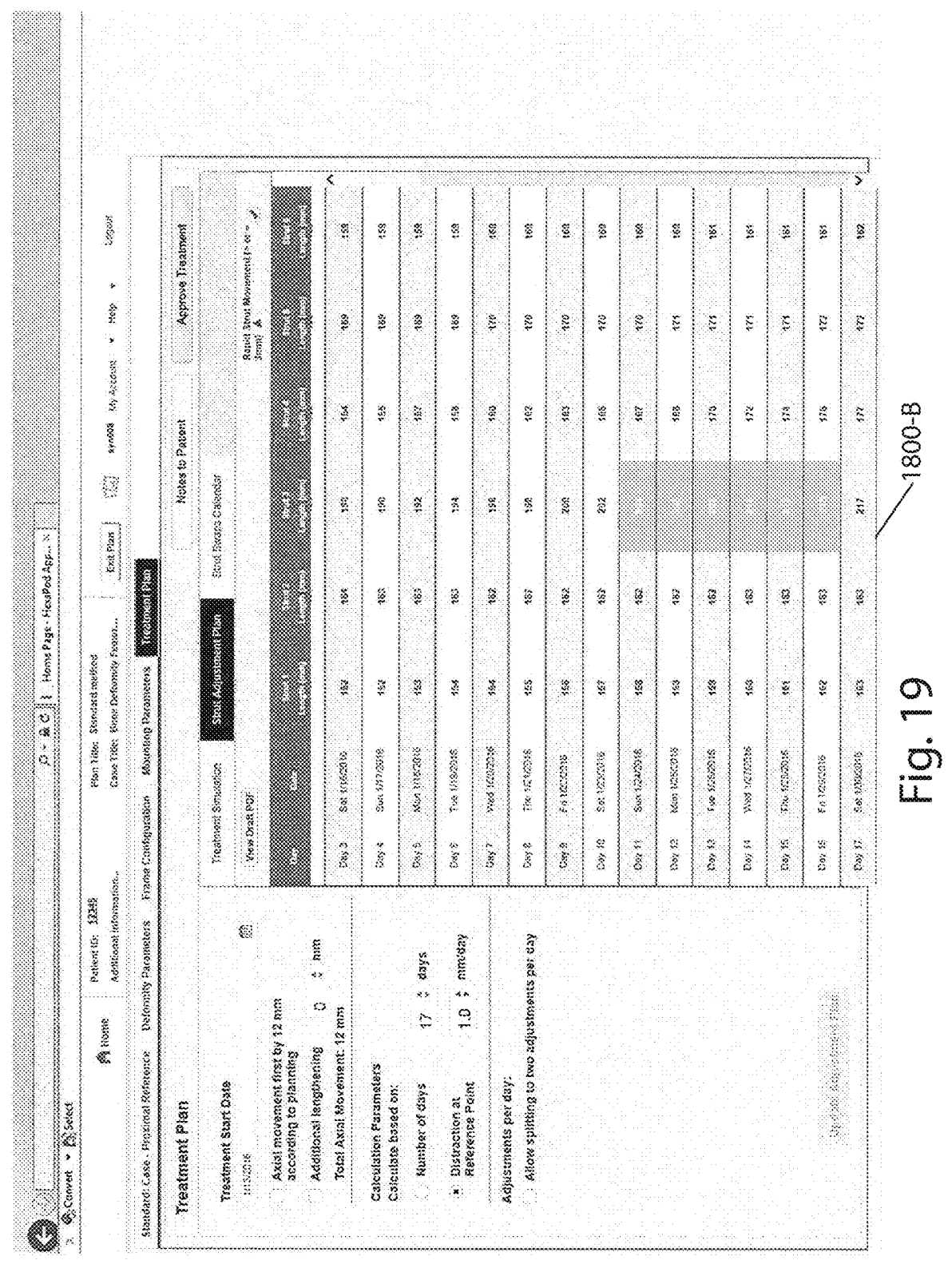

FIG. 19 is a screen shot of a second example treatment plan interface for the Standard technique;

FIG. 27 is a screen shot of a second example treatment plan interface for the AID technique;

FIG. 28 is a screen shot of a third example treatment plan interface for the AID technique;

DETAILED DESCRIPTION

Figure 1:
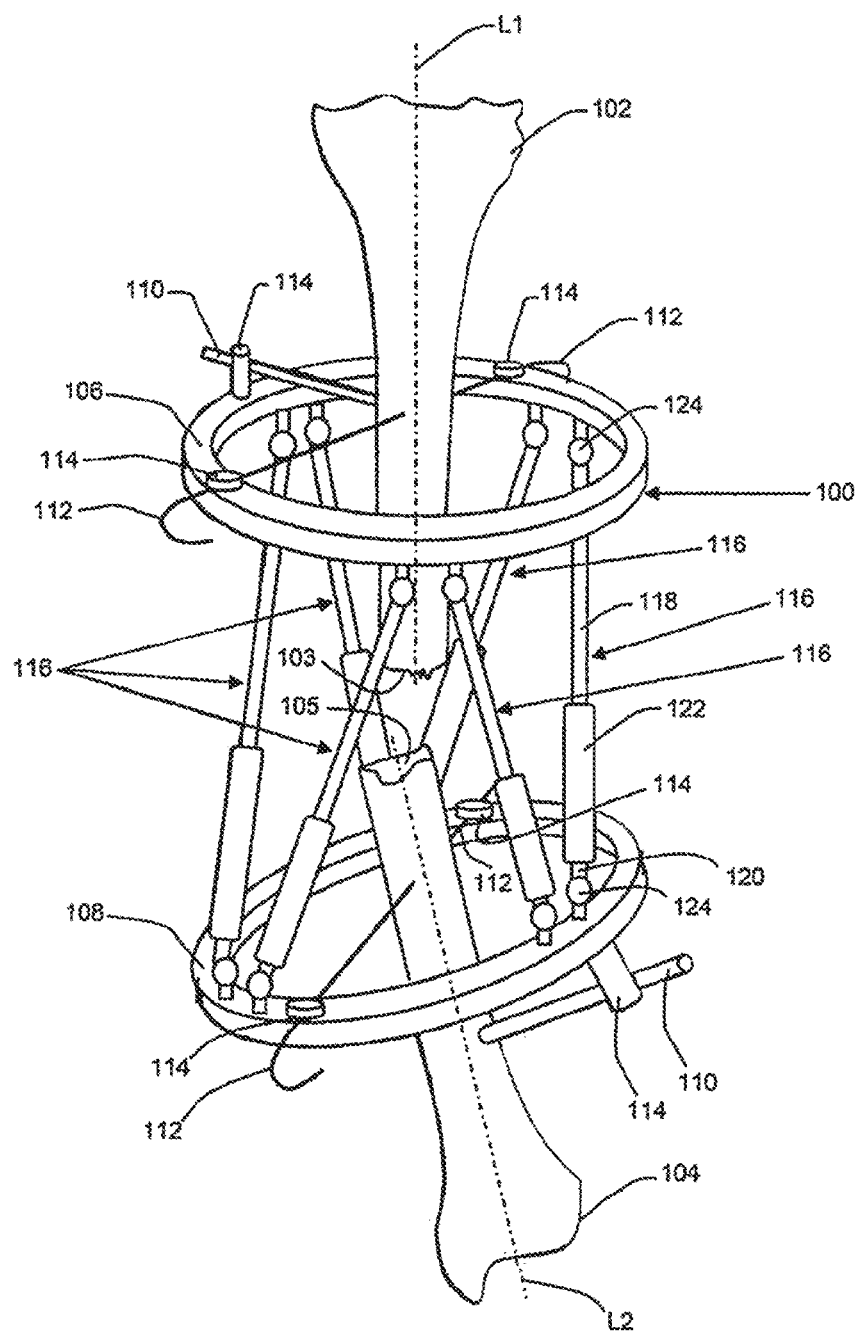
FIG. 1 is a perspective view of a fixation assembly positioned for imaging in accordance with an embodiment.

For convenience, the same or equivalent elements in the various embodiments illustrated in the drawings have been identified with the same reference numerals. Certain terminology is used in the following description for convenience only and is not limiting. The words "right", "left", "top" and "bottom" designate directions in the drawings to which reference is made. The words "inward", "inwardly", "outward", and "outwardly" refer to directions toward and away from, respectively, the geometric center of the device and designated parts thereof. The terminology intended to be non-limiting includes the above-listed words, derivatives thereof and words of similar import.

Referring initially to FIG. 1, bodily tissues, for instance first and second anatomical structure segments 102, 104, can be aligned and/or oriented to promote union or other healing between the bodily tissues. Anatomical structures may include, for example, anatomical tissue and artificial anatomical implants. Anatomical tissue may include, for example, bone or other tissue in the body. The alignment and/or orientation of the bodily tissues can be achieved by connecting the bodily tissues to an adjustable fixation apparatus, such as orthopedic fixator 100. The orthopedic fixator can comprise an external fixation apparatus that includes a plurality of discrete fixator members that remain external to the patient's body, but that are attached to respective discreet bodily tissues, for example with minimally invasive attachment members. A fixation apparatus may include, for example, a distraction osteogenesis ring system, a hexapod, or a Taylor spatial frame. By adjusting the spatial positioning of the fixator members with respect to each other, the respective bodily tissues attached thereto can be reoriented and/or otherwise brought into alignment with each other, for example to promote union between the bodily tissues during the healing process. The use of external orthopedic fixators in combination with the imagery analysis and positioning techniques described herein can be advantageous in applications where direct measurement and manipulation of the bodily tissues is not possible, where limited or minimally invasive access to the bodily tissues is desired, or the like. Some examples of orthopedic fixators and their use for correcting deformities of anatomical structure segments, as well as techniques for performing imagery analysis on the fixators and anatomical structure segments are described in U.S. patent application Ser. No. 13/111,180, entitled "ORTHOPEDIC FIXATION WITH IMAGERY ANALYSIS," filed on May 19, 2011, the entirety of which is hereby incorporated by reference.

The fixator members can be connected to each other via adjustment members, the adjustment members configured to facilitate the spatial repositioning of the fixator members with respect to each other. For example, in the illustrated embodiment, the orthopedic fixator 100 comprises a pair of fixator members in the form of an upper fixator ring 106 and a lower fixator ring 108. The fixator rings 106, 108 can be constructed the same or differently. For instance, the fixator rings 106, 108 can have diameters that are the same or different. Similarly, the fixator rings 106, 108 can be constructed with varying cross sectional diameters, thicknesses, etc. It should be appreciated that the fixator members of the orthopedic fixator 100 are not limited to the illustrated upper and lower fixator rings 106, 108, and that the orthopedic fixator 100 can be alternatively constructed. For example, additional fixator rings can be provided and interconnected with the fixator ring 106 and/or 108. It should further be appreciated that the geometries of the fixator members are not limited to rings, and that at least one, such as all of the fixator members can be alternatively constructed using any other suitable geometry.

The first and second anatomical structure segments 102, 104 can be rigidly attached to the upper and lower fixator rings 106, 108, respectively, with attachment members that can be mounted to the fixator rings 106, 108. For example, in the illustrated embodiment, attachment members are provided in the form of attachment rods 110 and attachment wires 112.

The rods 110 and the wires 112 extend between proximal ends attached to mounting members 114 that are mounted to the fixator rings 106, 108, and opposed distal ends that are inserted into or otherwise secured to the anatomical structure segments 102, 104. The mounting members 114 can be removably mounted to the fixator rings 106, 108 at predefined points along the peripheries of the fixator rings 106, 108, for example by disposing them into threaded apertures defined by the fixator rings. With respect to each fixator ring 106, 108, the mounting members 114 can be mounted to the upper surface of the ring, the lower surface of the ring, or any combination thereof. It should be appreciated that the attachment members are not limited to the configuration of the illustrated embodiment. For example, any number of attachment members, such as the illustrated rods 110 and wires 112 and any others, can be used to secure the anatomical structure segments to respective fixator members as desired. It should further be appreciated that one or more of the attachment members, for instance the rods 110 and/or wires 112, can be alternatively configured to mount directly to the fixator rings 106, 108, without utilizing mounting members 114.

The upper and lower fixator rings 106, 108 can be connected to each other by at least one, such as a plurality of adjustment members. At least one, such as all, of the adjustment members can be configured to allow the spatial positioning of the fixator rings with respect to each other to be adjusted. For example, in the illustrated embodiment, the upper and lower fixator rings 106, 108 are connected to each other with a plurality of adjustment members provided in the form of adjustable length struts 116. It should be appreciated that the construction of the orthopedic fixator 100 is not limited to the six struts 116 of the illustrated embodiment, and that more or fewer struts can be used as desired.

Each of the adjustable length struts 116 can comprise opposed upper and lower strut arms 118, 120. Each of the upper and lower strut arms 118, 120 have proximal ends disposed in a coupling member, or sleeve 122, and opposed distal ends that are coupled to universal joints 124 mounted to the upper and lower fixator rings 106, 108, respectively. The universal joints of the illustrated embodiment are disposed in pairs spaced evenly around the peripheries of the upper and lower fixator rings 106, 108, but can be alternatively placed in any other locations on the fixator rings as desired.

The proximal ends of the upper and lower strut arms 118, 120 of each strut 116 can have threads defined thereon that are configured to be received by complementary threads defined in the sleeve 122, such that when the proximal ends of the upper and lower strut arms 118, 120 of a strut 116 are received in a respective sleeve 122, rotation of the sleeve 122 causes the upper and lower strut arms 118, 120 to translate within the sleeve 122, thus causing the strut 116 to be elongated or shortened, depending on the direction of rotation. Thus, the length of each strut 116 can be independently adjusted with respect to the remaining struts. It should be appreciated that the adjustment members are not limited to the length adjustable struts 116 of the illustrated embodiment, and that the adjustment members can be alternatively constructed as desired, for example using one or more alternative geometries, alternative length adjustment mechanisms, and the like.

The adjustable length struts 116 and the universal joints 124 by which they are mounted to the upper and lower fixator rings 106, 108, allow the orthopedic fixator 100 to function much like a Stewart platform, and more specifically like a distraction osteogenesis ring system, a hexapod, or a Taylor spatial frame. That is, by making length adjustments to the struts 116, the spatial positioning of the upper and lower fixator rings 106, 108, and thus the anatomical structure segments 102, 104 can be altered. For example, in the illustrated embodiment the first anatomical structure segment 102 is attached to the upper fixator ring 106 and the second anatomical structure segment 104 is attached to the lower fixator ring 108. It should be appreciated that attachment of the first and second anatomical structure segments 102, 104 to the upper and lower fixator rings 106, 108 is not limited to the illustrated embodiment (e.g., where the central longitudinal axes L1, L2 of the first and second anatomical structure segments 102, 104 are substantially perpendicular to the respective planes of the upper and lower fixator rings 106, 108), and that a surgeon has complete flexibility in aligning the first and second anatomical structure segments 102, 104 within the upper and lower fixator rings 106, 108 when configuring the orthopedic fixator 100.

By varying the length of one or more of the struts 116, the upper and lower fixator rings 106, 108, and thus the anatomical structure segments 102 and 104 can be repositioned with respect to each other such that their respective longitudinal axes L1, L2 are substantially aligned with each other, and such that their respective fractured ends 103, 105 abut each other, so as to promote union during the healing process. It should be appreciated that adjustment of the struts 116 is not limited to the length adjustments as described herein, and that the struts 116 can be differently adjusted as desired. It should further be appreciated that adjusting the positions of the fixator members is not limited to adjusting the lengths of the length adjustable struts 116, and that the positioning of the fixator members with respect to each other can be alternatively adjusted, for example in accordance the type and/or number of adjustment members connected to the fixation apparatus.

Repositioning of the fixator members of an orthopedic fixation apparatus, such as orthopedic fixator 100, can be used to correct displacements of angulation, translation, rotation, or any combination thereof, within bodily tissues.

A fixation apparatus, such as orthopedic fixator 100, utilized with the techniques described herein, can correct a plurality of such displacement defects individually or simultaneously. However, it should be appreciated that the fixation apparatus is not limited to the illustrated orthopedic fixator 100, and that the fixation apparatus can be alternatively constructed as desired. For example, the fixation apparatus can include additional fixation members, can include fixation members having alternative geometries, can include more or fewer adjustment members, can include alternatively constructed adjustment members, or any combination thereof.

Figure 2:
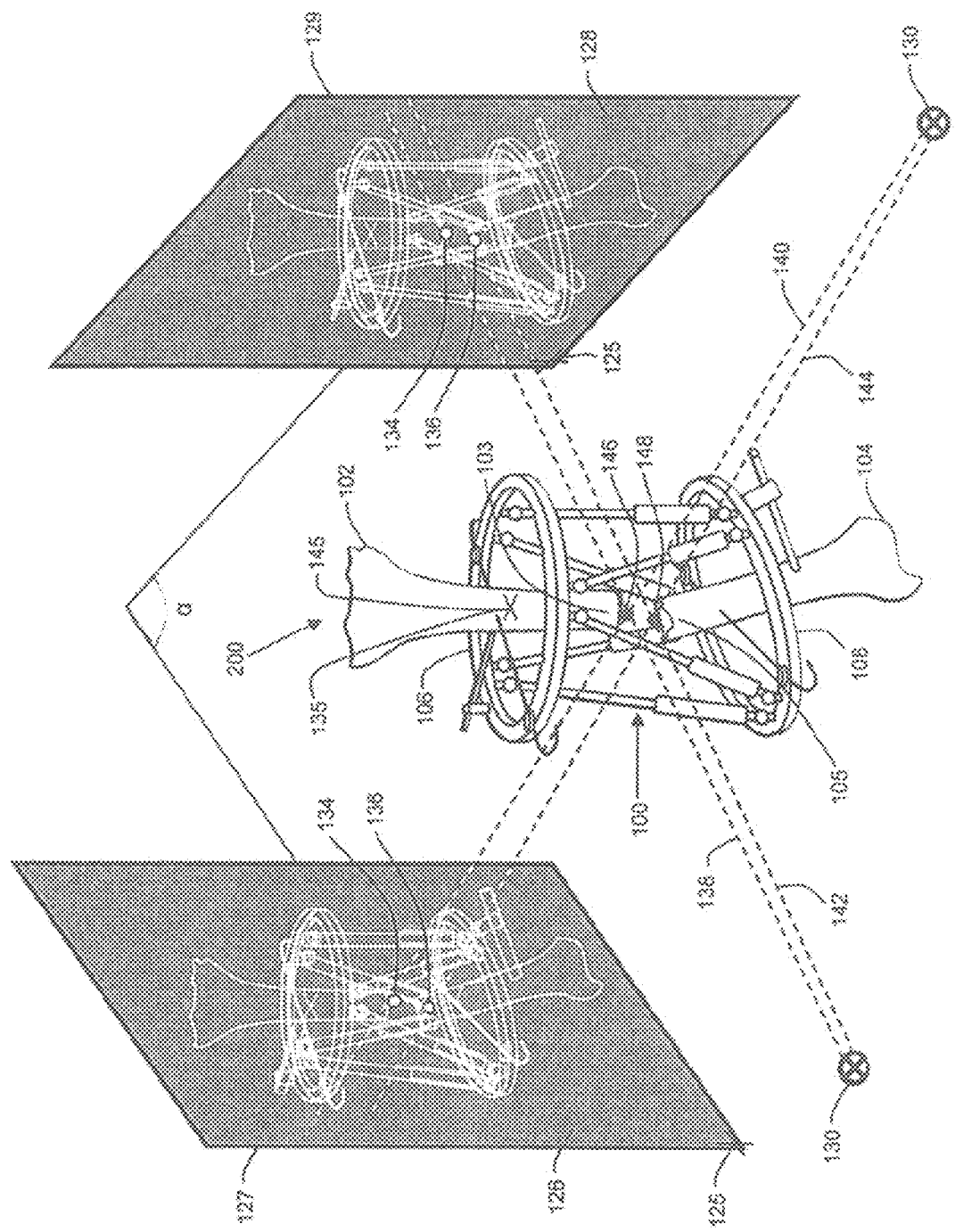
FIG. 2 is a perspective view of an example imaging process of the fixation assembly illustrated in FIG. 1.

Referring now to FIG. 2, an example imaging of a fixation apparatus will now be described in detail. The images can be captured using the same or different imaging techniques. For example, the images can be acquired using x-ray imaging, computer tomography, magnetic resonance imaging, ultrasound, infrared imaging, photography, fluoroscopy, visual spectrum imaging, or any combination thereof.

The images can be captured from any position and/or orientation with respect to each other and with respect to the fixator 100 and the anatomical structure segments 102, 104. In other words, there is no requirement that the captured images be orthogonal with respect to each other or aligned with anatomical axes of the patient, thereby providing a surgeon with near complete flexibility in positioning the imagers 130. Preferably, the images 126, 128 are captured from different directions, or orientations, such that the images do not overlap. For example, in the illustrated embodiment, the image planes of the pair of images 126, 128 are not perpendicular with respect to each other. In other words, the angle α between the image planes of the images 126, 128 is not equal to 90 degrees, such that the images 126, 128 are non-orthogonal with respect to each other. Preferably, at least two images are taken, although capturing additional images may increase the accuracy of the method.

The images 126, 128 can be captured using one or more imaging sources, or imagers, for instance the x-ray imagers 130 and/or corresponding image capturing devices 127, 129. The images 126, 128 can be x-ray images captured by a single repositionable x-ray imager 130, or can be captured by separately positioned imagers 130. Preferably, the position of the image capturing devices 127, 129 and/or the imagers 130 with respect to the space origin 135 of the three dimensional space, described in more detail below, are known. The imagers 130 can be manually positioned and/or oriented under the control of a surgeon, automatically positioned, for instance by a software assisted imager, or any combination thereof. The fixator 100 may also have a respective fixator origin 145.

Figure 3A:
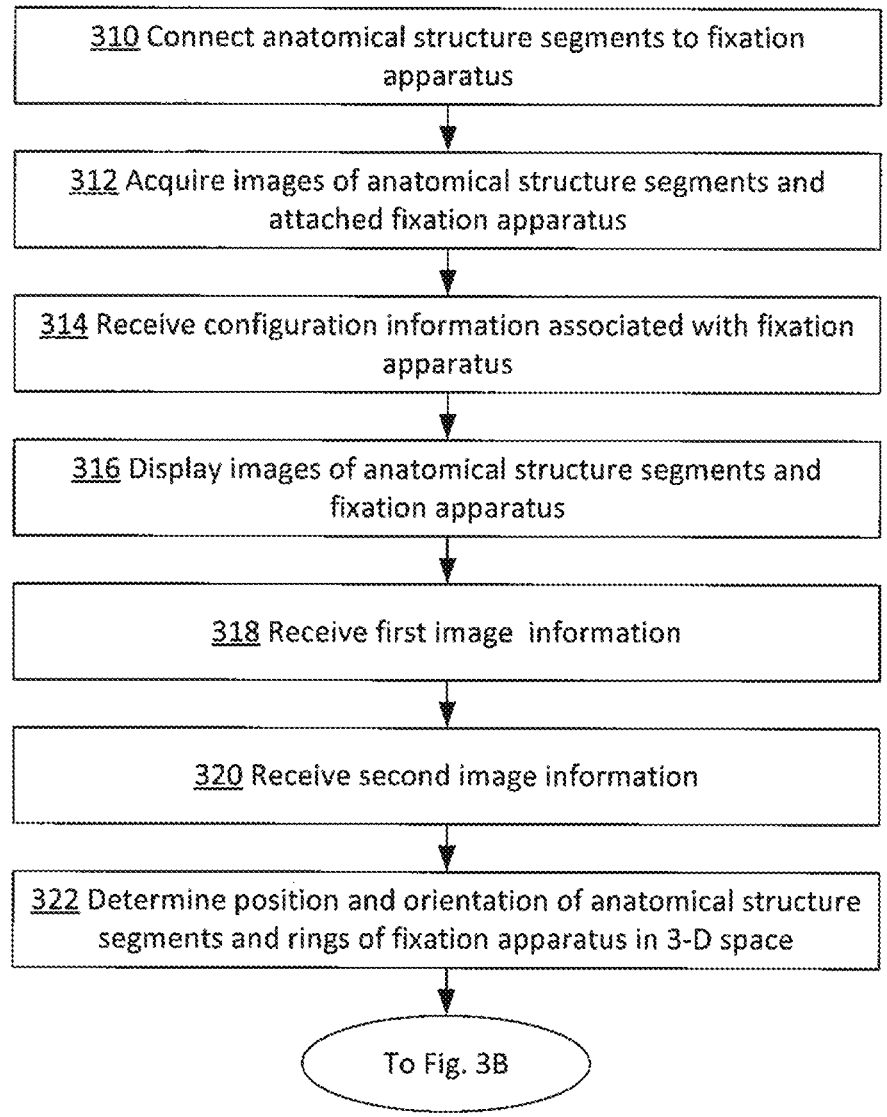
FIGS. 3A and 3B are flow diagrams illustrating an example process for controlling manipulation of a fixation apparatus to correct an anatomical structure deformity.
Figure 3B:
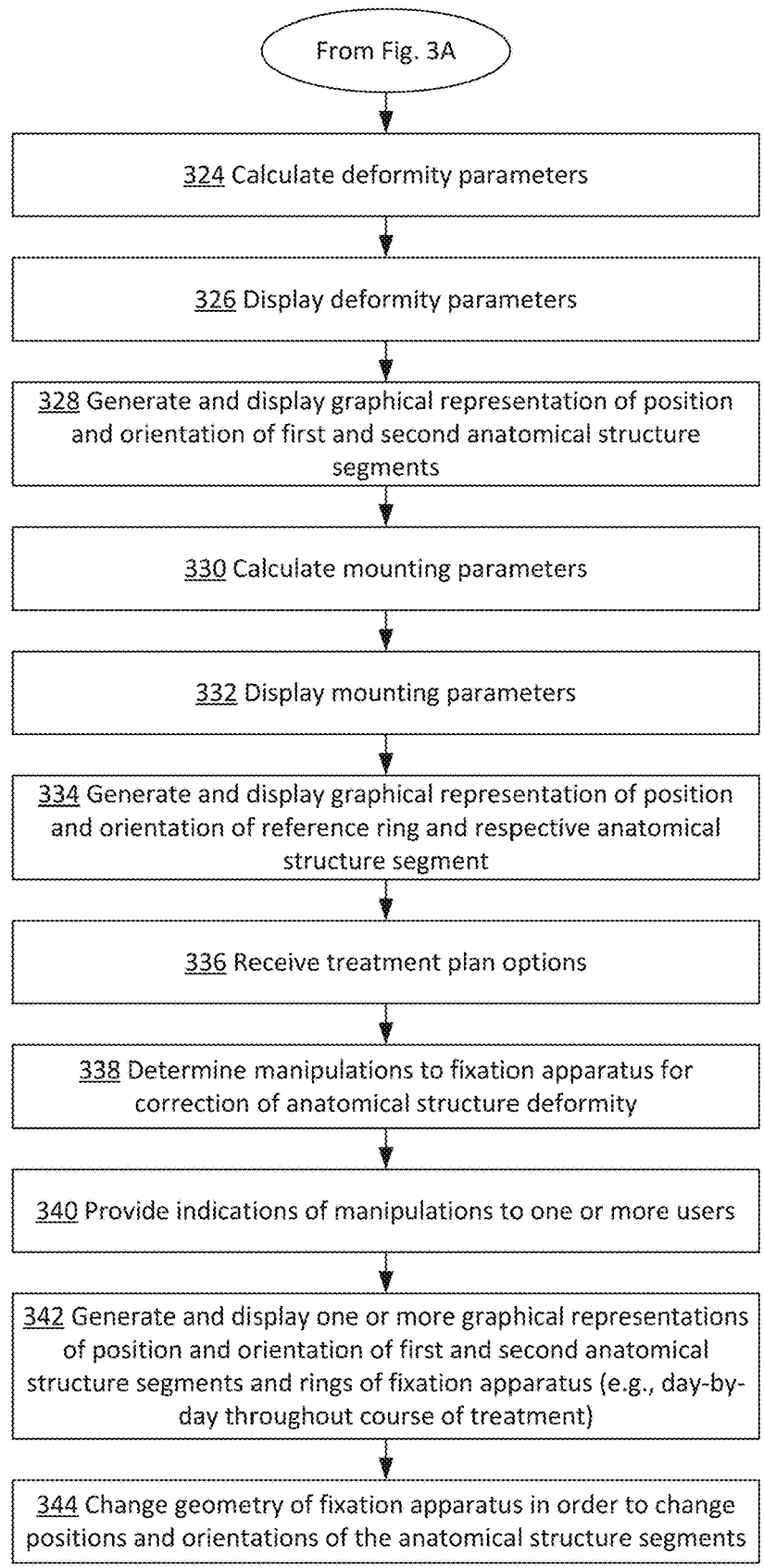

Referring now to FIGS. 3A and 3B, an example process for controlling manipulation of a fixation apparatus including rings and struts to correct an anatomical structure deformity of first and second anatomical structure segments will now be described in detail. In particular, at operation 310, first and second anatomical structure segments are attached to a fixation apparatus, for example as shown in FIG. 1 and described in detail above. At operation, 312, first and second images of the fixation apparatus and the attached first and second anatomical structure segments are captured, for example as shown in FIG. 2 and described in detail above.

Figure 4:
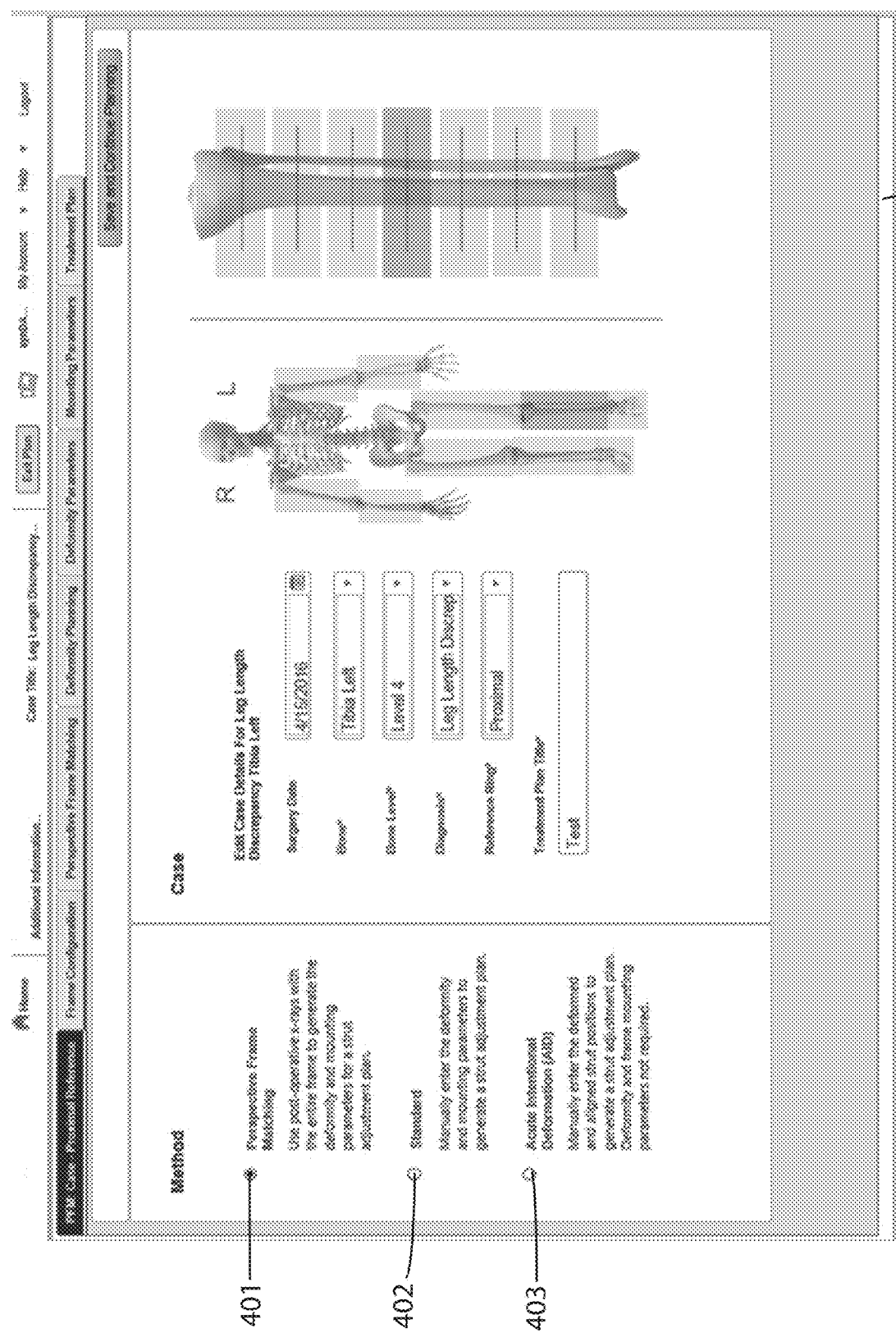
FIG. 4 is a screen shot of an example interface for selecting a Perspective Frame Matching (PFM) technique.

The remaining operations of the process of FIGS. 3A and 3B (e.g., operations 314-342) will now be described in association with a treatment technique referred to hereinafter as Perspective Frame Matching, in which images, such as post-operative x-rays, may be used along with a frame to generate deformity and mounting parameters for a strut adjustment plan. For example, referring now to FIG. 4, an example treatment planning technique selection interface 400-A is shown. In the example of FIG. 4, the user has selected option 401 in order to use the Perspective Frame Matching (PFM) technique, which will now be described in detail with reference to FIGS. 5-13. Additionally, in other examples, a user may select option 402 to use the Standard technique, which is described in detail below with reference to FIGS. 14-20. Furthermore, in other examples, a user may select option 403 to use the Acute Intentional Deformation (AID) technique, which is described in detail below with reference to FIGS. 21-28. Operations 314-342 may be performed by a computing system, for example including one or more computing devices.

Figure 5:
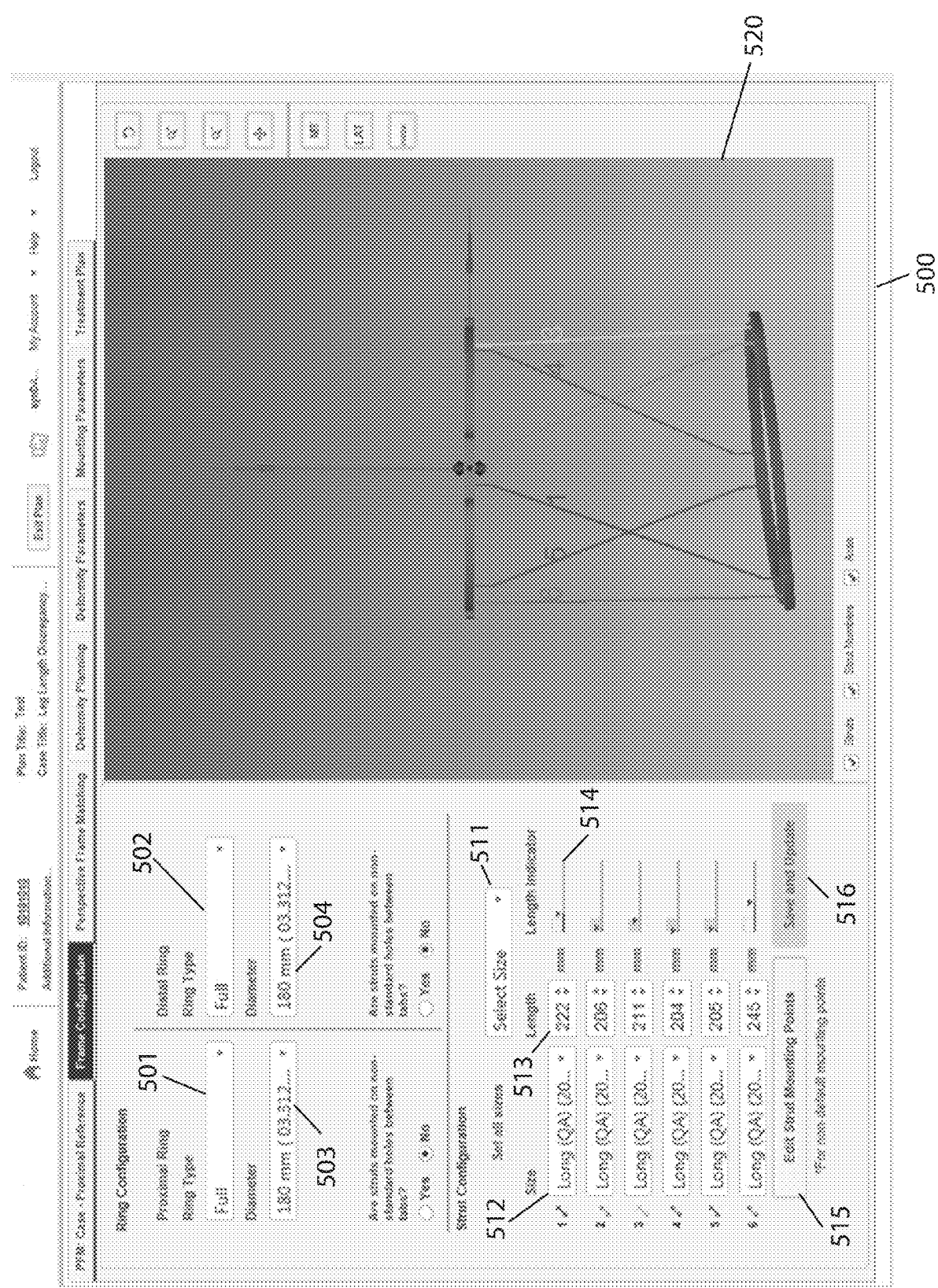
FIG. 5 is a screen shot of an example configuration information entry interface for the PFM technique.

Referring back to FIG. 3A, at operation 314, configuration information associated with a fixation apparatus is received, for example using one or more graphical user interfaces of a computing system. In some examples, the configuration information may include one or more geometric characteristics (e.g., size, length, diameter, etc.) of one or more elements of the fixation apparatus, such as struts, hinges, rings, and others. In some examples, the configuration information may include information such as ring types (e.g., full ring, foot plate, etc.), indications of mounting points (e.g., ring holes) used for strut mounting, and other information. In some examples, the configuration information may also include information about marker elements, for example that are mounted to components of the fixation apparatus, such as struts, hinges, and rings. Referring now to FIG. 5, an example configuration information entry interface 500 is shown. As shown, interface 500 includes ring type indicators 501 and 502, which, in this example, are drop down menus that may be used to select ring types for the proximal and distal rings, respectively. Indicators 501 and 502 are set to the "Full" option to indicate that the proximal and distal rings are full rings. Interface 500 also includes diameter indicators 503 and 504, which, in this example, are drop down menus that may be used to select diameters or lengths for the proximal and distal rings, respectively.

The interface 500 also includes controls for entry of strut information. In particular, interface 500 includes six drop down menus 512 may each be used to indicate a size of a respective strut. Global strut size indicator 511 may also be used to globally select a size for all six struts. Length selectors 513 may be each be used to select a length of a respective strut. Length indicators 514 may be each be used to provide a visual representation of the lengths of the respective struts. It is noted that the length indicators 514 do not necessarily depict the actual exact length of each strut, but rather represent the comparative lengths of the struts with respect to one another.

In some examples, software may initially assume that each strut is mounted into standard mounting points (e.g., ring holes), which are commonly or typically used mounting points for a respective fixation apparatus. It is noted, however, that struts are not necessarily required to be mounted into standard mounting points. For example, in some cases, selecting Edit Strut Mounting Points button 515 may allow a user to select non-standard mounting points for one or more struts. For example, in some cases, selection of button 515 may cause display of a graphical representation of rings including representations of standard and non-standard mounting points on the rings. The user may then, for each strut, select a graphical representation of a standard or non-standard mounting point at which the strut is mounted.

Save and Update button 516 may be selected to save and update the configuration information values shown in interface 500. In some examples, selection of button 516 may cause interface 500 to display and/or update a graphical representation 520 of the fixation apparatus generated based, at least in part, on the entered configuration information. The graphical representation 520 may be displayed using one or more graphical user interfaces of a computing system. As shown, graphical representation 520 includes six struts that may be color-coded in multiple colors for easy identification. For example, in some cases, each of the struts (or at least two of the struts) may be shown in different colors with respect to one another. The struts in graphical representation 520 may have sizes, lengths, mounting points, and other features corresponding to entered configuration information. Graphical representation 520 also depicts the fixator rings, which may have diameters/lengths, ring types, and other features corresponding to entered configuration information. Graphical representation 520 may, for example, improve efficiency and reliability by providing the user with a visual confirmation of information entered into interface 500, for example to allow fast and easy identification of errors or other problems.

Figure 6:
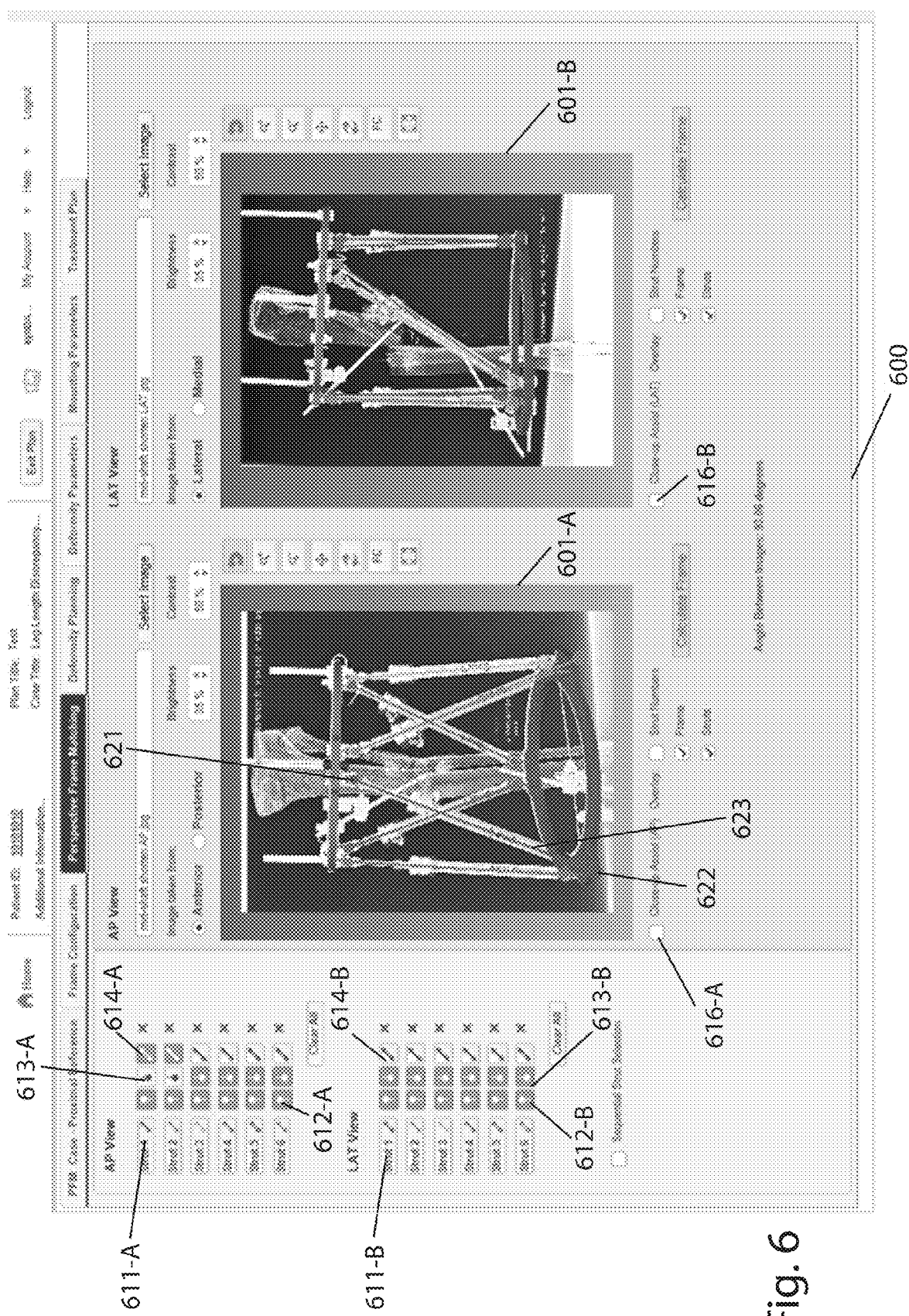
FIG. 6 is a screen shot of an example first image information entry interface for the PFM technique.

At operation 316, images of the fixation apparatus and the first and second anatomical structure segments attached thereto are displayed, for example using one or more graphical user interfaces of a computing system. The displayed images may include images that were captured at operation 312, such as using x-ray imaging, computer tomography, magnetic resonance imaging, ultrasound, infrared imaging, photography, fluoroscopy, visual spectrum imaging, or any combination thereof. Techniques for acquiring images of the fixation apparatus and the first and second anatomical structure segments are described in detail above and are not repeated here. As set forth above, the acquired and displayed images need not necessarily be orthogonal to one another. Referring now to FIG. 6, an example first image information entry interface 600 is shown. As shown, interface 600 includes images 601-A and 601-B, which show the fixation apparatus and first and second anatomical structure segments from different angles. In the example of FIG. 6, image 601-A corresponds to an anteroposterior (AP) View, while image 601-B corresponds to a lateral (LAT) view. In some examples, the displayed images 601-A-B may be loaded and saved in computer memory, for example in a library, database or other local collection of stored images. The displayed images 601-A-B may then be selected and retrieved, acquired, and/or received from memory for display.

At operation 318, first image information is received, for example using one or more graphical user interfaces of a computing system. The first image information may include indications of one or more locations, within the images, of at least part of one or more elements of the fixation apparatus. For example, the first image information may include one or more indications of locations of struts, hinges, rings, and other fixator elements. In some examples, the first image information may also include information about locations, within the images, of marker elements, for example that are mounted to components of the fixation apparatus, such as struts, hinges, and rings. In some cases, the first image information may include points representing locations of hinges and/or lines or vectors representing locations of struts. In some examples, the first image information may be entered into a computing system by selecting or indicating one or more locations within the displayed images, for example using a mouse, keyboard, touchscreen or other user input devices. In particular, using one or more input devices, a user may select points or other locations in the images, draw lines, circles, and generate other graphical indications within the images. For example, in some cases, a user may generate a point or small circle at a particular location in an image to indicate a location (e.g., center point) of a hinge within the image. As another example, in some cases, a user may generate a line and/or vector within an image to indicate a location and/or length of a strut within the image.

For example, as shown in FIG. 6, interface 600 includes six AP View strut indicator buttons 611-A corresponding to each of the six struts of the fixation apparatus shown in AP View image 601-A. Each button 611-A includes text indicating a respective strut number (i.e., Strut 1, Strut 2, Strut 3, Strut 4, Strut 5, Strut 6). Buttons 611-A may be selected by a user to indicate a strut for which first image information (e.g., hinge locations, strut locations, etc.) will be provided by the user in AP View image 601-A. For example, in some cases, to provide first image information for Strut 1 in AP View image 601-A, a user may first select the top strut indicator button 611-A (labeled with the text "Strut 1") in order to indicate to the software that the user is about to provide first image information for Strut 1 within AP View image 601-A. In some cases, the strut indicator button 611-A for Strut 1 may be pre-selected automatically for the user. Upon selection (or automatic pre-selection) of the strut indicator button 611-A for Strut 1, the user may proceed to draw (or otherwise indicate) a representation of Strut 1 within AP View image 601-A. For example, in some cases, the user may use a mouse or other input device to select a location 621 (e.g., a center point) of a proximal hinge for Strut 1 within image 601-A. In some examples, the user may then use a mouse or other input device to select a location 622 (e.g., a center point) of the distal hinge of Strut 1 within image 601-A. In some examples, the user may indicate the location and/or length of Strut 1 by selecting the locations of the proximal and distal hinges and/or as the endpoints of a line or vector that represents the location and/or length of Strut 1. For example, as shown in FIG. 6, the software may generate points or circles at the locations 621 and 622 of the proximal and distal hinges selected by the user within image 601-A. Additionally, the software may generate a line 623 representing the location and/or length of Strut 1 that connects the points or circles at the locations 621 and 622 and of the proximal and distal hinges selected by the user within image 601-A. Any other appropriate input techniques may also be employed by the user to indicate a location and/or length of Strut 1 within image 610-A, such as generating line 623 by dragging and dropping a mouse, using a finger and/or pen on a touch screen, keyboard, and others. In some examples, the above described process may be repeated to draw points representing proximal and distal hinges and lines representing the locations and/or lengths of each of the six struts in the AP View image 601-A. Furthermore, the above described process may also be repeated using LAT View strut indicator buttons 611-B to draw points representing proximal and distal hinges and lines representing the locations and/or lengths of each of the six struts in the LAT View image 601-B.

In some examples, the first image information generated within images 601-A and 601-B may include color-coded graphical representations of the struts, for example to enable the graphical representations to be more clearly associated with their respective struts. For example, in FIG. 6, the graphical representations (e.g., points, circles, and/or lines) of Strut 1 in images 601A- and 601-B may be colored in red. This may match a strut icon (which may also be colored red) displayed in the strut indicator buttons 611-A and 611-B for Strut 1 (displayed to the right of the text "Strut 1" in buttons 611-A and 611-B). As another example, in FIG. 6, the graphical representations (e.g., points, circles, and/or lines) of Strut 3 in images 601-A and 601-B may be colored in yellow. This may match a strut icon (which may also be colored yellow) displayed in the strut indicator buttons 611-A and 611-B for Strut 3 (displayed to the right of the text "Strut 3" in buttons 611-A and 611-B).

Figure 7:
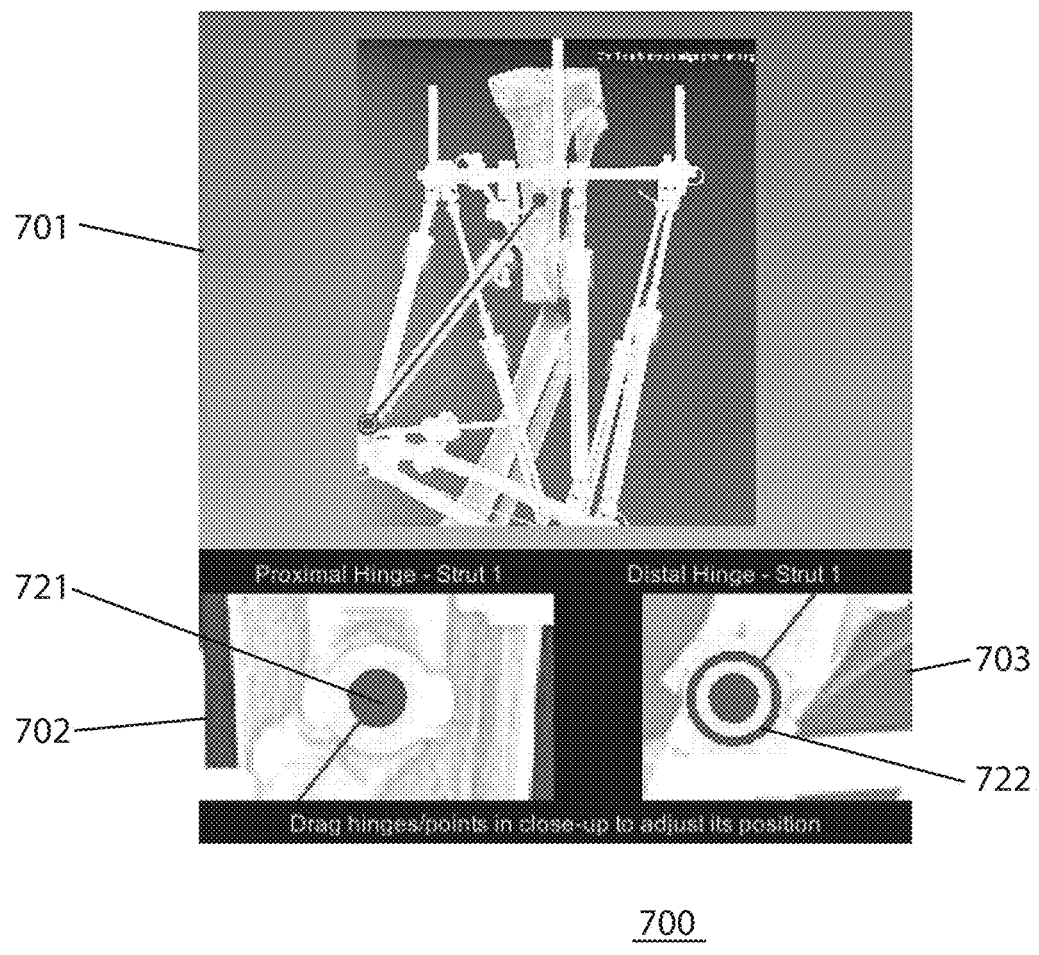
FIG. 7 is a screen shot of an example close-up assist interface for the PFM technique.

FIG. 6 includes an AP View close-up assist checkbox 616-A and a LAT View close-up assist checkbox 616-B, for example provided using one or more graphical interfaces of a computing system. Selection of checkboxes 616-A and 616-B may allow close-up views of areas of images 601-A and 601-B surrounding the proximal and distal hinges of the struts that are currently being drawn by the user. This may enable more accurate indications of the locations (e.g., center points) of the hinges. Referring now to FIG. 7, close-up assist interface 700 depicts another AP View image 701 with the close-up assist being selected to provide a proximal hinge close-up assist view 702 and a distal hinge close-up assist view 703. As shown, proximal hinge close-up assist view 702 provides an enlarged view of an area of AP View image 701 associated with the proximal hinge, while distal hinge close-up assist view 703 provides an enlarged view of an area of AP View image 701 associated with the distal hinge. The user may manipulate (e.g., drag and drop) the location of the point/circle 721 in proximal hinge close-up assist view 702 in order to more accurately depict the center point of the proximal hinge. The user may also manipulate (e.g., drag and drop) the location of the point/circle 722 in distal hinge close-up assist view 703 in order to more accurately depict the center point of the distal hinge. As should be appreciated, corresponding close-up assist views similar to views 702 and 703 may also be provided for a respective LAT View image, for example using one or more graphical interfaces of a computing system.

Referring back to FIG. 6, to the right of buttons 611-A, are six proximal hinge selector buttons 612-A. Additionally, to the right of buttons 612-A, are six distal hinge selector buttons 613-A. Furthermore, to the right of buttons 613-A, are six strut line selector buttons 614-A. In some examples, buttons 612-A and/or 613-A may be selected to use the locations (e.g., center points) of the proximal and/or distal hinges indicated in AP View image 601-A in calculating positions and orientations of the first and the second anatomical structure segments and rings of the fixation apparatus in three-dimensional space (see operation 322). Additionally, in some examples, buttons 612-A and/or 613-A may be selected to use the lines or vectors representing the location and/or length of struts indicated in AP View image 601-A in calculating positions and orientations of the first and the second anatomical structure segments in three-dimensional space. Similarly, buttons 612-B, 613-B, and 614-B may be used to select the use of locations (e.g., center points) of the proximal and/or distal hinges or strut lines or vectors indicated in LAT View image 601-B in calculating positions and orientations of the first and the second anatomical structure segments in three-dimensional space.

Referring again to FIG. 3A, at operation 320, second image information is received, for example using one or more graphical user interfaces of a computing system. The second image information may include indications of one or more locations, within the images, of at least part of the first and the second anatomical structure segments. In some examples, the second image information may include indications of center lines of the first and the second anatomical structure segments and/or one or more reference points (e.g., end points) of the first and the second anatomical structure segments. In some examples, the second image information may also include indications of locations of marker elements, for example implanted or otherwise associated with the first and the second anatomical structure segments. In some examples, the second image information may be entered into a computing system by selecting or indicating one or more locations within the displayed images, for example using a mouse, keyboard, touchscreen or other user input devices. In particular, using one or more input devices, a user may select points or other locations in the images, draw lines, circles, and generate other graphical indications within the images. For example, in some cases, a user may generate points or small circles at particular locations in an image to indicate one or more reference points (e.g., end points) of the first and the second anatomical structure segments within the images. As another example, in some cases, a user may generate a line within an image to indicate a center line of the first and the second anatomical structure segments within the images.

Figure 8A:
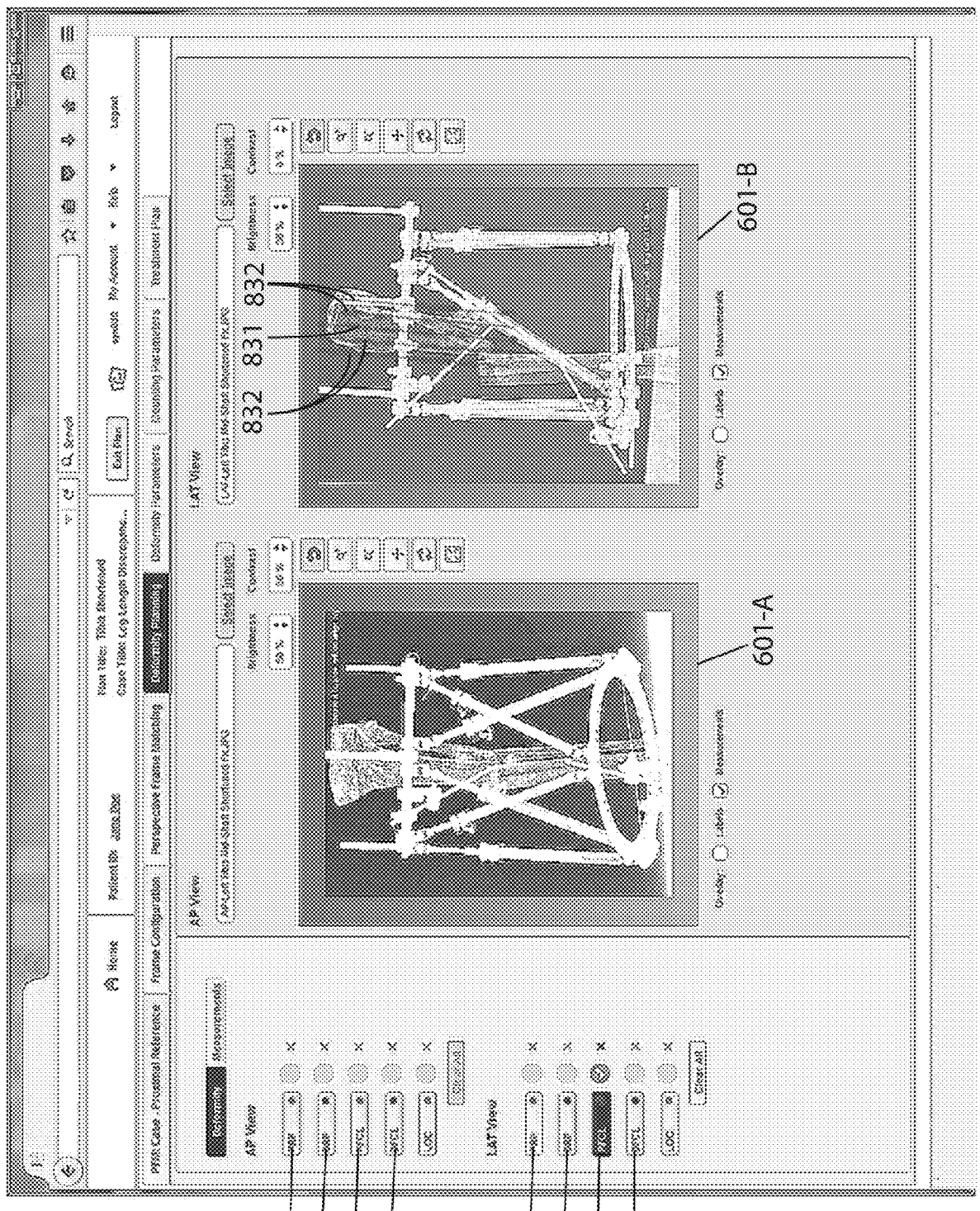
FIGS. 8A-8H are screen shots of an example second image information entry interface for the PFM technique.
Figure 8B:
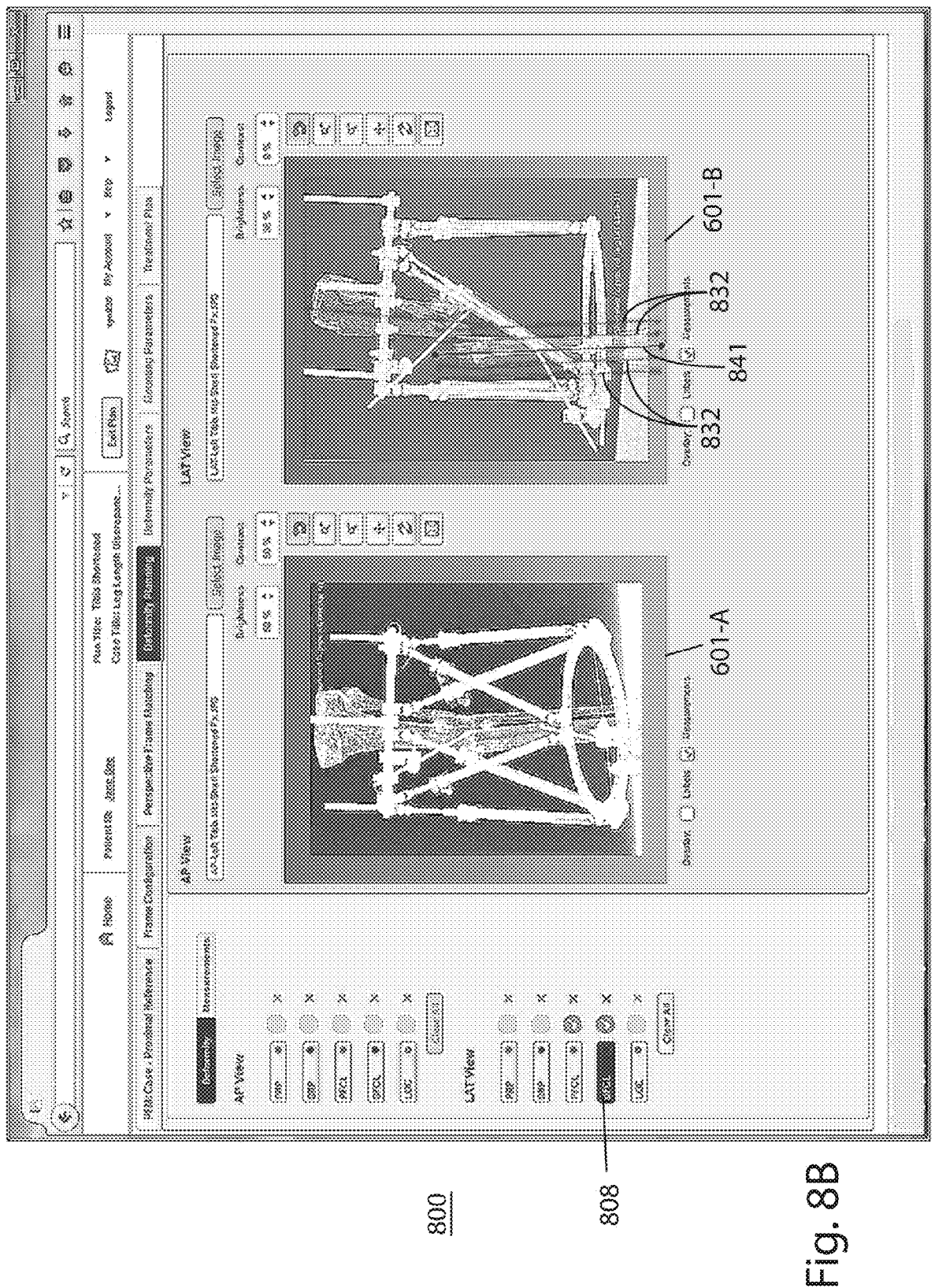
Figure 8C:
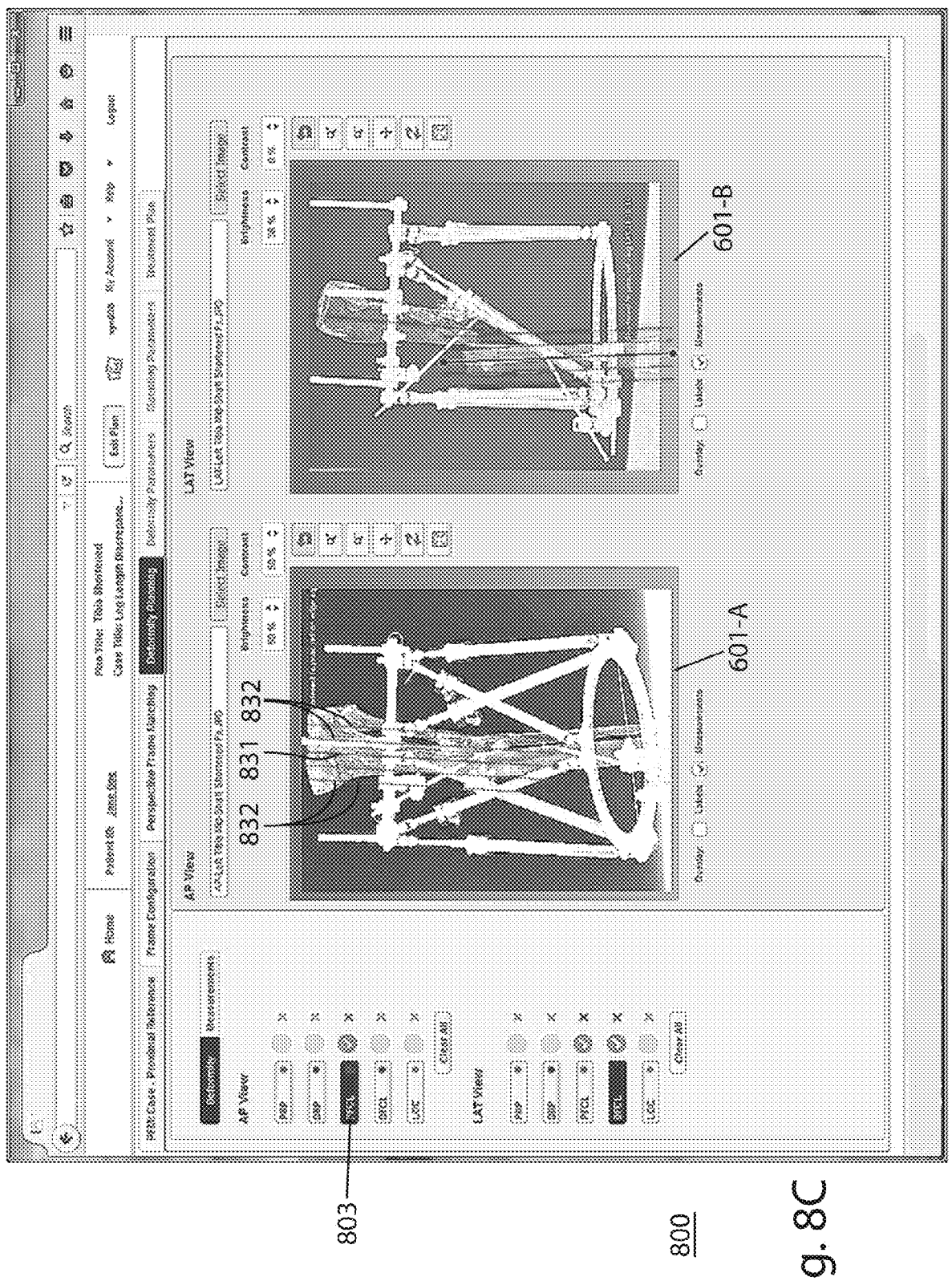
Figure 8D:
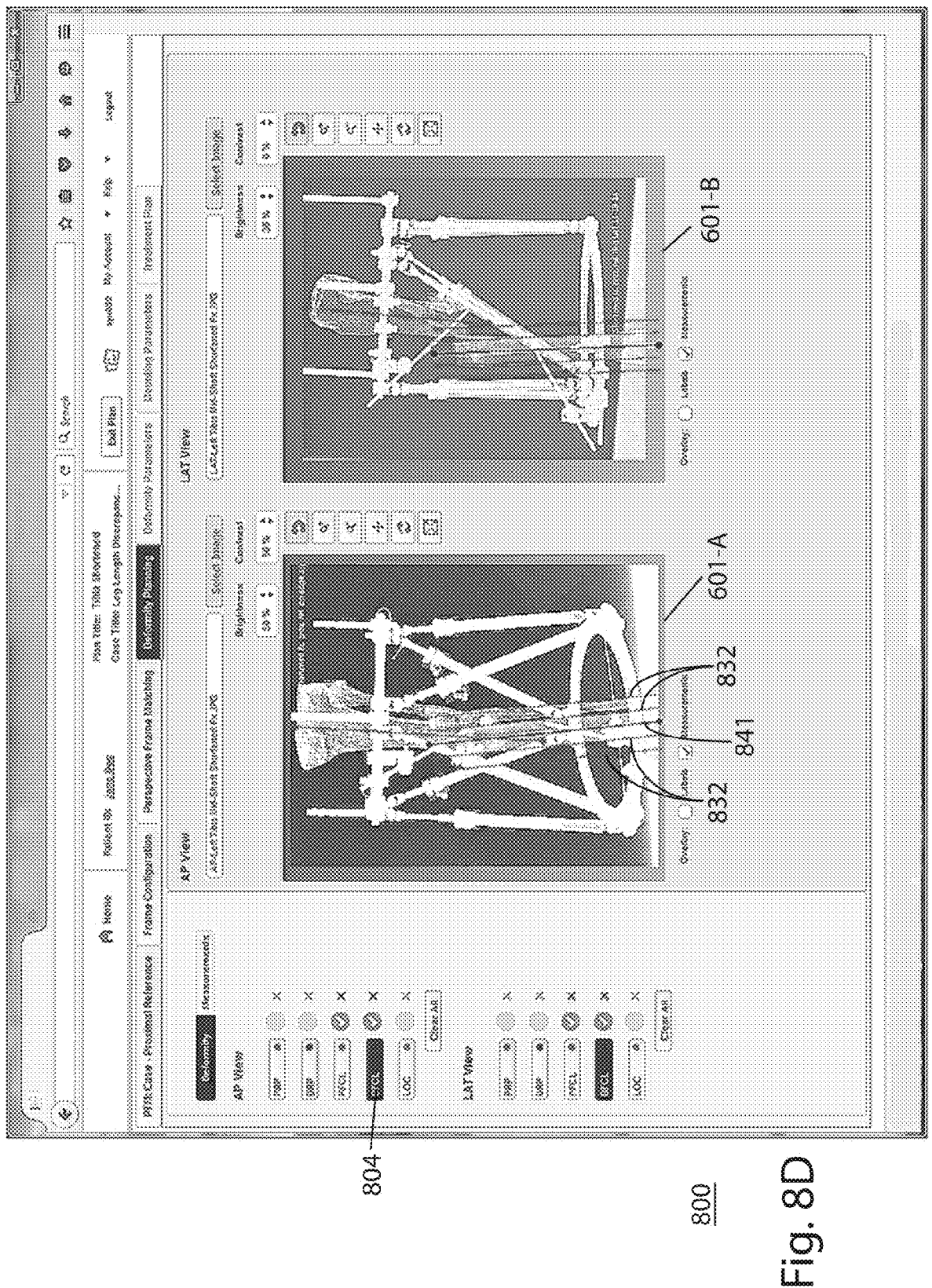

Referring now to FIG. 8A, an example second image information entry interface 800 is shown. As shown, interface 800 includes AP View image 601-A and LAT View image 601-B. Additionally, interface 800 includes buttons 801-808, which may be used to assist in indication of anatomical structure center lines and reference points as will be described below. In particular, buttons 801 and 805 may be selected to indicate a proximal anatomical structure reference point in the AP View and LAT View, respectively. Buttons 802 and 806 may be selected to indicate a distal anatomical structure reference point in the AP View and LAT View, respectively. Buttons 803 and 807 may be selected to indicate a proximal anatomical structure center line in the AP View and LAT View, respectively. Buttons 804 and 808 may be selected to indicate a distal anatomical structure center line in the AP View and LAT View, respectively. For example, as shown in FIG. 8A, a user may select button 807 and then use one or more input devices to draw the center line 831 for the proximal anatomical structure within LAT View image 601-B. In some examples, the center line 831 may be colored red. Additionally, two guidelines 832 are generated and displayed by the software on both sides of the red center line. In some examples, the guidelines 832 may be colored green. These guidelines 832 may be displayed while the user is drawing the center line 831 in order to assist the user in locating the center of the anatomical structure segment. The guidelines 832 may be generated at equal distances from each side of the center line 831 and may assist the user by, for example, potentially allowing the user to match (or nearly match) the guidelines 832 to sides of the anatomical structure segment. As shown in FIG. 8B, the user may select button 808 and then use one or more input devices to draw the center line 841 for the distal anatomical structure within LAT View image 601-B. As shown in FIG. 8C, the user may select button 803 and then use one or more input devices to draw the center line 851 for the proximal anatomical structure within AP View image 601-A. As shown in FIG. 8D, the user may select button 804 and then use one or more input devices to draw the center line 861 for the distal anatomical structure within AP View image 601-A. As shown in FIGS. 8B-8D, guidelines 832 may also be displayed for assistance in drawing center lines 841, 851 and 861.

Figure 8E:
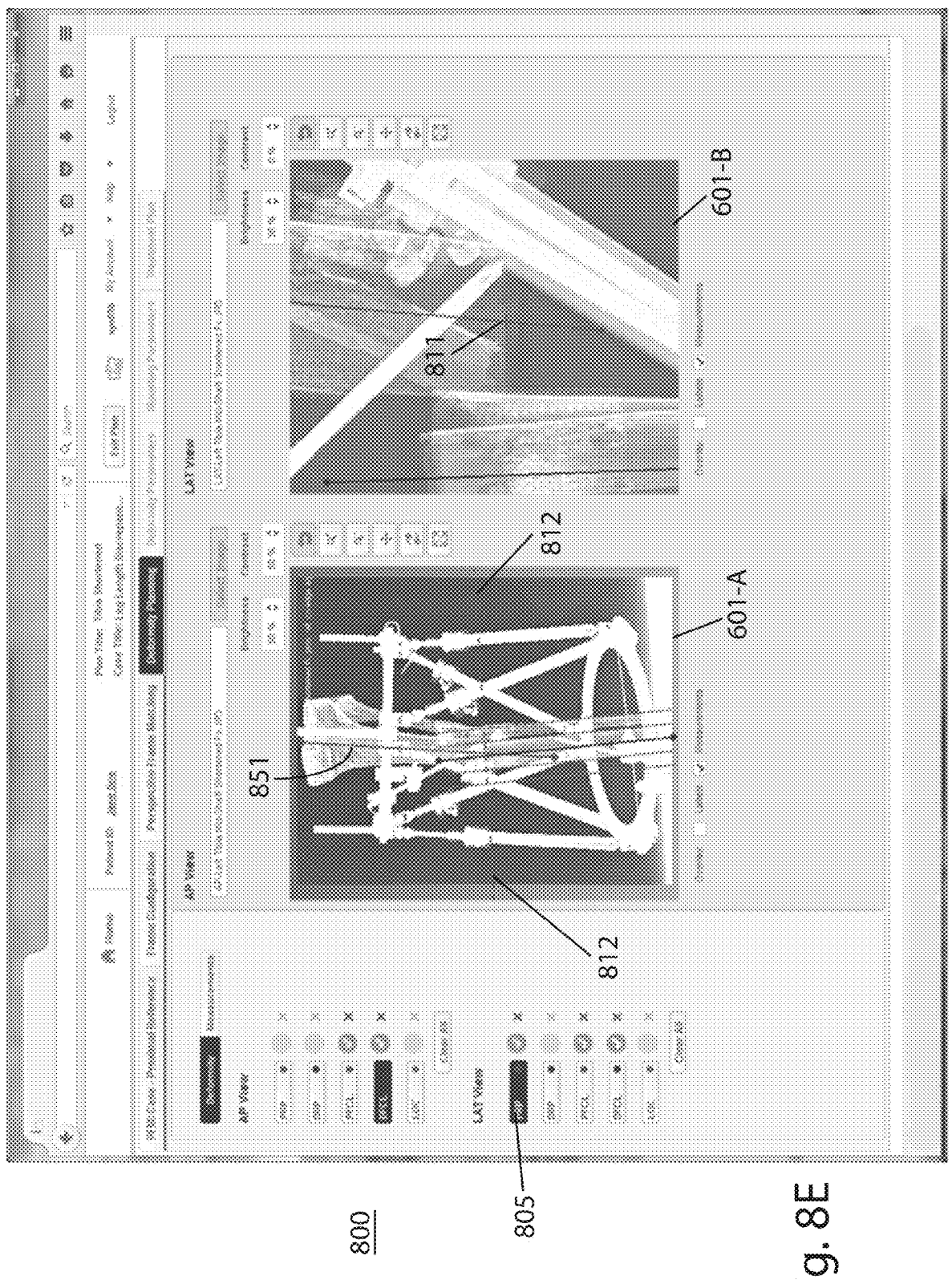

As shown in FIG. 8E, the user may select button 805 and then use one or more input devices to indicate a reference point (e.g., end point) for the proximal anatomical structure within LAT View image 601-B. As shown, a user has indicated a reference point 811 in LAT View image 601-B at an end point of the proximal anatomical structure segment.

Figure 8F:
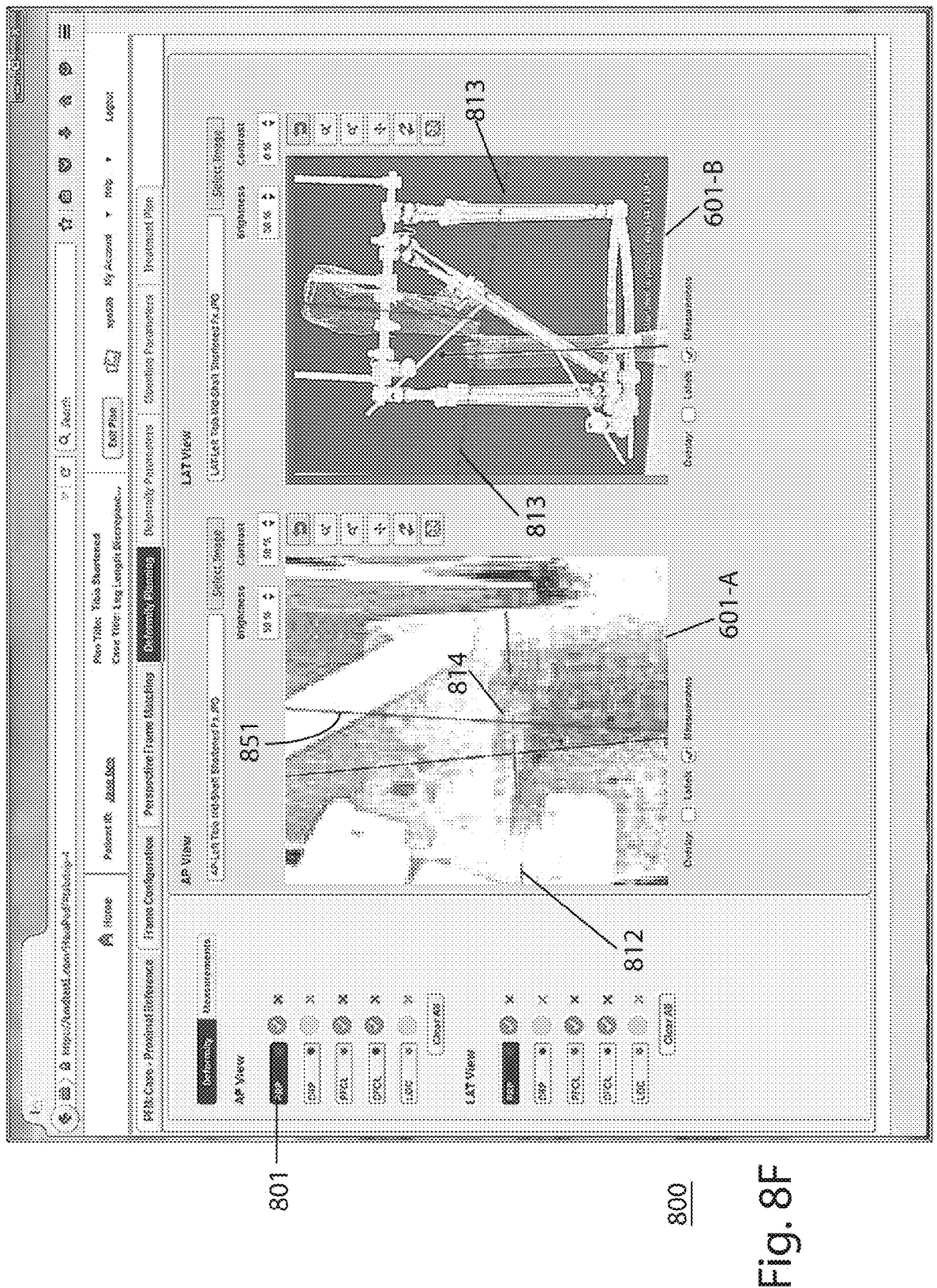

Additionally, upon indication of reference point 811, the software may generate and display a corresponding dashed reference line 812 in AP View image 601-A. The reference line 812 is a line drawn across AP View image 601-A that passes through the location of the LAT View proximal reference point 811 within AP View image 601-A. The reference line 812 may, therefore, assist the user in determining the location of the corresponding AP View proximal reference point, which may often be at the intersection of the reference line 812 and the AP View proximal center line 851 within the AP View image 601-A. As shown in FIG. 8F, the user may select button 801 and then use one or more input devices to indicate a reference point (e.g., end point) for the proximal anatomical structure within AP View image 601-A. In this example, the AP View proximal anatomical structure reference point 814 is indicated at the intersection of reference line 812 and the AP View proximal center line 851 within the AP View image 601-A. The software may then generate and display a corresponding dashed reference line 813 in the LAT View image 601-B. The reference line 813 is a line drawn across LAT View image 601-B that passes through the location of the AP View proximal reference point 814 within LAT View image 601-B. The reference line 813 may assist the user by helping the user to confirm that the AP View reference point 814 was placed correctly by showing how well it lines up relative to the LAT View reference point 811.

Figure 8G:
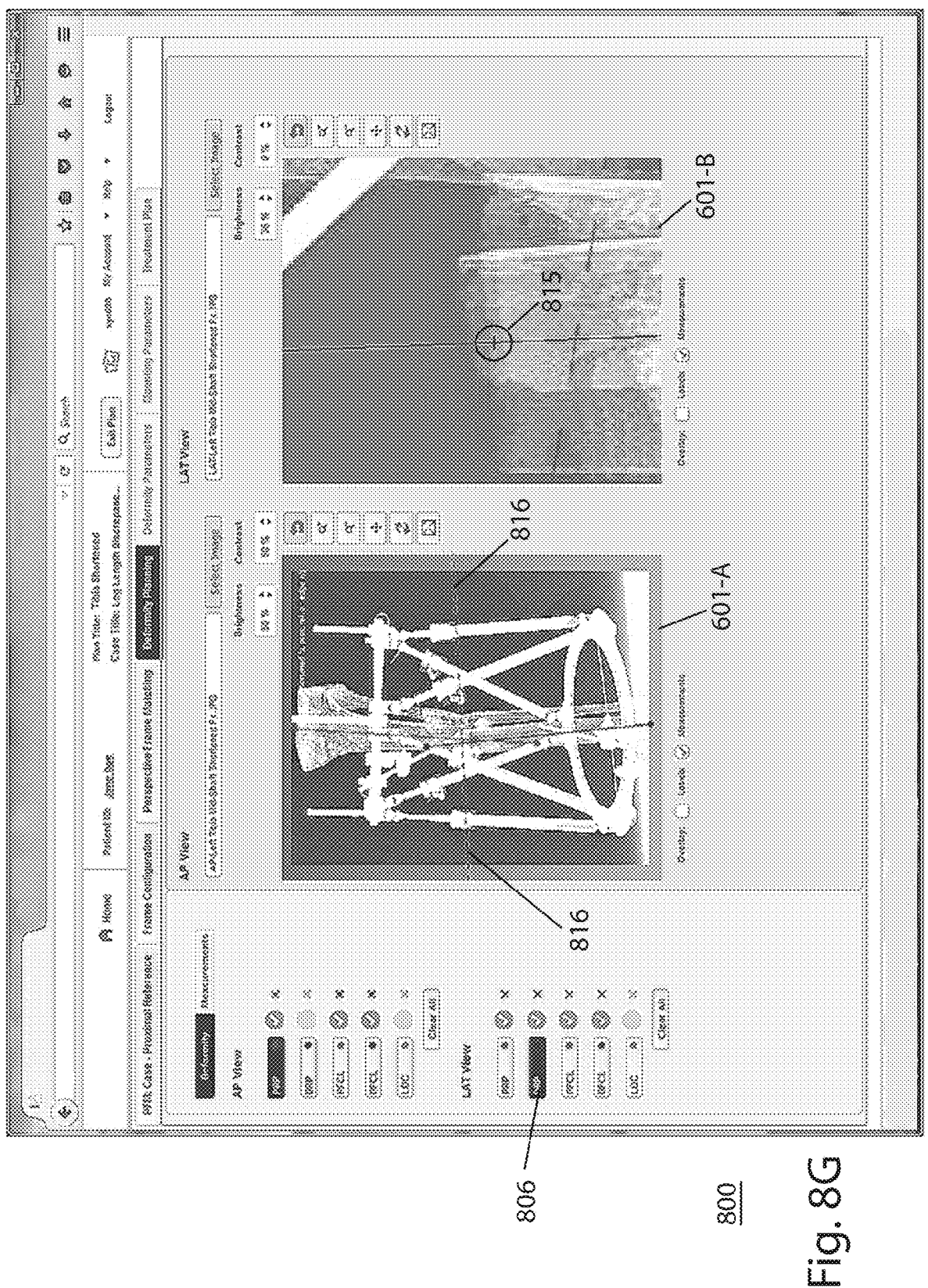
Figure 8H:
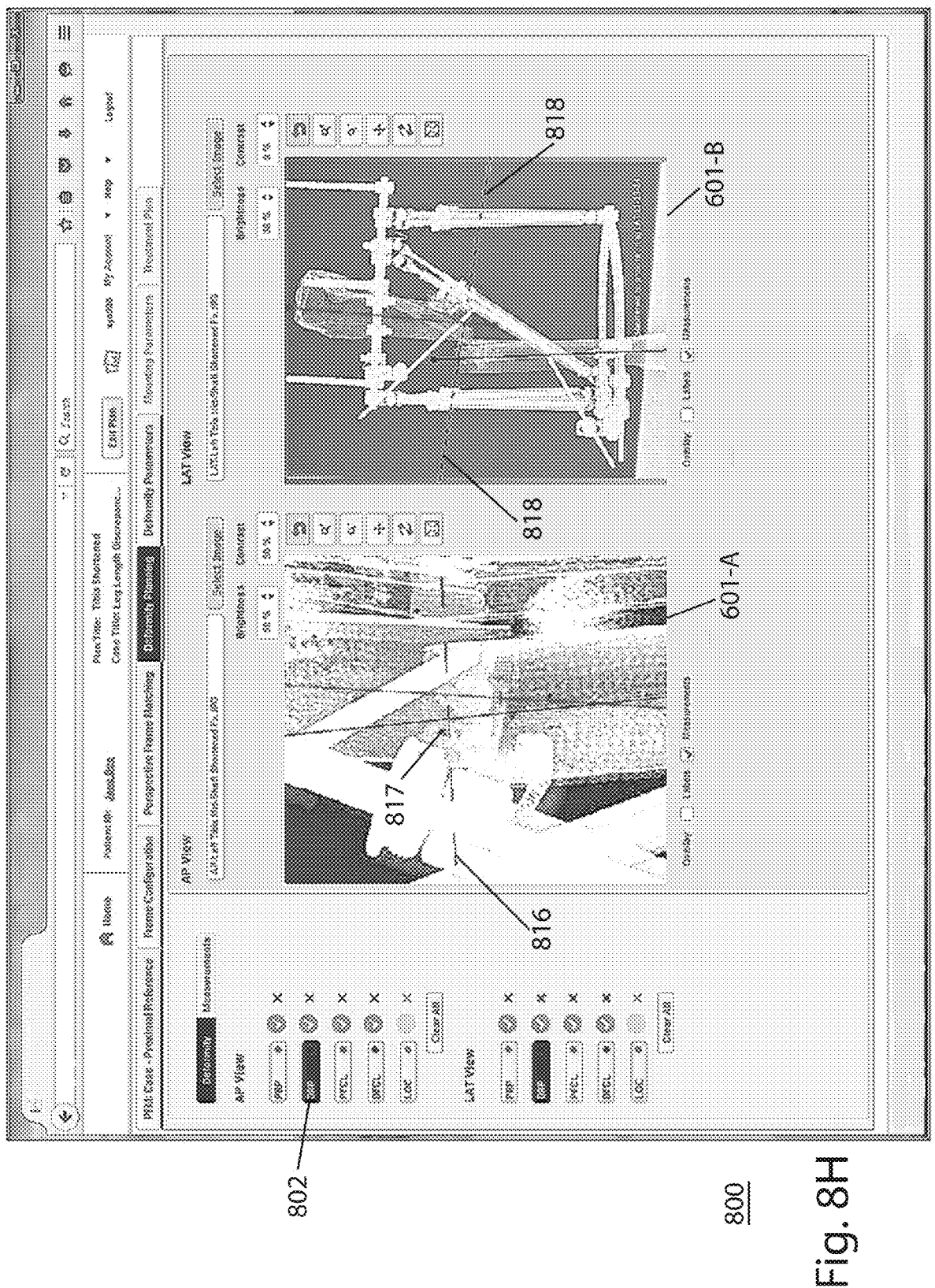

As shown in FIG. 8G, the user may select button 806 and then use one or more input devices to indicate a reference point (e.g., end point) for the distal anatomical structure within LAT View image 601-B. As shown, a user has indicated a reference point 815 in LAT View image 601-B at an end point of the distal anatomical structure segment. Additionally, upon indication of reference point 815, the software may generate and display a corresponding dashed reference line 816 in AP View image 601-A. The reference line 816 is a line drawn across AP View image 601-A that passes through the location of the LAT View distal reference point 815 within AP View image 601-A. The reference line 816 may, therefore, assist the user in determining the location of the corresponding AP View distal reference point, which may often be at the intersection of the reference line 816 and the AP View distal center line within the AP View image 601-A. As shown in FIG. 8H, the user may select button 802 and then use one or more input devices to indicate a reference point (e.g., end point) for the distal anatomical structure within AP View image 601-A. In this example, the AP View distal anatomical structure reference point 817 is indicated at the intersection of reference line 816 and the AP View distal center line within the AP View image 601-A. The software may then generate and display a corresponding dashed reference line 818 in the LAT View image 601-B. The reference line 818 is a line drawn across LAT View image 601-B that passes through the location of the AP View distal reference point 817 within LAT View image 601-B. The reference line 818 may assist the user by helping the user to confirm that the AP View reference point 817 was placed correctly by showing how well it lines up relative to the LAT View reference point 815.

Referring again to FIG. 3A, at operation 322, positions and orientations of the first and second anatomical structure segments and rings of the fixation apparatus are determined in three-dimensional space. For example, in some cases, imaging scene parameters pertaining to fixator 100, the anatomical structure segments 102, 104, imager(s) 130, and image capturing devices 127, 129 are obtained. The imaging scene parameters can be used in constructing a three dimensional representation of the positioning of the anatomical structure segments 102, 104 in the fixator 100, as described in more detail below. One or more of the imaging scene parameters may be known. Imaging scene parameters that are not known can be obtained, for example by mathematically comparing the locations of fixator element representations in the two dimensional space of the x-ray images 126, 128 to the three dimensional locations of those elements on the geometry of the fixator 100. In a preferred embodiment, imaging scene parameters can be calculated using a pin hole or perspective camera models. For example, the imaging scene parameters can be determined numerically using matrix algebra, as described in more detail below.

The imaging scene parameters can include, but are not limited to image pixel scale factors, image pixel aspect ratio, the image sensor skew factor, the image size, the focal length, the position and orientation of the imaging source, the position of the principle point (defined as the point in the plane of a respective image 126, 128 that is closest to the respective imager 130), positions and orientations of elements of the fixator 100, the position and orientation of a respective image receiver, and the position and orientation of the imaging source's lens.

In a preferred embodiment, at least some, such as all of the imaging scene parameters can be obtained by comparing the locations of representations of particular components, or fixator elements of the fixator 100 within the two dimensional spaces of the images 126, 128, with the corresponding locations of those same fixator elements in actual, three dimensional space. The fixator elements comprise components of the orthopedic fixator 100, and preferably are components that are easy to identify in the images 126, 128. Points, lines, conics, or the like, or any combination thereof can be used to describe the respective geometries of the fixator elements. For example, the representations of fixator elements used in the comparison could include center lines of one or more of the adjustable length struts 116, center points of the universal joints 124, center points of the mounting members 114, and the like.

The fixator elements can further include marker elements that are distinct from the above-described components of the fixator 100. The marker elements can be used in the comparison, as a supplement to or in lieu of using components of the fixator 100. The marker elements can be mounted to specific locations of components of the fixator 100 prior to imaging, can be imbedded within components of the fixator 100, or any combination thereof. The marker elements can be configured for enhanced viewability in the images 126, 128 when compared to the viewability of the other components of the fixator 100. For example, the marker elements may be constructed of a different material, such as a radio-opaque material, or may be constructed with geometries that readily distinguish them from other components of the fixator 100 in the images 126, 128. In an example embodiment, the marker elements can have designated geometries that correspond to their respective locations on the fixator 100.

Fixator elements can be identified for use in the comparison. For example, locations, within the images 126, 128 of fixator elements may be indicated using the first image information received at operation 318 and described in detail above. In some examples, the locations of the fixator elements in the two dimensional space of the images 126, 128 may be determined with respect to local origins 125 defined in the imaging planes of the images 126, 128. The local origins 125 serve as a "zero points" for determining the locations of the fixator elements in the images 126, 128. The locations of the fixator elements can be defined by their respective x and y coordinates with respect to a respective local origin 125. The location of the local origin 125 within the respective image can be arbitrary so long it is in the plane of the image. Typically, the origin is located at the center of the image or at a corner of the image, such as the lower left hand corner. It should be appreciated that the locations of the local origins are not limited to illustrated local origins 125, and that the local origins 125 can be alternatively defined at any other locations.

In some examples, a respective transformation matrix P may then be computed for each of the images 126, 128. The transformation matrices can be utilized to map location coordinates of one or more respective fixator elements in actual three dimensional space to corresponding location coordinates of the fixator element(s) in the two dimensional space of the respective image 126, 128. It should be appreciated that the same fixator element(s) need not be used in the comparisons of both images 126, 128. For example, a fixator element used in constructing the transformation matrix associated with image 126 can be the same or different from the fixator element used in constructing the transformation matrix associated with image 128. It should further be appreciated that increasing the number of fixator elements used in computing the transformation matrices can increase the accuracy method. The following equation represents this operation:

$$\begin{bmatrix} x \\ y \\ 1 \end{bmatrix} = P \cdot \begin{bmatrix} X \\ Y \\ Z \\ 1 \end{bmatrix} \qquad (1)$$

The symbols x and y represent location coordinates, with respect to the local origin 125, of a fixator element point in the two dimensional space of images 126, 128. The symbols X, Y and Z represent corresponding location coordinates, with respect to a space origin 135, of the fixator element point in actual three dimensional space. In the illustrated embodiment, the point corresponding to the center of the plane defined by the upper surface of the upper fixator ring 106 has been designated as the space origin 135. The illustrated matrix P can be at least four elements wide and three elements tall. In a preferred embodiment, the elements of the matrix P can be computed by solving the following matrix equation:

$$A \cdot p = B \qquad (2)$$

The vector p can contain eleven elements representing values of the matrix P. The following equations present arrangements of the elements in the vector p and the matrix P:

$$p = [\, p_1 \; p_2 \; p_3 \; p_4 \; p_5 \; p_6 \; p_7 \; p_8 \; p_9 \; p_{10} \; p_{11} \,]^T \qquad (3)$$

$$P = \begin{bmatrix} p_1 & p_2 & p_3 & p_4 \\ p_5 & p_6 & p_7 & p_8 \\ p_9 & p_{10} & p_{11} & p_{12} \end{bmatrix} \qquad (4)$$

In the preferred embodiment, the twelfth element $p_{12}$ of the matrix P can be set to a numerical value of one. The matrices A and B can be assembled using the two dimensional and three dimensional information of the fixator elements. For every point representing a respective fixator element, two rows of matrices A and B can be constructed. The following equation presents the values of the two rows added to the matrices A and B for every point of a fixator element (e.g., a center point of a respective universal joint 124):

$$\begin{bmatrix} \cdots & \cdots & \cdots & \cdots & \cdots & \cdots & \cdots & \cdots & \cdots & \cdots & \cdots \\ X & Y & Z & 1 & 0 & 0 & 0 & 0 & -x \cdot X & -x \cdot Y & -x \cdot Z \\ 0 & 0 & 0 & 0 & X & Y & Z & 1 & -y \cdot X & -y \cdot Y & -y \cdot Z \\ \cdots & \cdots & \cdots & \cdots & \cdots & \cdots & \cdots & \cdots & \cdots & \cdots & \cdots \end{bmatrix} \cdot p = \begin{bmatrix} \cdots \\ x \\ y \\ \cdots \end{bmatrix} \qquad (5)$$

The symbols X, Y and Z represent location coordinate values of a fixator element point in actual three dimensional space relative to the space origin 135, and the symbols x and y represent location coordinate values of the corresponding fixator element point in the two dimensional space of the respective image 126, 128 relative to local origin 125.

For every line representing a respective fixator element, two rows of matrices A and B can be constructed. The following equation presents the values of the two rows added to the matrices A and B for every line of a fixator element (e.g., a center line of a respective adjustable length strut 116):

$$\begin{bmatrix} \cdots & \cdots & \cdots & \cdots & \cdots & \cdots & \cdots & \cdots & \cdots & \cdots & \cdots \\ X \cdot a & Y \cdot a & Z \cdot a & a & X \cdot b & Y \cdot b & Z \cdot b & b & X \cdot c & Y \cdot c & Z \cdot c \\ dX \cdot a & dY \cdot a & dZ \cdot a & 0 & dX \cdot b & dY \cdot b & dZ \cdot b & 0 & dY \cdot c & dY \cdot c & dZ \cdot c \\ \cdots & \cdots & \cdots & \cdots & \cdots & \cdots & \cdots & \cdots & \cdots & \cdots & \cdots \end{bmatrix} \cdot p = \begin{bmatrix} \cdots \\ -c \\ 0 \\ \cdots \end{bmatrix} \qquad (6)$$

The symbols X, Y and Z represent location coordinate values of a point belonging to a line of a fixator element in actual three dimensional space relative to the space origin 135. The symbols dX, dY and dZ represent gradient values of the line in actual three dimensional space. The symbols a, b and c represent constants defining a line in the two dimensional space of a respective image 126, 128. For example, a, b, and c can be computed using two points belonging to a line on a respective image 126, 128. In a preferred embodiment, the value of b is assumed to be 1, unless the line is a vertical line, in which case the value of b is zero. A correlation of constants a, b and c with the respective image coordinates x and y is presented in the following equation:

$$a \cdot x + b \cdot y + c = 0 \qquad (7)$$

The equation (2) can be over constrained by using six or more fixator elements, for example the adjustable length struts 116. It should be appreciated that it is not necessary for all of the fixator elements to be visible in a single one of the images 126, 128 in order to obtain the matrix P. It should further be appreciated that if one or more of the above-described imaging scene parameters are known, the known parameters can be used to reduce the minimum number of the fixator elements required to constrain equation (2). For instance, such information could be obtained from modern imaging systems in DICOM image headers. Preferably, a singular value decomposition or least squares method can be used to solve equation (2) for values of the vectorp.

In some examples, the transformation matrices may then be decomposed into imaging scene parameters. The following equation can be used to relate the matrix P to matrices E and I:

$$P = I \cdot E \tag{8}$$

It should be appreciated that additional terms can be introduced when decomposing the matrix P. For example, the method presented by Tsai, described in "A Versatile Camera Calibration Technique for High-Accuracy 3D Machine Vision Metrology Using of-the-shelf TV Cameras and Lenses", IEEE Journal of Robotics & Automation, RA-3, No. 4, 323-344, August 1987, which is incorporated herein by reference in its entirety, can be used to correct images 126, 128, for radial distortion.

Matrices E and I contain imaging scene parameters. The following equation represents a composition of the matrix I:

$$I = \begin{bmatrix} sx & 0 & -tx \\ 0 & sy & -ty \\ 0 & 0 & 1/f \end{bmatrix} \tag{9}$$

The symbols sx and sy represent values of image coordinate scale factors (e.g., pixel scale factors). The symbol f, representing the focal length, corresponds to the value of the shortest distance between a respective imaging source 130 and the plane of a corresponding image 126, 128. The symbols tx and ty represent the coordinates of the principle point relative to the local origin 125 of the respective image 126, 128. The following equation represents the composition of the matrix E:

$$E = \begin{bmatrix} r_1 & r_2 & r_3 & -(r_1 \cdot o_x + r_2 \cdot o_y + r_3 \cdot o_z) \\ r_4 & r_5 & r_6 & -(r_4 \cdot o_x + r_5 \cdot o_y + r_6 \cdot o_z) \\ r_7 & r_8 & r_9 & -(r_7 \cdot o_x + r_8 \cdot o_y + r_9 \cdot o_z) \end{bmatrix} \tag{10}$$

The symbols $o_x$, $o_y$ and $o_z$ represent values of the position of the fixator 100 in actual three dimensional space. The symbols $r_1$ to $r_9$ describe the orientation of the fixator 100. These values can be assembled into a three dimensional rotational matrix R represented by the following equation:

$$R = \begin{bmatrix} r_1 & r_2 & r_3 \\ r_4 & r_5 & r_6 \\ r_7 & r_8 & r_9 \end{bmatrix} \tag{11}$$

The methods of Trucco and Verri, as described in "Introductory Techniques of 3-D Computer Vision", Prentice Hall, 1998, or the method of Hartley, as described in "Euclidian Reconstruction from Uncalibrated Views", Applications of Invariance in Computer Vision, pages 237-256, Springer Verlag, Berlin Heidelberg, 1994, which are incorporated herein in their entireties, can be used to obtain values of the matrices E and/or I. Utilizing the resulting values of matrices E and I, a complete three dimensional imaging scene of the fixator 100 and the anatomical structure segments 102, 104 can be reconstructed.

For example, FIG. 2 illustrates an example three dimensional imaging scene reconstructed from the x-ray images 126, 128. In the illustrated embodiment, x-rays are emitted from x-ray imagers 130. It should be appreciated that the x-ray imagers 130 can be the same or different imagers, as described above. The x-rays emitted from the imagers 130 are received on by corresponding imaging devices, thus capturing the images 126, 128. Preferably, the positioning of the imagers 130 with respect to the local origins 125 is known.

In some examples, the images 126, 128 and the imaging scene parameters may then be used to obtain the positions and/or orientations of the anatomical structure segments 102, 104 in three dimensional space. The position and/or orientation data obtained can be used to develop a treatment plan for a patient, for example to change the orientation and/or position of the fractured first and second anatomical structure segments 102, 104 in order to promote union between the anatomical structure segments 102, 104, as described in more detail below. It should be appreciated that the methods and techniques described herein are not limited to applications of repositioning broken anatomical structures, and that orthopedic fixation with imagery analysis can be used in any other type of fixation procedure as desired, for example lengthening of anatomical structures, correction of anatomical defects, and the like.

In some examples, anatomical structure elements comprising representations of particular portions (e.g., anatomical features) of the anatomical structure segments 102, 104, may then be identified and their locations within the images 126, 128 determined. For example, locations, within the images 126, 128 of the first and the second anatomical structure segments may be indicated using the second image information received at operation 320 and described in detail above. In some examples, the locations of the anatomical structure elements may be determined with respect to the respective local origins 125 of images 126, 128.

The anatomical structure elements can be used in the construction of the three dimensional representation of the position and/or orientation of the anatomical structure segments 102, 104. Preferably, the anatomical structure elements are easy to identify in the images 126, 128. Points, lines, conics, or the like, or any combination thereof can be used to describe the respective geometries of the anatomical structure elements. For example, in the illustrated embodiment, points 134 and 136 representing the fractured ends 103, 105 of the anatomical structure segments 102, 104, respectively, are identified as anatomical structure elements in the images 126, 128.

The anatomical structure elements can further include marker elements that are implanted into the anatomical structure segments 102, 104 prior to imaging. The marker elements can be used as a supplement to or in lieu of the above-described anatomical structure elements identified in the images 126, 128. The marker elements can be configured for enhanced viewability in the images 126, 128 when compared to the viewability of anatomical features of the anatomical structure segments 102, 104. For example, the marker elements may be constructed of a radio-opaque material, or may be constructed with readily distinguishable geometries.

A three dimensional representation 200 of the anatomical structure segments 102, 104 can be reconstructed. The three dimensional representation can be constructed with or without a corresponding representation of the fixator 100. In the illustrated embodiment, pairs of ray-lines, such as ray lines 138, 140 and 142, 144 can be constructed for the anatomical structure element points 134, 136, respectively. Each ray line connects an anatomical structure element in one of the images 126, 128 with a respective imager 130. Each pair of ray lines can be analyzed for a common intersection point, such as points 146, 148. The common intersection points 146, 148 represent the respective positions of the anatomical structure element points 134, 136, in the three dimensional representation of the anatomical structure segments 102, 104. Of course more than a pair of ray lines, such as a plurality, can be constructed, for example if more than two images were captured. If the ray lines of a particular set do not intersect, a point closest to all the ray lines in the set can be used as the common intersection point.

The positions and/or orientations of the anatomical structure segments 102, 104 can be quantified or measured using common intersection points, for instance points 146, 148. For example, lines representing center lines of the anatomical structure segments 102, 104 can be constructed and can be compared to the anatomical axes of the patient. Additionally, the distance between the fractured ends 103, 105 of the anatomical structure segments 102, 104 can be quantified. Using these or similar techniques, the positions and/or orientations of the anatomical structure segments 102, 104 can be determined. It is further noted that, in some examples, in addition to the positions and orientations of the first and second anatomical structure segments, the positions and orientation of rings (and/or other elements of the fixation apparatus) in three-dimensional space may also be determined, for example using any of the techniques described. For example, in some cases, locations of the rings within the images 126, 128 may be determined based on the first image information and/or other provided information. In some examples, these locations may then be used to determine the positions and orientations of the rings in three-dimensional space. Additionally, in some examples, configuration information for the fixation apparatus, such as ring diameters and strut length and mounting information, may also be used to determine positions and orientations of the rings in three-dimensional space.

Referring now to FIG. 3B, at operation 324, one or more deformity parameters are calculated. The deformity parameters may include parameters relating to the deformity associated with the first and second anatomical structure segments. For example, in some cases, the deformity parameters may include an amount of translation (e.g., lateral, medial, anterior, and/or posterior), a degree of coronal angulation (e.g., valgus and/or varus), a degree of sagittal angulation, an amount by which anatomical structure length is too short and/or too long, a degree of clinical rotational deformity (e.g., internal and/or external), and others. In some examples, the deformity parameters may be calculated as part of the process determining the positions and orientations of the first and segment anatomical structure segments described above at operation 422, for example using the techniques described above with reference to operation 422.

Figure 9:
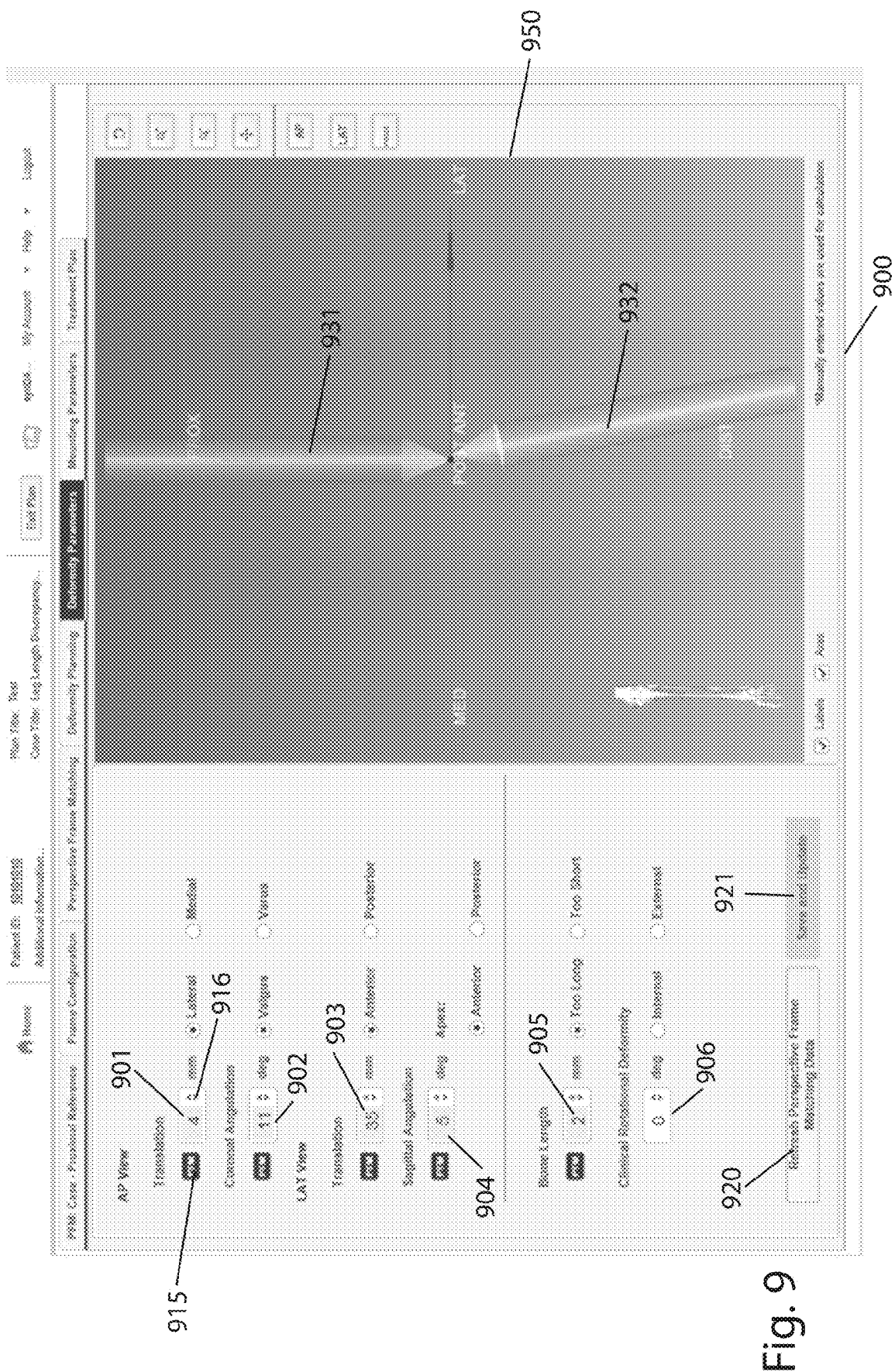
FIG. 9 is a screen shot of example deformity parameter interface for the PFM technique.

At operation 326, the deformity parameters calculated at operation 424 are displayed, for example using one or more graphical user interfaces of a computing system. Referring now to FIG. 9, a deformity parameter interface 900 is shown. As shown, interface 900 includes various fields 901-906 for displaying calculated values of various example deformity parameters, including AP View translation and coronal angulation, LAT View translation and sagittal angulation, an amount by which anatomical structure length is too short or too long, and a degree of clinical rotational deformity. In the example of FIG. 9, fields 901-905 each have a respective PFM badge 915 (including the text "PFM") that is displayed to the left of each field 901-905. Each PFM badge 915 indicates that the value shown in the respective field 901-905 has been calculated by the software. Interface 900 allows the deformity parameter values that are displayed in each field 901-906 to be edited by a user, for example by typing a number in the fields 901-906 and/or by using number increment controls 916 displayed to the right of each field 901-906. When a user edits a value that was calculated by the software, the PFM badge 915 adjacent to the respective field may be removed to indicate that the value for the field has been edited by the user. In some examples, after editing the values in one or more fields, the user may select Refresh Perspective Frame Matching Data button 920 to return each of the fields to the value that was calculated by the software. Also, in some examples, after editing the values in one or more fields, the user may select Save and Update button 921 to cause the deformity parameters to be recalculated based on the edited values provided by the user, for example by repeating all or any portion of the calculations performed at operation 322.

At operation 328, a graphical representation of the position and orientation of the first and the second anatomical structure segments is generated and displayed. The graphical representation of the position and orientation of the first and the second anatomical structure segments may be displayed using one or more graphical user interfaces of a computing system. For example, as shown in FIG. 9, interface 900 includes a graphical representation 950 of the position and orientation of the first and the second anatomical structure segments. Graphical representation 950 includes a representation 931 of the proximal anatomical structure segment and a representation 932 of the distal anatomical structure segment. In some examples, the graphical representation 950 may be generated based, at least in part, on the positions and orientations of the first and segment anatomical structure segments determined at operation 322. In some examples, when the user edits one or more deformity parameters and selects Save and Update button 921, the graphical representation 950 may also be adjusted to reflect the saved edits to the deformity parameters. Graphical representation 950 may, for example, improve efficiency and reliability by providing the user with a visual confirmation of information entered into interface 900, for example to allow fast and easy identification of errors or other problems.

At operation 330, one or more mounting parameters are calculated. The mounting parameters may include parameters relating to mounting of a reference ring of the fixator onto a respective anatomical structure segment. For example, in some cases, the mounting parameters may include an amount of offset (e.g., lateral, medial, anterior, and/or posterior) such as for a center of the reference ring with respect to a reference point, a degree of tilt (e.g., proximal and/or distal), an amount of axial offset, a master tab rotation, and others. In some examples, the mounting parameters may be calculated as part of the process determining the positions and orientations of the first and segment anatomical structure segments described above at operation 322, for example using the techniques described above with reference to operation 322. It is noted that, for the process of FIG. 3, the reference ring is not necessarily required to be orthogonal with respect to the respective anatomical structure segment on which it is mounted. Thus, in some examples, the reference ring may be non-orthogonal with respect to the respective anatomical structure segment on which it is mounted.

Figure 10:
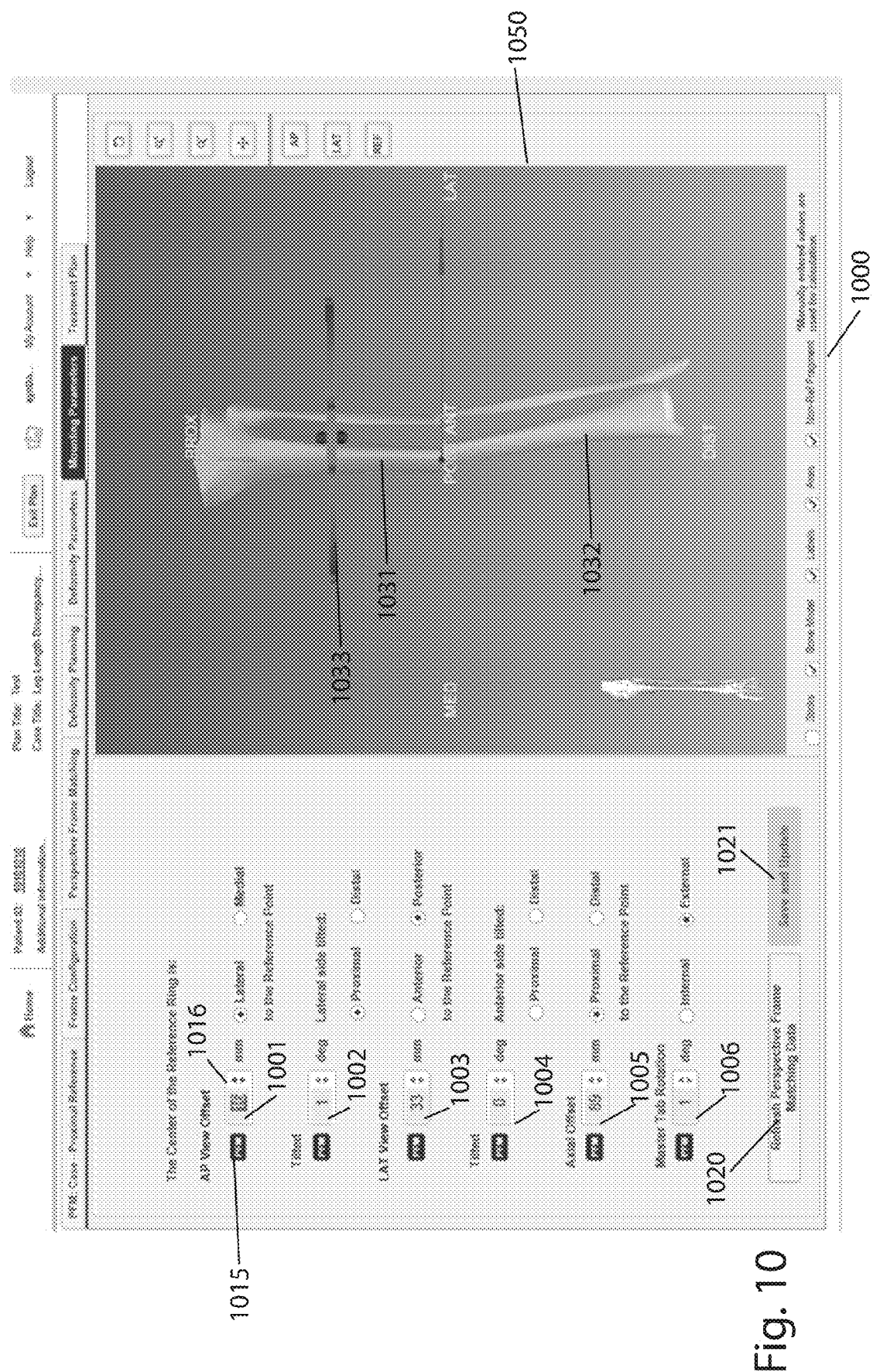
FIG. 10 is a screen shot of an example mounting parameter interface for the PFM technique.

At operation 432, the mounting parameters calculated at operation 430 are displayed, for example using one or more graphical user interfaces of a computing system. Referring now to FIG. 10, a mounting parameter interface 1000 is shown. As shown, interface 1000 includes various fields 1001-1006 for displaying calculated values of various example mounting parameters, including AP View offset and tilt, LAT View offset and tilt, axial offset, and master tab rotation. In the example of FIG. 10, fields 1001-1006 each have a respective PFM badge 1015 that is displayed to the left of each field 1001-1006. Each PFM badge 1015 indicates that the value shown in the respective field 1001-1006 has been calculated by the software. Interface 1000 allows the mounting parameter values that are displayed in each field 1001-1006 to be edited by a user, for example by typing a number in the fields 1001-1006 and/or by using number increment controls 1016 displayed to the right of each field 1001-1006. When a user edits a value that was calculated by the software, the PFM badge 1015 adjacent to the respective field may be removed to indicate that the value for the field has been edited by the user. In some examples, after editing the values in one or more fields, the user may select Refresh Perspective Frame Matching Data button 1020 to return each of the fields to the value that was calculated by the software. Also, in some examples, after editing the values in one or more fields, the user may select Save and Update button 1021 to cause the deformity parameters to be recalculated based on the edited values provided by the user, for example by repeating all or any portion of the calculations performed at operation 322.

At operation 334, a graphical representation of the position and orientation of the reference ring and the respective anatomical structure segment to which it is mounted is generated and displayed. The graphical representation of the position and orientation of the reference ring and the respective anatomical structure segment may be displayed using one or more graphical user interfaces of a computing system. For example, as shown in FIG. 10, interface 1000 includes a graphical representation 1050 of the position and orientation of the reference ring and the respective anatomical structure segment. Graphical representation 1050 includes a representation 1031 of the proximal anatomical structure segment, a representation 1033 of the proximal (reference) ring, and a representation 1032 of the distal anatomical structure segment. In some examples, the graphical representation 1050 may be generated based, at least in part, on the positions and orientations of the reference ring and the respective anatomical structure segment determined at operation 322. The graphical representation of the reference ring and the respective anatomical structure segment may, therefore, reflect and/or indicate the positions and orientations of reference ring and the respective anatomical structure segment determined at operation 322. In some examples, when the user edits one or more mounting parameters and selects Save and Update button 1021, the graphical representation 1050 may also be adjusted to reflect the saved edits to the mounting parameters. Graphical representation 1050 may, for example, improve efficiency and reliability by providing the user with a visual confirmation of information entered into interface 1000, for example to allow fast and easy identification of errors or other problems.

Figure 11:
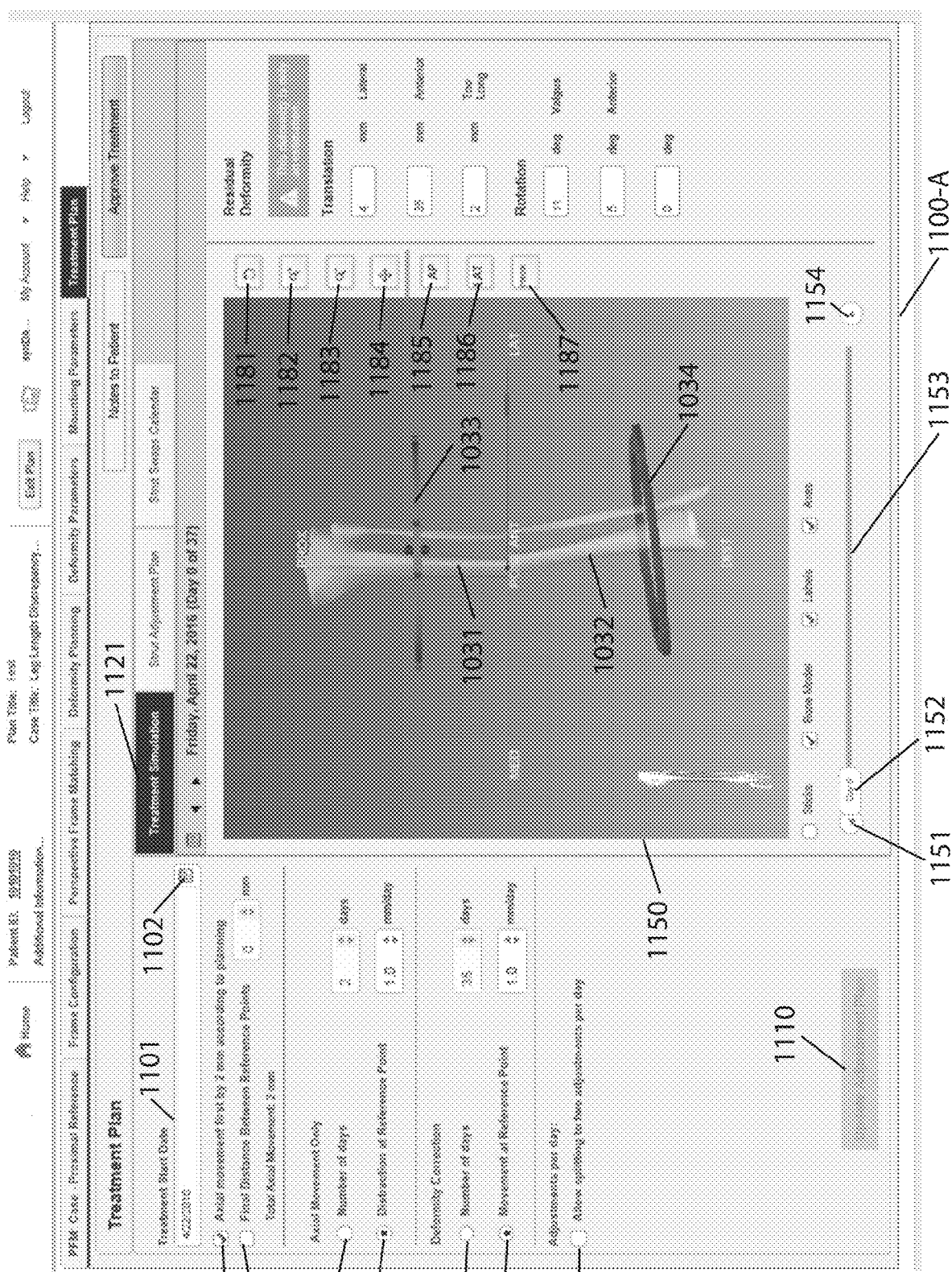
FIG. 11 is a screen shot of a first example treatment plan interface for the PFM technique.

At operation 336, one or more treatment plan options are received, for example using one or more graphical user interfaces of a computing system. A treatment plan is a plan for manipulating the fixation apparatus, for example in order to correct the deformity of the first and the second anatomical structure segments. The treatment plan may include, for example, a plan for making gradual adjustments to the positions and orientations of the fixator rings with respect to each other, for example by changing the lengths of the struts of the fixation apparatus. Referring now to FIG. 11, an example treatment plan interface 1100A is shown. The interface 1100A includes controls for selecting, by a user, various treatment plan options. In particular, controls 1101 and/or 1102 allow selecting of a treatment plan start date, control 1103 allows selection of an option to perform axial movement first (e.g., in an initial part of the treatment, such as prior to rotational movement), control 1104 allows selection of an option to indicate a final distance between reference points, control 1105 allows selection of an option to calculate the treatment plan based on a specified duration (e.g., a number of days) for axial movement, control 1106 allows selection of an option to calculate the treatment plan based on a rate of distraction at the reference point (e.g., for example millimeters (mm)/day) for axial movement, control 1108 allows selection of an option to calculate the treatment plan based on a specified duration (e.g., a number of days) for deformity correction, control 1109 allows selection of an option to calculate the treatment plan based on a rate of distraction at the reference point (e.g., for example millimeters (mm)/day) for deformity correction, and control 1107 allows selection of an option to perform two adjustments per day. In some examples, when control 1007 is not selected, a default option of one adjustment per day may be used. In some examples, after selecting desired treatment plan options, the user may select Update Adjustment Plan button 1110 to trigger generation of the treatment plan. Additionally, after initial generation of the treatment plan, the user may also be permitted to adjust the treatment plan options and have the treatment plan re-generated with the adjusted options by re-selecting Update Adjustment Plan button 1110

At operation 338, manipulations to the fixation apparatus for correction of the anatomical structure deformity (i.e., a treatment plan) are determined. The manipulations to the fixation apparatus may include adjustments to the struts of the fixation apparatus, such as adjustments to the sizes and/or lengths of the struts. In some examples, operation 338 may be performed based, at least in part, on the treatment plan options received at operation 336. For example, operation 338 may be performed based, at least in part, on specified start date, on instructions to perform axial movement first (e.g., in an initial part of the treatment, such as prior to rotational movement), a specified final distance between reference points, instructions to perform additional lengthening by a specified amount, instructions to generate an axial gap to ensure anatomical structure clearance, a specified duration (e.g., a number of days) of treatment, a specified rate of distraction, and/or instructions to perform two perform a specified quantity (e.g., one, two, etc.) of adjustments per day.

In some examples, the treatment plan may also be determined based, at least in part, on a determination of desired changes to the positions and/or orientations of the anatomical structure segments 102, 104, for instance how the anatomical structure segments 102, 104 can be repositioned with respect to each other in order to promote union between the anatomical structure segments 102, 104. For example, in some cases, it may be desirable to change the angulation of the second anatomical structure segment 104 such that the axes L1 and L2 are brought into alignment, and to change the position of the second anatomical structure segment such that the fractured ends 103, 105 of the anatomical structure segments 102, 104 abut each other. Once the desired changes to the positions and/or orientations of the anatomical structure segments 102, 104 have been determined, a treatment plan for effecting the position and/or orientation changes can be determined. In a preferred embodiment, the desired changes to the positions and/or orientations of the anatomical structure segments 102, 104 can be effected gradually, in a series of smaller changes. The positions and/or orientations of the anatomical structure segments 102, 104 can be changed by changing the positions and/or orientations of the upper and lower fixator rings 106, 108 with respect to each other, for instance by lengthening or shortening one or more of the length adjustable struts 116.

The required changes to the geometry of the fixator 100 (i.e., the position and/or orientation of the fixator 100) that can enable the desired changes to the positions and/or orientations of the anatomical structure segments 102, 104 can be computed using the matrix algebra described above. For example, the required repositioning and/or reorientation of the second anatomical structure segment 104 with respect to the first anatomical structure segment 102 can be translated to changes in the position and/or orientation of the lower fixator ring 108 with respect to the upper fixator ring 106.

Figure 12:
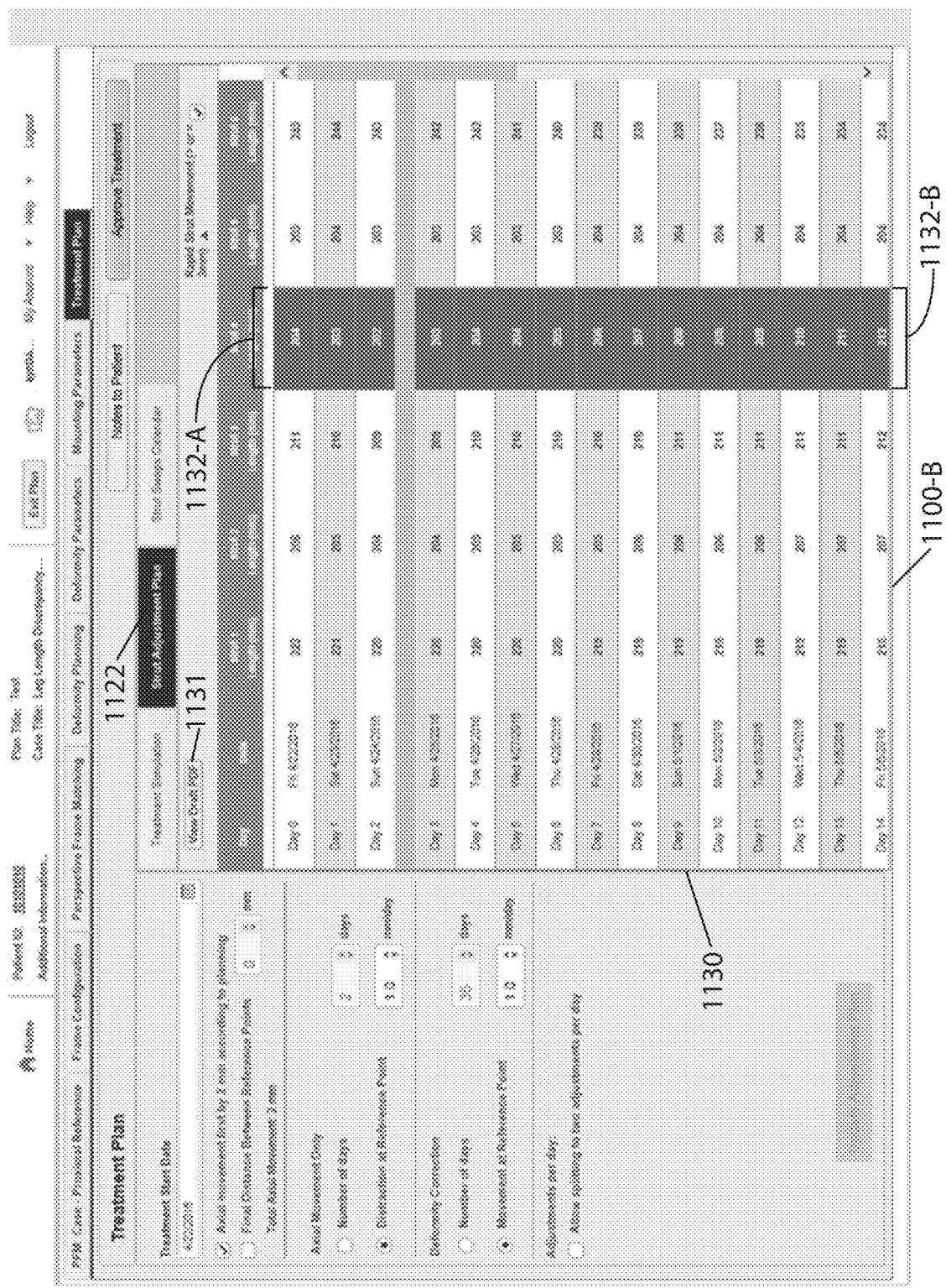
FIG. 12 is a screen shot of a second example treatment plan interface for the PFM technique.

At operation 340, indications of the determined manipulations to the fixation apparatus are provided to one or more users. For example, in some cases, indications of the determined manipulations to the fixation apparatus may be provided using one or more graphical user interfaces of a computing system, using a printed hard copy, using audio feedback, and/or using other techniques. In particular, referring now to FIG. 12, it is seen that indications of the determined manipulations to the fixation apparatus may be provided within interface 1100B. Specifically, selection of Strut Adjustment Plan tab 1122 may cause treatment plan interface 1100B to provide a chart 1130, including day-by-day manipulation information for each strut within the fixation apparatus. In this example, chart 1130 shows a length for each strut on each day of treatment. In some examples, one or more alerts may be generated for one or more manipulations to the fixation apparatus that result in at least one of strut movement of more than a threshold amount. For example, in some cases, strut movements exceeding particular threshold amount (e.g., 3 mm per day), which may be referred to as rapid strut movements, may be indicated by displaying a red triangle icon next to the indication of the strut movement in chart 1130. As also shown in FIG. 12, a PDF version of the chart 1130 may be generated by selecting View Draft PDF button 1131. The generated PDF may, in some examples, be printed to create a hard copy version of chart 1130.

Figure 13:
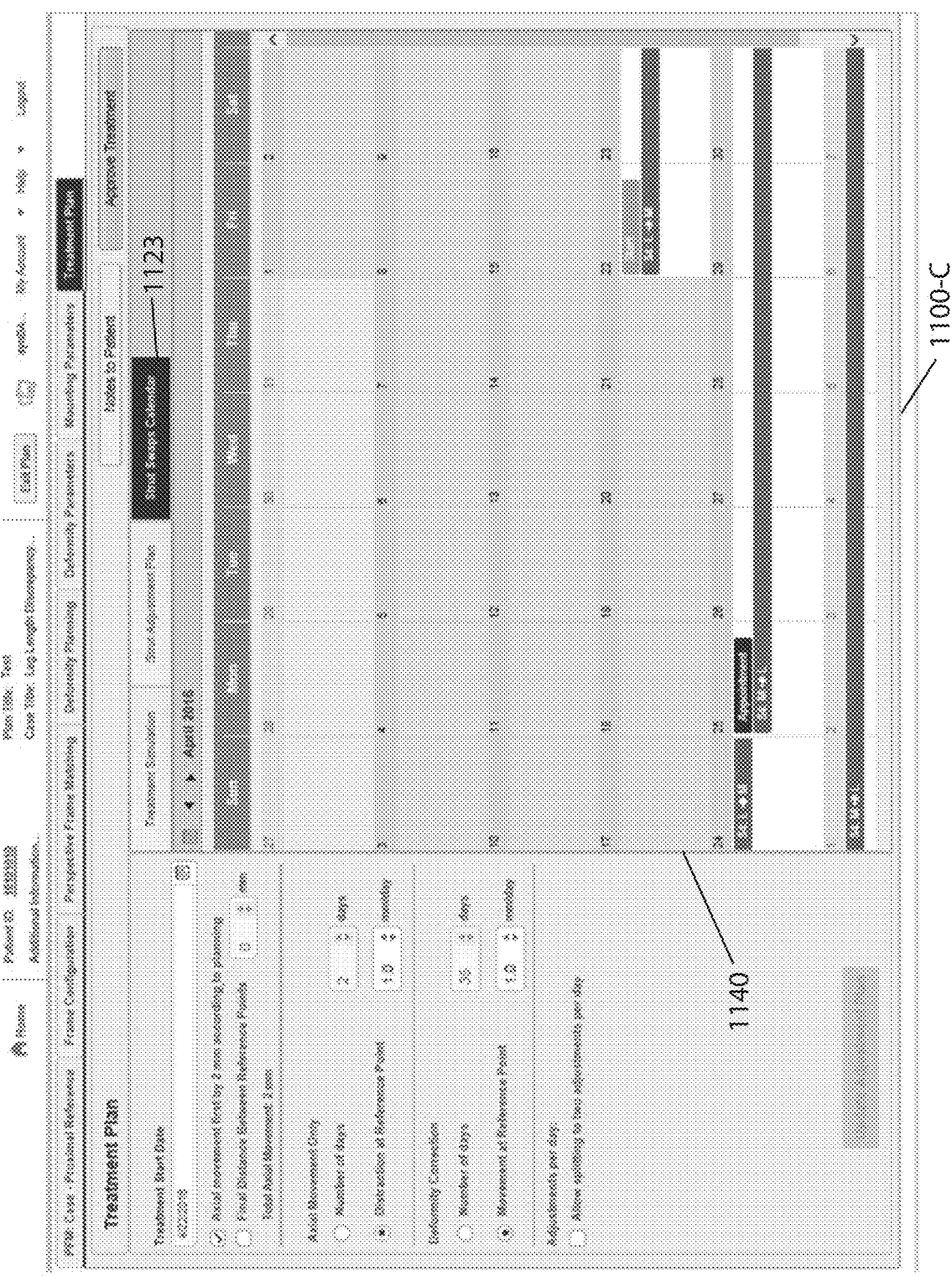
FIG. 13 is a screen shot of a third example treatment plan interface for the PFM technique.

In the example of FIG. 12, chart 1130 includes blocks 1132-A and 1132-B indicating ranges of dates on which changes of strut sizes, referred to as strut swaps, may be performed. In particular, block 1132-A indicates that a strut swap may be performed for Strut 4 on Day 0 through Day 2, while block 1132-B indicates that a strut swap may be performed for Strut 4 on Day 3 through Day 14 (and subsequent days). In some examples, blocks 1132-A and 1132-B may be color-coded to match a color assigned to a respective strut. For example, blocks 1132-A and 1132-B may be colored green to match a green color that may be assigned to Strut 4. Referring now to FIG. 13, Strut Swaps Calendar tab 1123 of treatment plan interface 1100-C may be selected to generate a calendar 1140 indicating ranges of dates on which strut swaps may be performed.

In some examples, the struts of the fixation apparatus attached to the patient may be color-coded, for example using color-coded caps, marker, or other color-coded materials included within and/or attached to the struts. In some examples, the physical color-coding of the struts in the fixation apparatus attached to the patient may match the color-coding of struts used in the software. For example, the physical color-coding of the struts in the fixation apparatus may match the color-coding of struts that may be used to color-code the blocks 1132-A and 1132-B of chart 1130, graphical representation 520, and other color-coded representations of the struts displayed by the software. In some examples, this may make it easier for physicians and/or patients to confirm that, when they physically adjust a strut on the fixation apparatus, they are adjusting the correct strut by the correct amount.

At operation 342, one or more graphical representations of the position and orientation of the first and second anatomical structure segments and the rings of the fixation apparatus is generated and displayed. The graphical representation of the position and orientation of the first and the second anatomical structure segments and the rings of the fixation apparatus may be displayed using one or more graphical user interfaces of a computing system. For example, referring back to FIG. 11, selection of Treatment Simulation tab 1121 may cause interface 1100 to display a graphical representation 1150 of the position and orientation of the first and the second anatomical structure segments and the rings of the fixation apparatus. Graphical representation 1150 includes a representation 1031 of the proximal anatomical structure segment, a representation 1033 of the proximal (reference) ring, a representation 1032 of the distal anatomical structure segment, and a representation 1034 of the distal ring. In some examples, the one or more graphical representations of the position and orientation of the first and second anatomical structure segments and the rings of the fixation apparatus may include day-by-day graphical representations of the position and orientation of the first and second anatomical structure segments and the rings of the fixation apparatus throughout treatment for the anatomical structure deformity. For example, as shown in FIG. 11, a user may select a particular day of treatment for which to generate and display a graphical representation 1150 using controls 1151, 1152, 1153, and/or 1154. For example, control 1151 may be selected to allow incrementing of the selected day, control 1154 may be selected to allow decrementing of the selected day, and slider 1152 may be slid along bar 1153 to increment and/or decrement the selected day. It is also noted that slider 1152 displays an indication of the currently selected day, which, in the example of FIG. 11, is treatment day zero. Thus, in FIG. 11, graphical representation 1150 shows the position and orientation of the first and second anatomical structure segments and the rings of the fixation apparatus at treatment day zero. Using controls 1151-1154 to select a different day of treatment may cause graphical representation 1150 to be adjusted to show the position and orientation of the first and second anatomical structure segments and the rings of the fixation apparatus on the selected different day. As should be appreciated, allowing the surgeon and/or patient to see graphical representations of the position and orientation of the first and second anatomical structure segments and the rings of the fixation apparatus throughout treatment may be beneficial by, for example, providing an additional visual tool to improve accuracy and assist in planning of treatment. Additionally, graphical representation 1150 (as well as graphical representations described herein) may, for example, improve efficiency and reliability by providing the user with a visual confirmation of information entered into interface 1100, for example to allow fast and easy identification of errors or other problems. It is further noted that the view of graphical representation 1150 (as well as other graphical representations described herein) may be rotated (for example by a complete 360 degrees), zoomed in and out, moved in direction, and otherwise manipulated, for example using controls 1181-1184 adjacent to the upper right side of the graphical representation 1150. This may allow views of the first and second anatomical structure segments and/or the rings of the fixation apparatus from various orientations that may not be available, or may be difficult to obtain, using x-rays and other imaging techniques, thereby also improving reliability and accuracy and providing additional visual confirmation of calculated values. In particular, view of the graphical representation 1150 may be rotated using control 1181, zoomed in using control 1182, zoomed out using control 1183, and panned using control 1184. Also, in some examples, other controls, such as a mouse and touchscreen, may also be employed to rotate, zoom, pan, and otherwise manipulate graphical representation 1150. Additionally, in some examples, control 1185 may be used to select an anteroposterior (AP) view, control 1186 may be used to select a lateral view, and control 1187 may be used to select a proximal view.

At operation 344, the treatment plan may be implemented, that is the geometry of the fixation apparatus may be changed, for example based on the manipulations determined at operation 338, in order to change positions and orientations of the anatomical structure segments, which may be performed for example for any or all of the PFM, Standard, and/or AID techniques.

Figure 14:
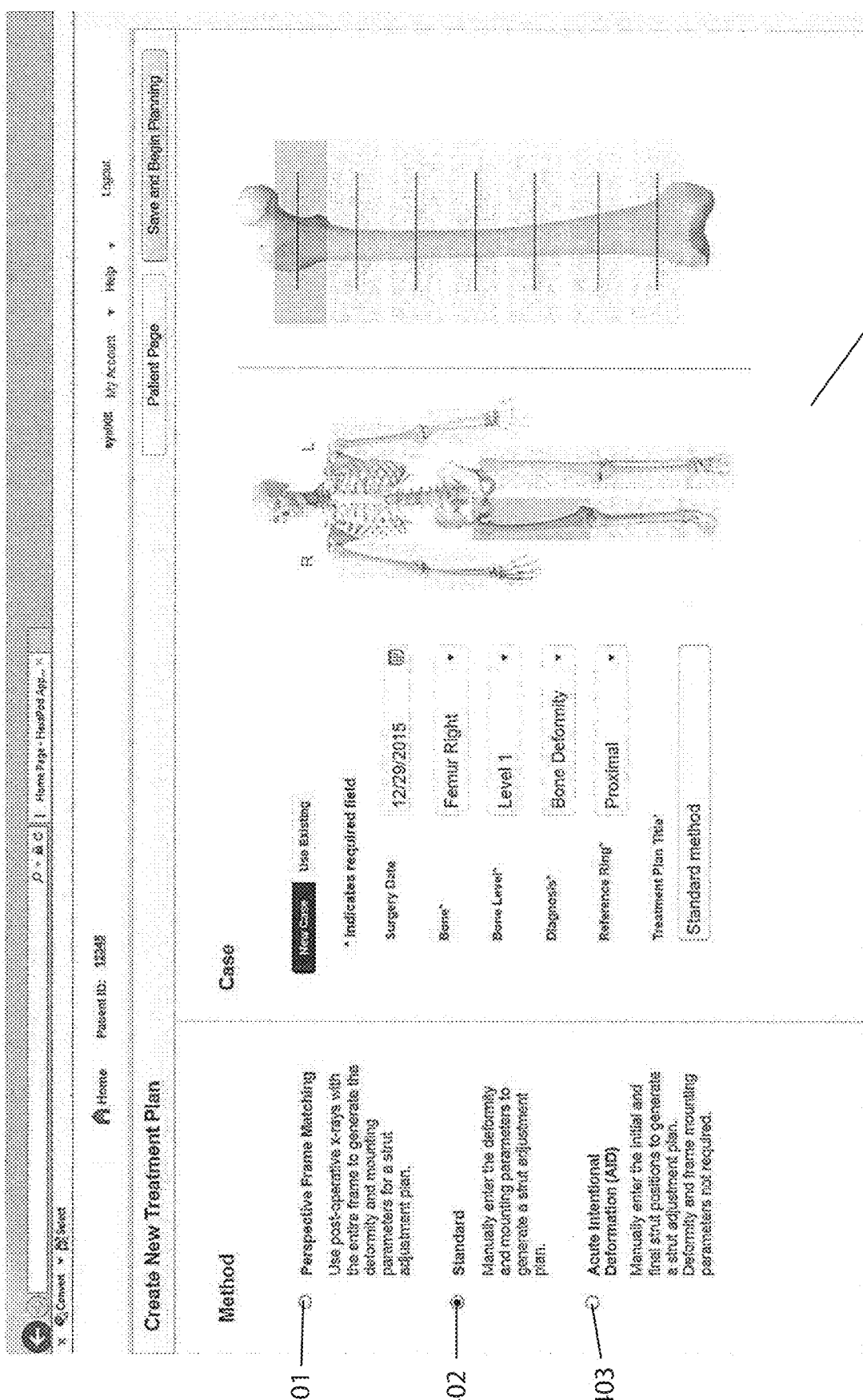
FIG. 14 is a screen shot of an example interface for selecting a Standard technique.

Thus, some examples of the Perspective Frame Matching (PFM) technique have been described in detail above with reference to FIGS. 4-13. In some examples, however, it may be advantageous for users to employ a different technique in which deformity and mounting parameters are entered manually to generate a strut adjustment plan. This technique is referred to hereinafter as the Standard technique. In particular, referring now to FIG. 14, a treatment planning technique selection interface 400-B is shown. In the example of FIG. 14, the user has selected option 402 to use the Standard technique, which will now be described in detail with reference to FIGS. 15-20.

Figure 15:
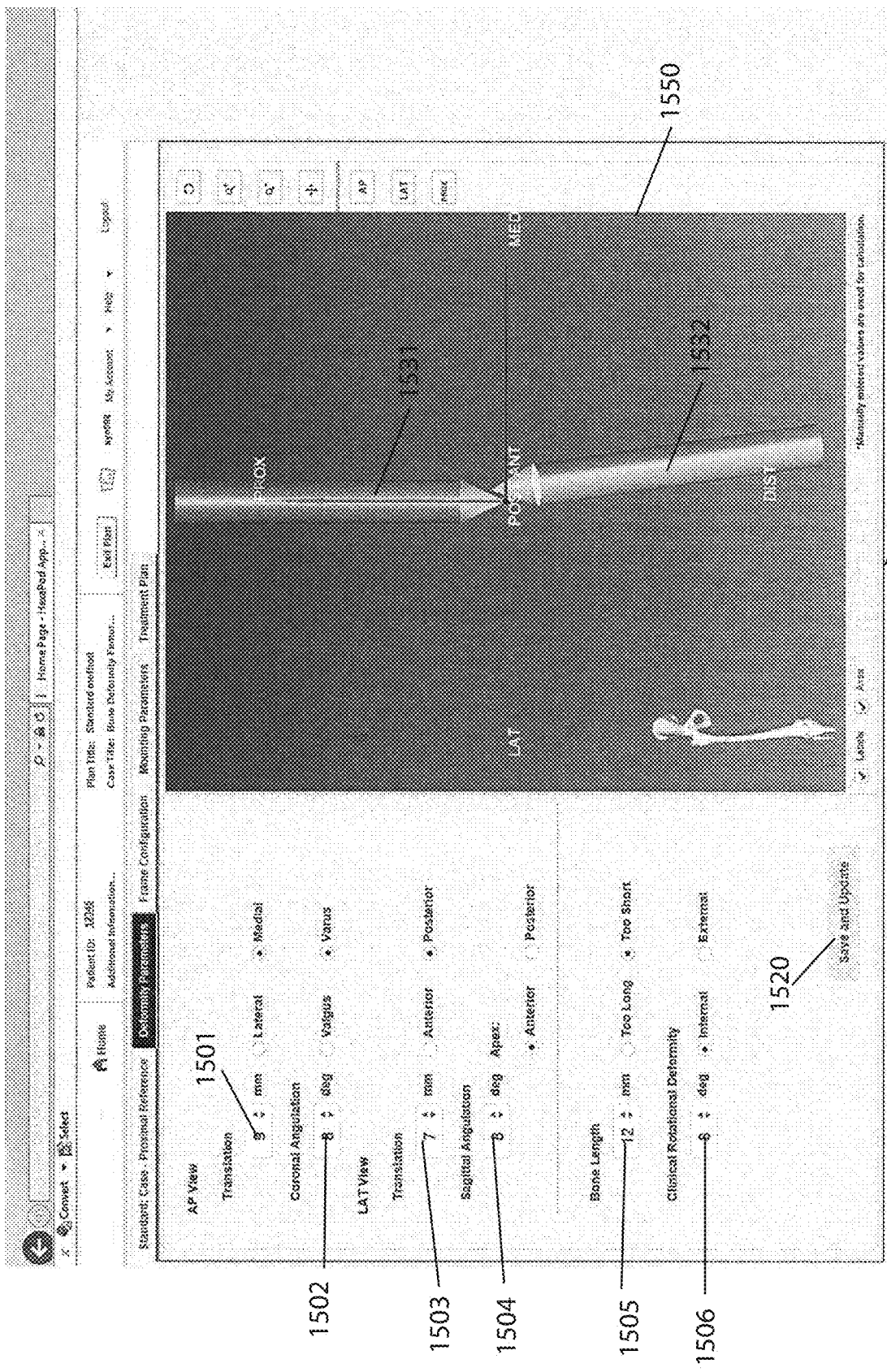
FIG. 15 is a screen shot of an example deformity parameter interface for the Standard technique.

Referring now to FIG. 15, after selecting the Standard technique, a deformity parameter interface 1500 is shown. It is noted that deformity parameter interface 1500 of FIG. 15 for the Standard technique includes many similarities to deformity parameter interface 900 of FIG. 9 for the PFM Technique described above. For example, similar to interface 900, interface 1500 includes various fields 1501-1506 for entering values of various example deformity parameters, including AP View translation and coronal angulation, LAT View translation and sagittal angulation, an amount by which anatomical structure length is too short or too long, and a degree of clinical rotational deformity. It is noted, however, that, in the Standard technique, the values shown in fields 1501-1506 are determined and entered manually by the user (as opposed to being calculated by software). Thus, the PFM badges 915 of interface 900, which indicate values calculated by software, are not included in interface 1500. In some examples, when using the Standard technique, the values entered into fields 1501-1506 may be determined by a surgeon, for example based on an analysis of first and second images of the first and second anatomical structure segments with the fixation apparatus attached thereto. Also, in some examples, when using the Standard technique, it may be required for the first and the second images to be orthogonal with respect to one another in order to allow the surgeon to calculate the values for fields 1501-1506. This differs from the PFM technique described above with reference to FIGS. 4-13, in which the first and second images of the first and second anatomical structure segments with the fixation apparatus attached thereto need not necessarily be orthogonal to one another.

Similar to interface 900, interface 1500 also includes a graphical representation 1550 of the position and orientation of the first and the second anatomical structure segments. Graphical representation 1550 includes a representation 1531 of the proximal anatomical structure segment and a representation 1532 of the distal anatomical structure segment. Graphical representation 1550 may be adjusted based on the values entered into fields 1501-1506. For example, a user may enter values into fields 1501-1506 and then select Save and Update button 1521, which may cause graphical representation 1550 to be adjusted based on the values entered into fields 1501-1506.

Figure 16:
FIG. 16 is a screen shot of an example configuration information entry interface for the Standard technique.

Referring now to FIG. 16, after entering the deformity parameters, a configuration information entry interface 1600 may be displayed for entering configuration information associated with the fixation apparatus. It is noted that interface 1600 of FIG. 16 includes features that substantially correspond to those of interface 500 of FIG. 5. These corresponding features are described in detail above with reference to FIG. 5 and are not repeated here.

Figure 17:
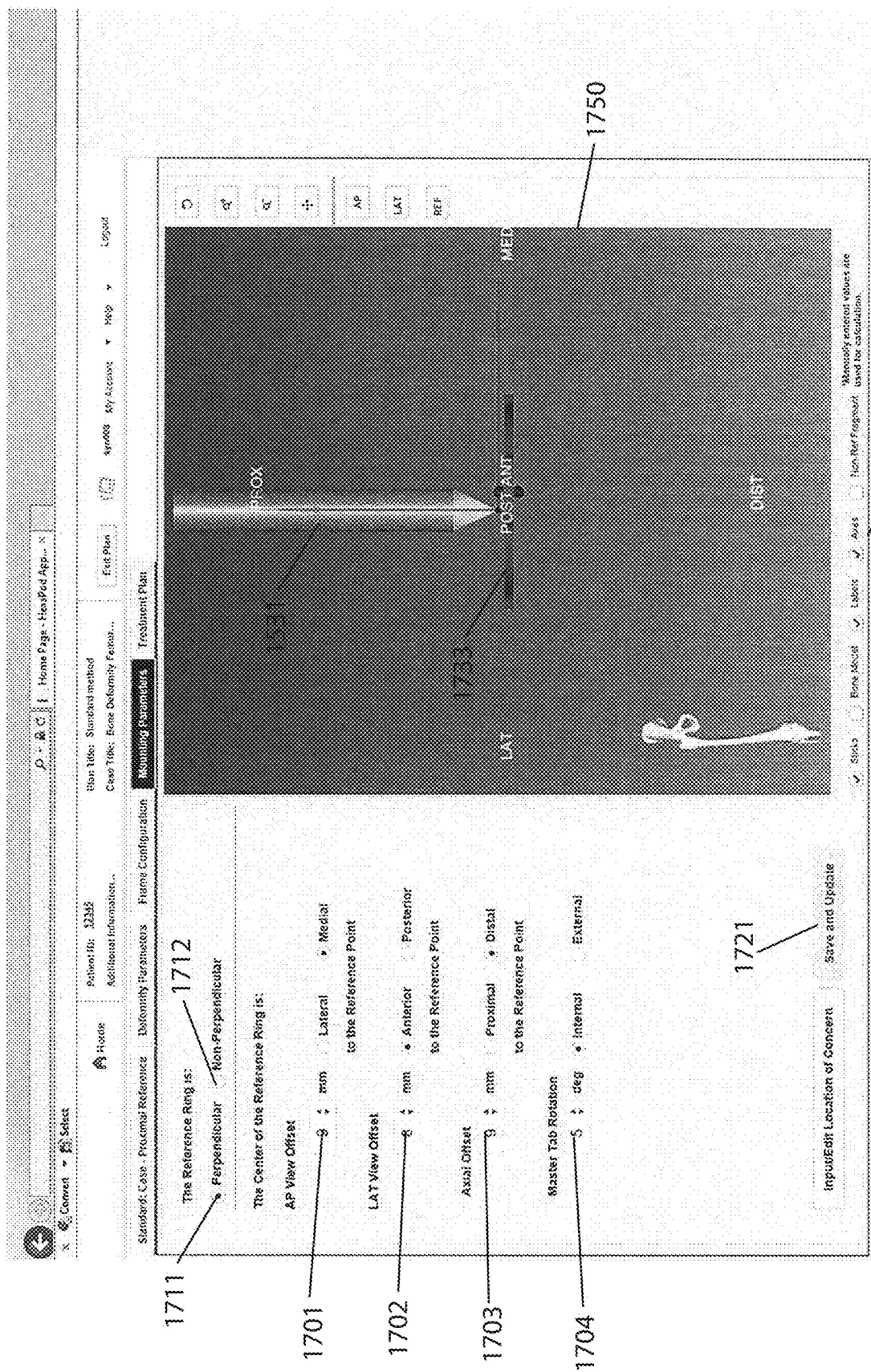
FIG. 17 is a screen shot of an example mounting parameter interface for the Standard technique.
Figure 20:
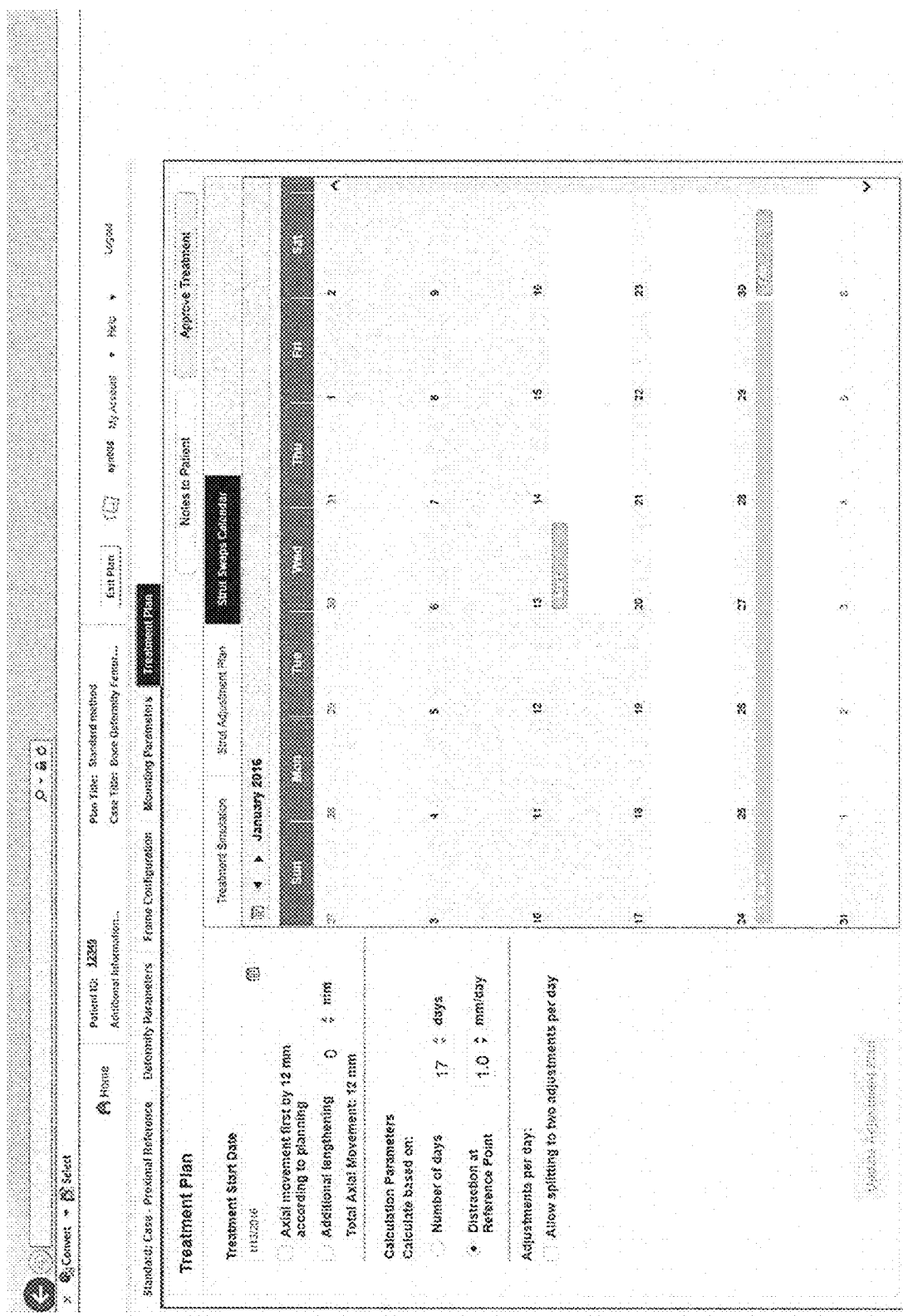
FIG. 20 is a screen shot of a third example treatment plan interface for the Standard technique.

Referring now to FIG. 17, after entering the configuration information, a mounting parameter interface 1700 is shown. It is noted that mounting parameter interface 1700 of FIG. 17 for the Standard technique includes many similarities to mounting parameter interface 1000 of FIG. 10 for the PFM Technique described above. For example, similar to interface 1000, interface 1700 includes various fields 1701-1704 for entering values of various example mounting parameters, including AP View offset, LAT View offset, axial offset, and master tab rotation. It is noted, however, that, in the Standard technique, the values shown in fields 1701-1704 are determined and entered manually by the user (as opposed to being calculated by software). Thus, the PFM badges 1015 of interface 1000, which indicate values calculated by software, are not included in interface 1700. In some examples, when using the Standard technique, the values entered into fields 1701-1704 may be determined by a surgeon, for example based on an analysis of first and second images of the first and second anatomical structure segments with the fixation apparatus attached thereto. Also, in some examples, when using the Standard technique, it may be required for the first and the second images to be orthogonal with respect to one another in order to allow the surgeon to calculate the values for fields 1701-1704. This differs from the PFM technique described above with reference to FIGS. 4-13, in which the first and second images of the first and second anatomical structure segments with the fixation apparatus attached thereto need not necessarily be orthogonal to one another.

It is also noted that, unlike interface 1000, interface 1700 includes controls 1711 and 1712 for selecting whether the reference ring is perpendicular/orthogonal or non-perpendicular/non-orthogonal with relative to the respective bone segment on which it is mounted. In the example of FIG. 17, control 1711 is selected to indicate that the reference ring is perpendicular. For cases in which control 1712 is selected, interface 1700 may be adjusted, for example, to allow provide fields that allow the user to indicate the tilt of the reference ring. Similar to interface 1000, interface 1700 also includes a graphical representation 1750 of the position and orientation of the reference ring and the respective anatomical structure segment. Graphical representation 1750 includes a representation 1531 of the proximal anatomical structure segment and a representation 1733 of the proximal (reference) ring. Graphical representation 1750 may be adjusted based on the values entered into fields 1701-1704. For example, a user may enter values into fields 1701-1704 and then select Save and Update button 1721, which may cause graphical representation 1750 to be adjusted based on the values entered into fields 1701-1704.

After entering the deformity parameters, configuration parameters, and mounting parameters for the Standard technique, the software may be capable of determining manipulations to the fixation apparatus for correction of the anatomical structure deformity, for example using techniques such as those described above with respect to operation 338 of FIG. 3. For example, in some cases, the software may determine angulations of the first and/or second anatomical structure segments such that their axes are brought into alignment. In some cases, the software may also determine positions of the first and/or second anatomical structure segments such that their fractured ends abut each other. The software may also, for example, use provided configuration information and/or treatment plan options to calculate strut adjustments and other manipulations to the fixation apparatus that may, for example, cause axes of the anatomical structure segments to be aligned and/or cause fractured ends of the anatomical structure segments to abut each other. For example, after entering the mounting parameters, treatment plan interfaces 1800-A of FIG. 18, 1800-B of FIG. 19, and 1800-C of FIG. 20 may be displayed, such as for entering treatment plan options, and generating, displaying, and modifying the treatment plan as well as one or more graphical representations of the position and orientation of the first and second anatomical structure segments and rings of the fixation apparatus throughout the course of treatment. For example, treatment plan interface 1800-A displays a graphical representation 1850 of the position and orientation of the first and the second anatomical structure segments and the rings of the fixation apparatus. Graphical representation 1850 includes a representation 1531 of the proximal anatomical structure segment, a representation 1733 of the proximal (reference) ring, a representation 1532 of the distal anatomical structure segment, and a representation 1834 of the distal ring. It is noted that interfaces 1800-A of FIG. 18, 1800-B of FIG. 19 and 1800-C of FIG. 20 include features that substantially correspond to those of interfaces 1100-A of FIG. 11, 1100-B of FIG. 12, and 1100-C of FIG. 13. These corresponding features are described in detail above with references to FIGS. 11-13 and are not repeated here.

Figure 21:
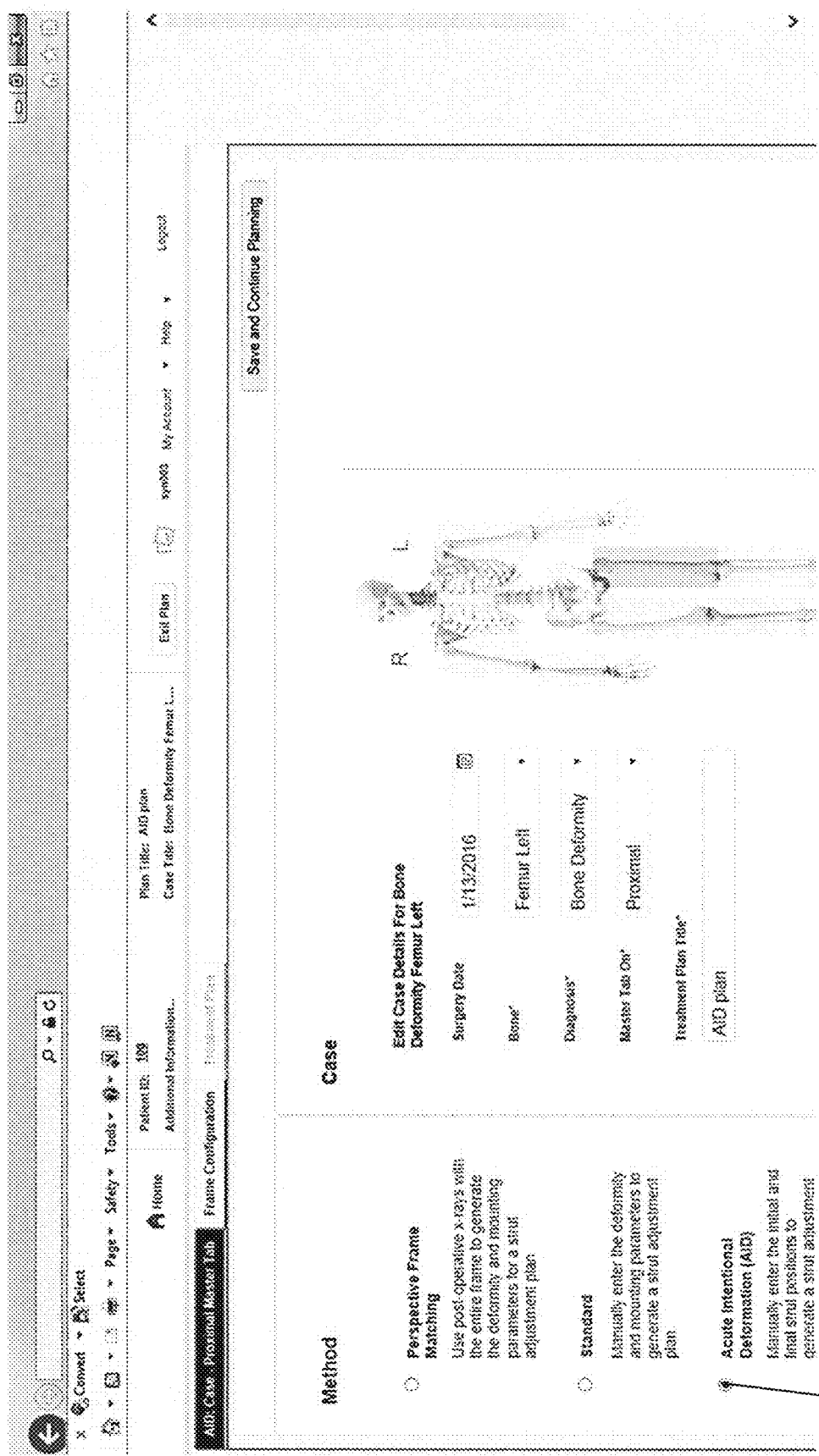
FIG. 21 is a screen shot of an example interface for selecting an Acute Intentional Deformation (AID) technique.

Thus, some examples of the Standard technique have been described in detail above with reference to FIGS. 14-20. In some examples, however, it may be advantageous for users to employ a different technique in the user manually enters initial and final strut positions into the software to generate a strut adjustment plan. This technique is referred to hereinafter as the Acute Intentional Deformation (AID) technique. In some examples, the AID technique may be used to correct deformities, such as soft tissue injuries, in which a patient's anatomical structures and/or the fixation apparatus may be temporarily flexibly manipulated such that final strut positions may be more easily determined and obtained. Deformity and frame parameters may not be required for use of the AID technique. In particular, referring now to FIG. 21, a treatment planning technique selection interface 400-C is shown. In the example of FIG. 21, the user has selected option 403 to use the AID technique, which will now be described in detail with reference to FIGS. 22-28.

Figure 22:
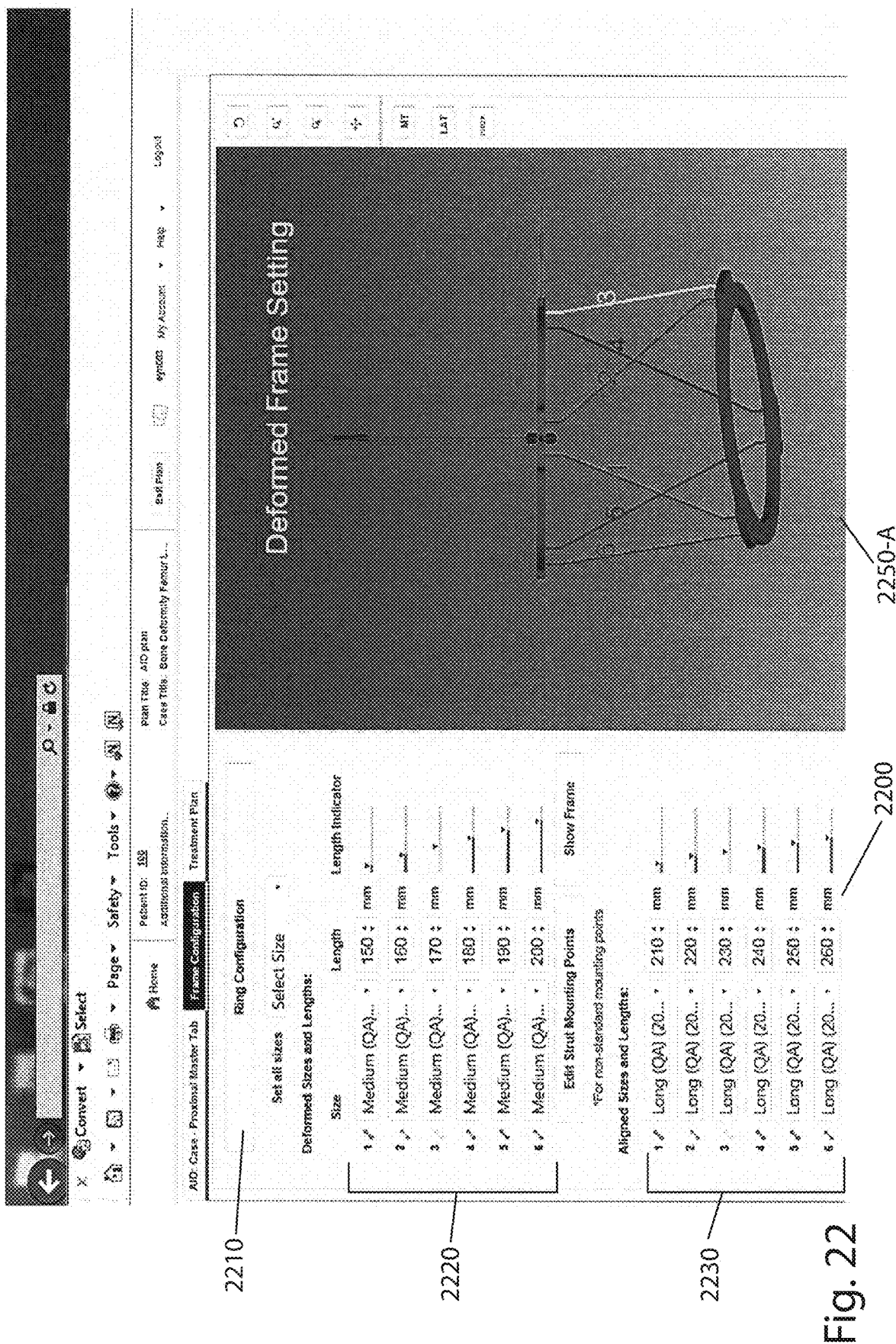
FIG. 22 is a screen shot of a first example configuration information entry interface for the AID technique.
Figure 23:
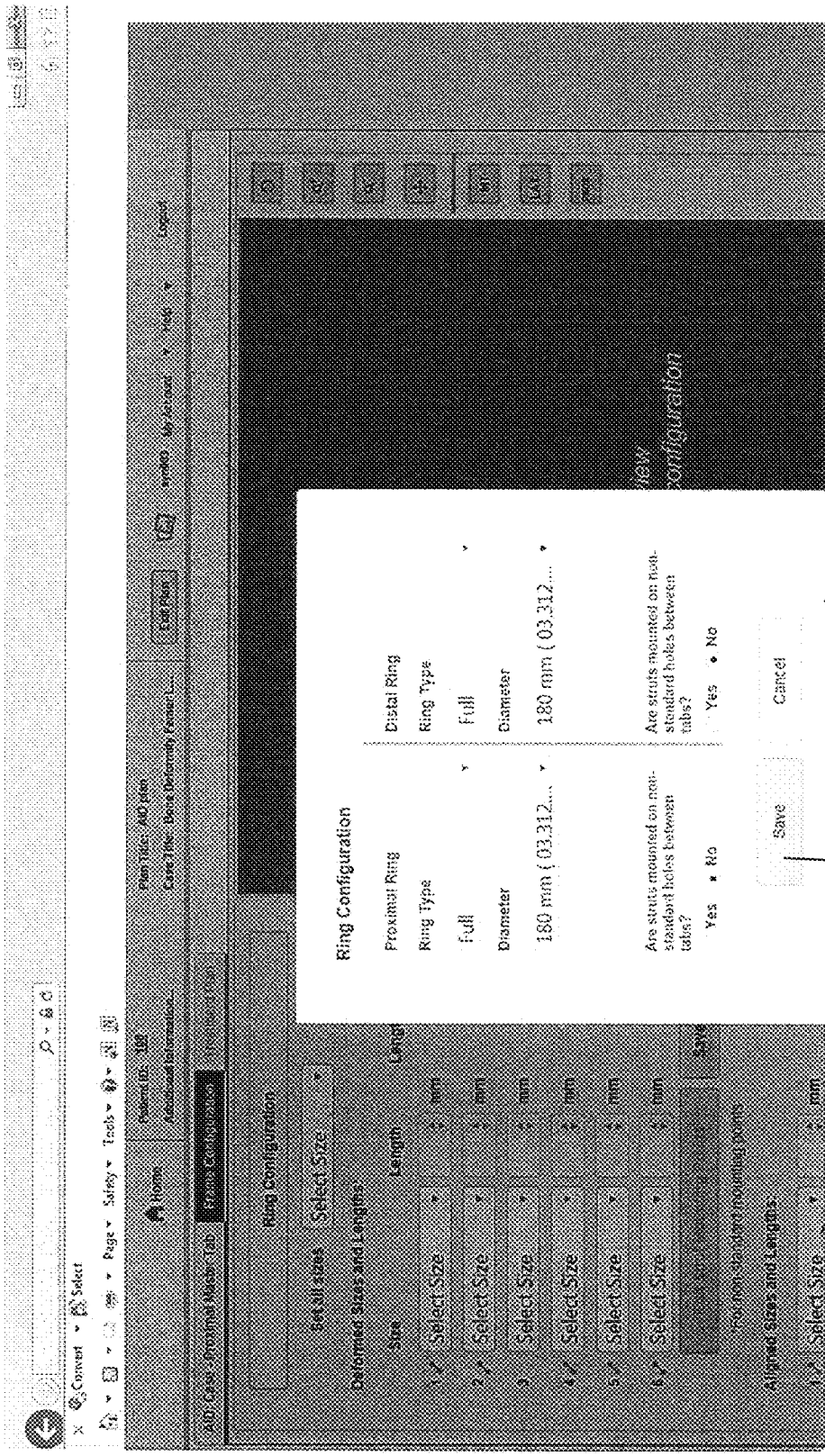
FIG. 23 is a screen shot of an example ring configuration information pane for the AID technique.

Referring now to FIG. 22, after selecting the AID technique, a configuration information interface 2200 is shown. Interface 2200 allows the user to enter configuration information associated with the fixation apparatus for the deformed (e.g., initial) setting and the aligned (e.g., final) setting. As shown, the user may select Ring Configuration button 2210 in order to enter ring configuration information. In particular, referring now to FIG. 23, selection of Ring Configuration button 2210 may cause a ring configuration information pane 2300 to be displayed overlaying interface 2200. As shown, ring configuration information pane 2300 may allow entry of information for the proximal and distal rings, such as ring type (e.g., full, foot plate, etc.), diameter or size, and whether struts are mounted on non-standard holes between tabs. Selection of Save button 2301 may cause the entered ring configuration information to be saved and cause the display to close pane 2300 and return to interface 2200.

Figure 24:
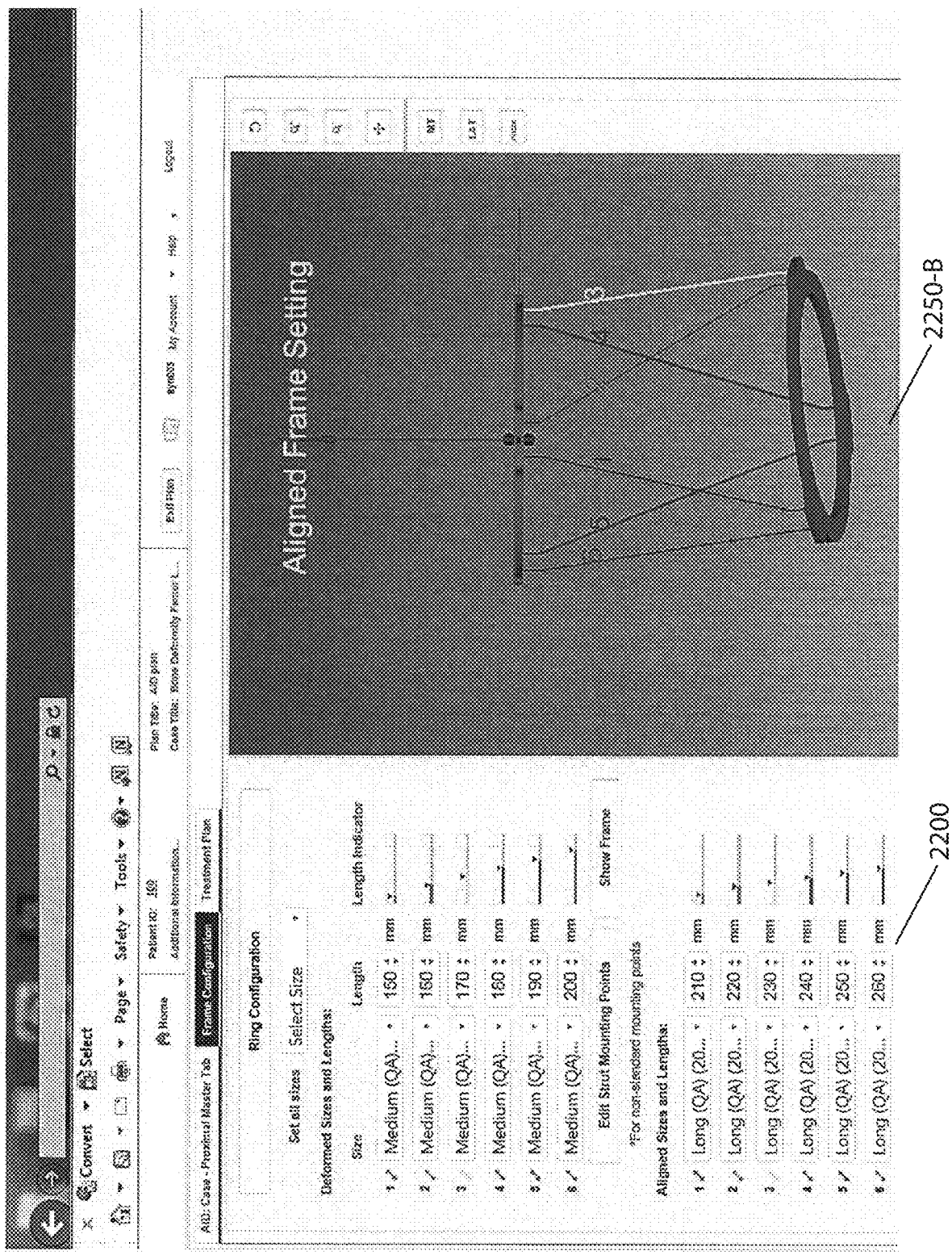
FIG. 24 is a screen shot of a second example configuration information entry interface for the AID technique.
Figure 25:
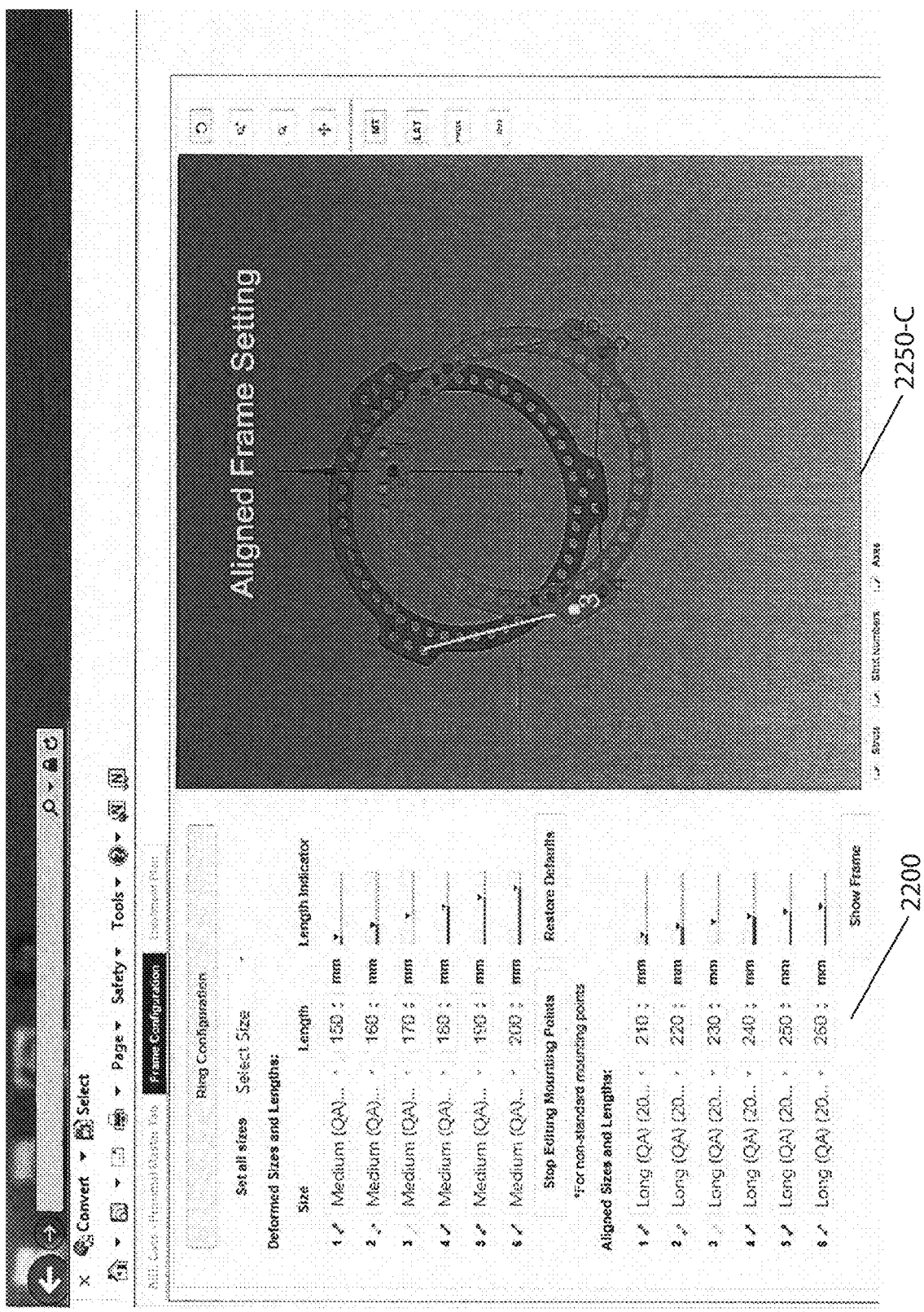
FIG. 25 is a screen shot of a third example configuration information entry interface for the AID technique.

Referring back to FIG. 22, it is seen that interface 2200 includes controls 2220 that allow strut size and length to be entered for the deformed (e.g., initial) setting. Additionally, interface 2200 includes controls 2230 that allow strut size and length to be entered for the aligned (e.g., final) setting. Furthermore, interface 2200 includes a graphical depiction 2250-A of the fixation apparatus for the deformed (e.g., initial) setting. Graphical depiction 2250-A is generated based, at least in part, on the entered configuration information for the deformed setting and includes color-coded struts for easy identification. Referring now to FIG. 24, another example of interface 2200 is shown that includes a graphical depiction 2250-B of the fixation apparatus for the aligned (e.g., final) setting. Graphical depiction 2250-B is generated based, at least in part, on the entered configuration information for the aligned setting and also includes color-coded struts for easy identification. Referring now to FIG. 25, yet another example of interface 2200 is shown that includes a graphical depiction 2250-C of the fixation apparatus for the aligned (e.g., final) setting viewed from a different (e.g., rotated) perspective than was shown in graphical depiction 2250-B of FIG. 24.

Figure 26:
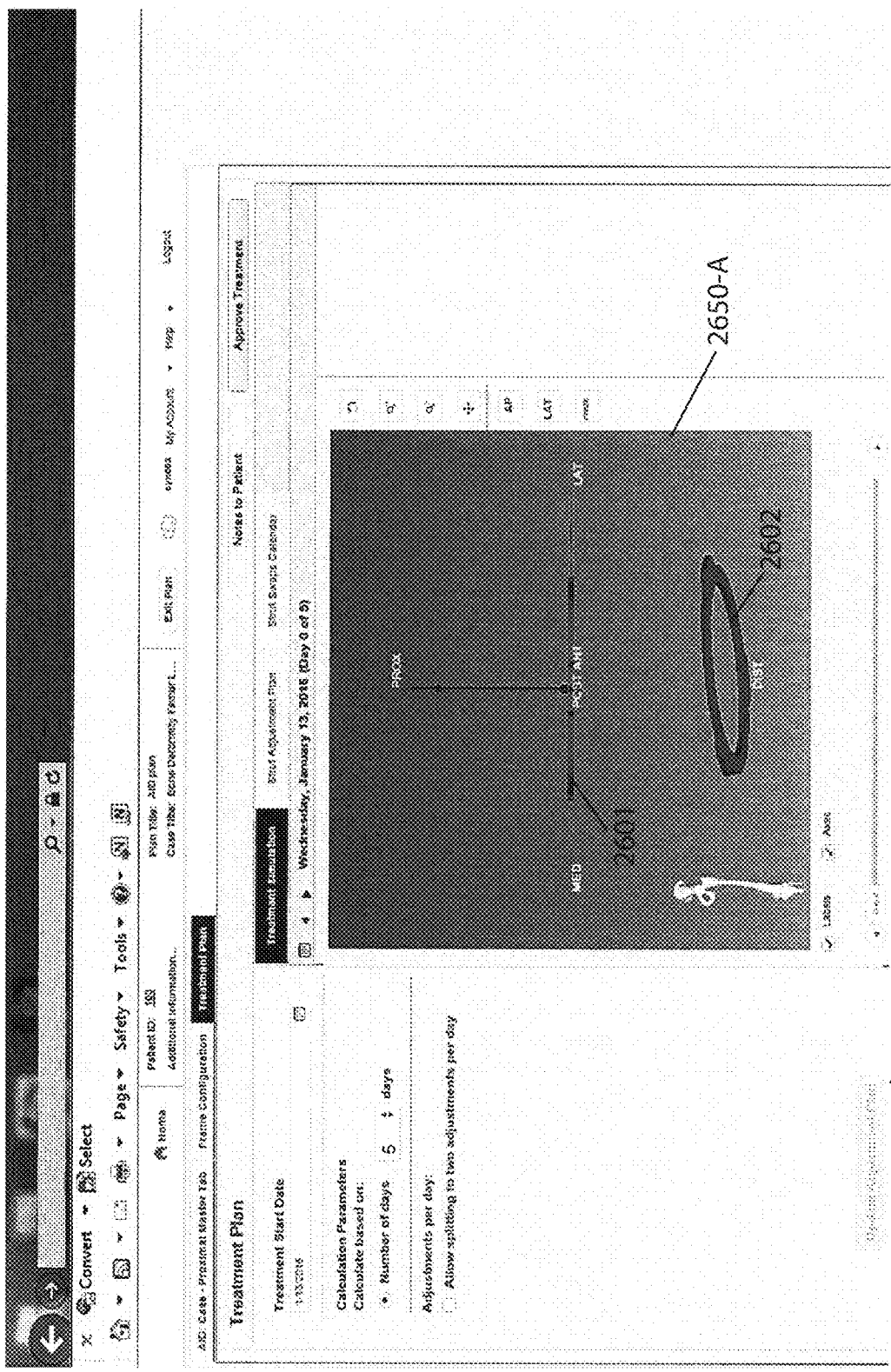
FIG. 26 is a screen shot of a first example treatment plan interface for the AID technique.
Figure 27:
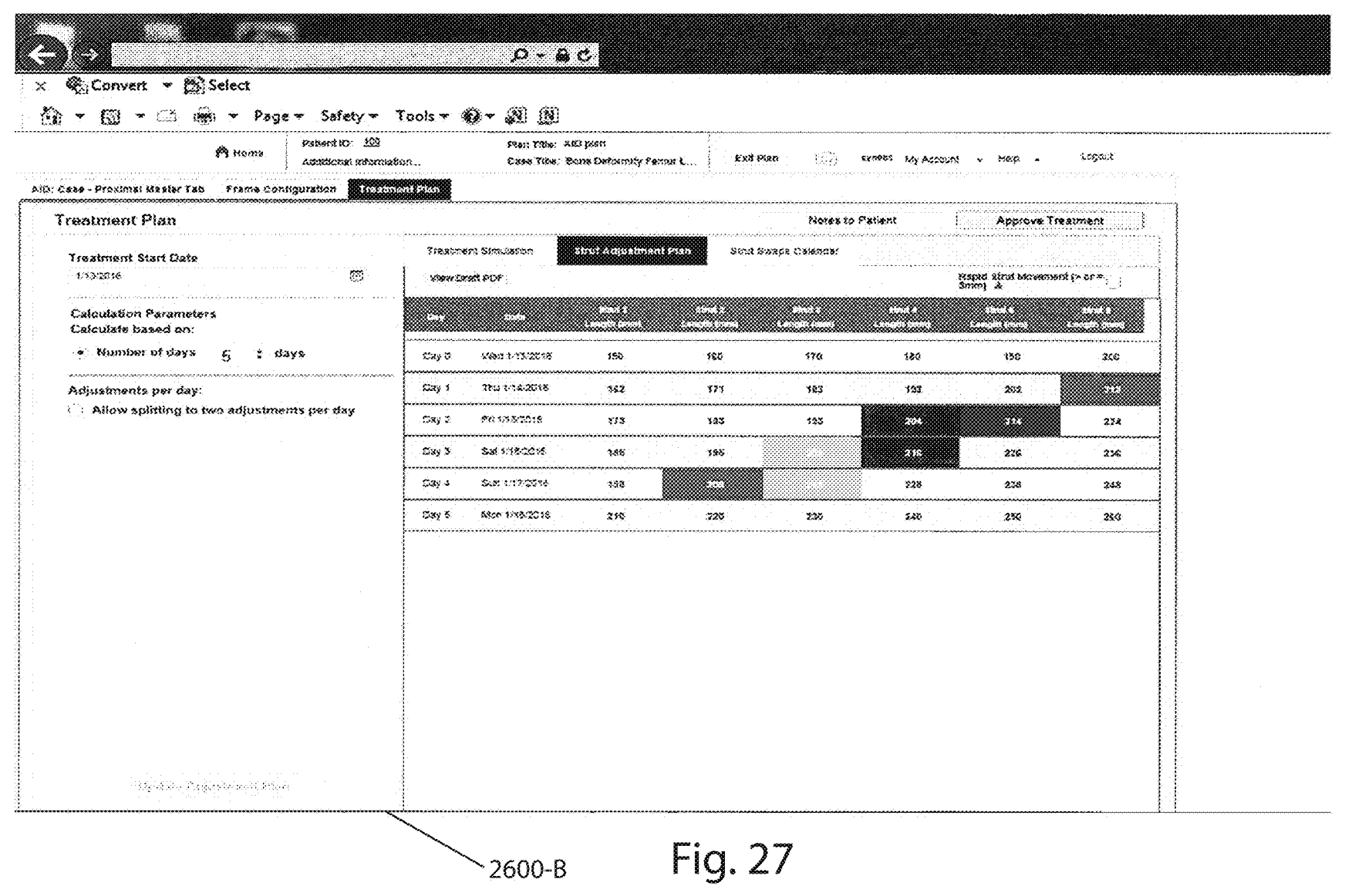
Figure 28:
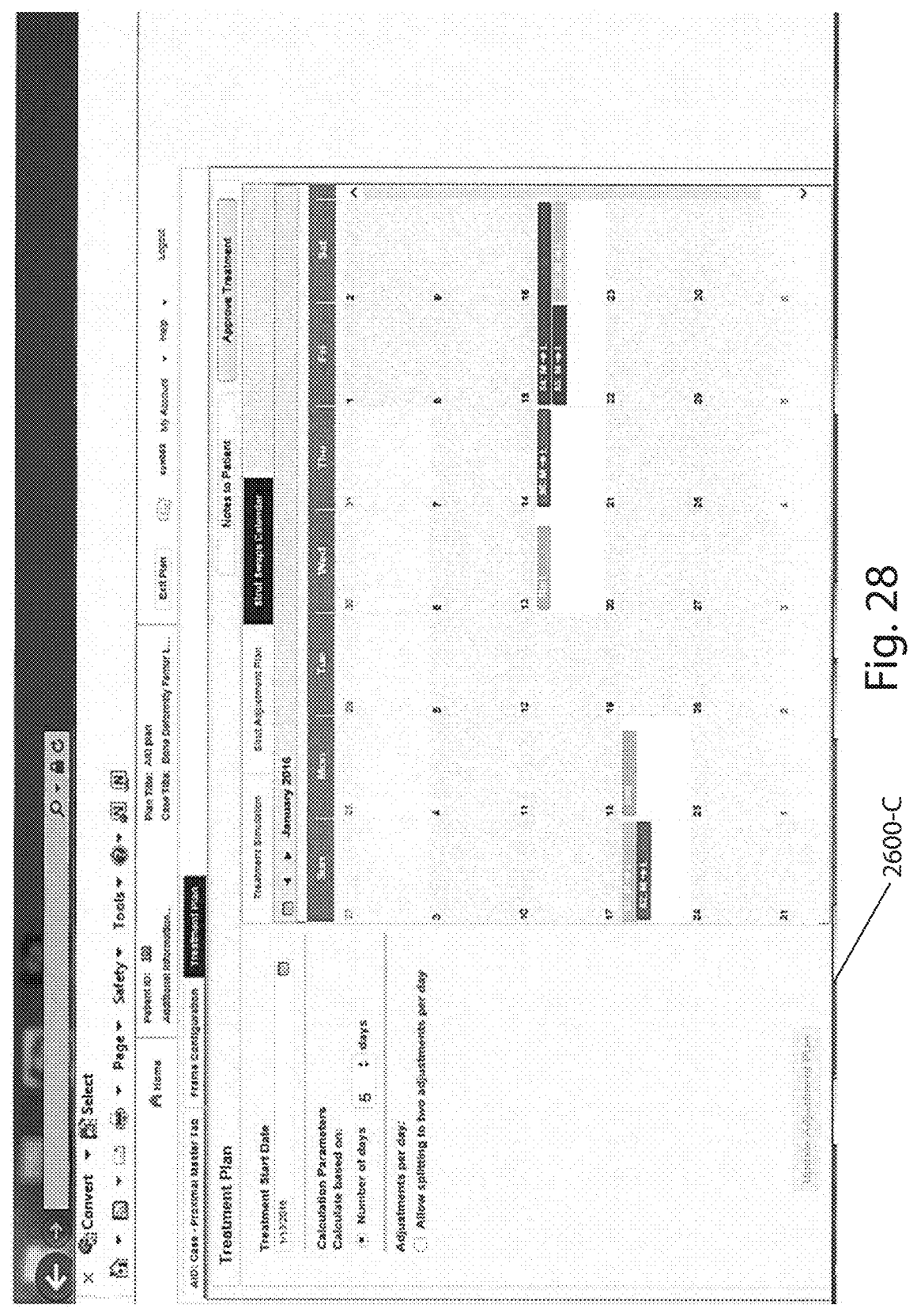

After entering the deformed and aligned configuration information, treatment plan interfaces 2600-A of FIG. 26, 2600-B of FIG. 27, and 2600-C of FIG. 28 may be displayed, such as for entering treatment plan options, and generating, displaying, and modifying the treatment plan as well as one or more graphical representations of the position and orientation of the rings of the fixation apparatus throughout the course of treatment. It is noted that interfaces 2600-A of FIG. 26, 2600-B of FIG. 27 and 2600-C of FIG. 28 include certain features that substantially correspond to those of interfaces 1100-A of FIG. 11, 1100-B of FIG. 12, and 1100-C of FIG. 13. These corresponding features are described in detail above with references to FIGS. 11-13 and are not repeated here. It is noted, however, there are some distinctions between interfaces 2600-A-C of FIGS. 26-28 and interfaces 1100-A-C of FIGS. 11-13. For example, it is noted that graphical representation 1150 of FIG. 11 includes indications of the positions and orientations of the rings of the fixation apparatus as well as the first and second anatomical structure segments. By contrast, graphical representation 2650-A of FIG. 26 includes indications of the positions and orientations of the rings of the fixation apparatus but not the first and second anatomical structure segments. Graphical representation 2650-A includes a representation 2601 of the proximal ring and a representation 2602 of the distal ring. This is because second image information is not provided for the AID technique. Additionally, for the same reasons, it is noted that interfaces 2600-A-C do not provide controls for certain treatment plan options that are directly related to anatomical structures, such as controls 1103 (axial movement first), 1104 (final distance between reference points), and 1106 (distraction at reference point).

Figure 29:
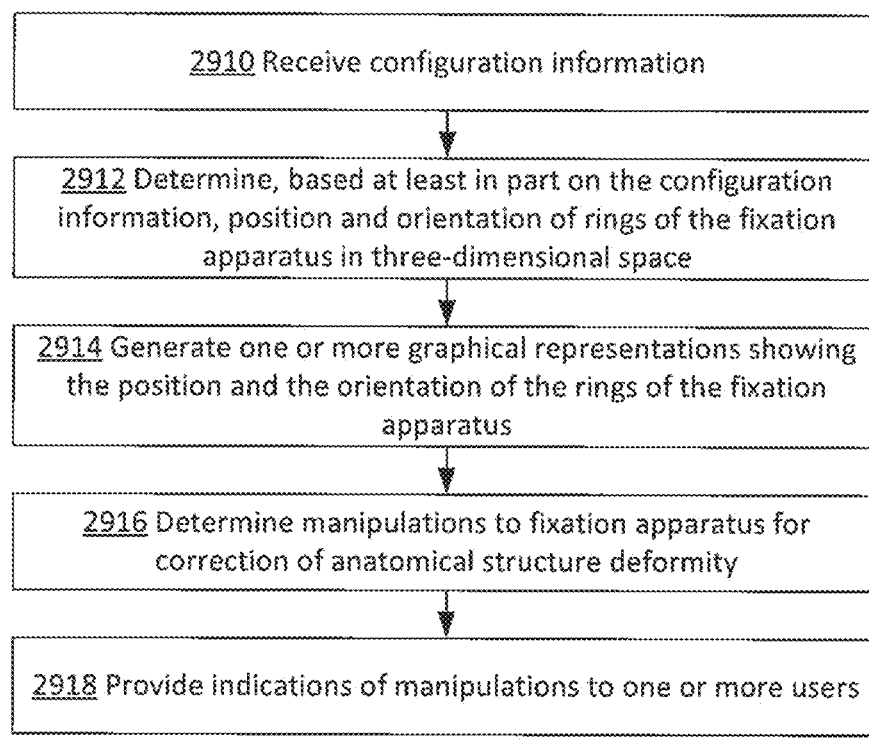
FIG. 29 is a flow diagram illustrating another example process for controlling manipulation of a fixation apparatus to correct an anatomical structure deformity.

Thus, based on the above descriptions, it is seen that a treatment plan including indications of periodic strut adjustments may be determined using the above described techniques, including the PFM technique, the Standard technique, and/or the AID technique. For example, in some cases, any or all of the above techniques may be used in an example process for controlling manipulation of a fixation apparatus including rings and struts to correct an anatomical structure deformity of first and second anatomical structure segments. In particular, referring now to FIG. 29, another example process for controlling manipulation of a fixation apparatus including rings and struts to correct an anatomical structure deformity of first and second anatomical structure segments will now be described in detail. The process of FIG. 29 may be performed by a computing system, for example including one or more computing devices. The process of FIG. 29 is initiated at operation 2910, at which configuration information associated with the fixation apparatus may be received, for example using one or more graphical user interfaces of a computing system. As described in detail above, the configuration information may include, for example, one or more geometric characteristics of rings, struts and/or other elements of the fixation apparatus. At operation 2912, the computing system may determine, based at least in part on the configuration information, a position and an orientation of the rings of the fixation apparatus in three-dimensional space. In particular, geometric characteristics of elements of the fixation apparatus may be used to determine the position and the orientation of the rings of the fixation apparatus in three-dimensional space. Specifically, in some cases, the position and orientation of the rings of the fixation apparatus in three-dimensional space may be calculated based on geometric characteristics such as strut length, ring diameter, and strut mounting locations. For example, in some cases, strut length and strut mounting location information may be used to determine distances between rings of the fixation apparatus at various different locations. At operation 2914, the computing system may generate one or more graphical representations showing the position and the orientation of the rings of the fixation apparatus in three-dimensional space.

At operation 2916, the computing system may determine, based at least in part on the configuration information, manipulations to the fixation apparatus for correction of the anatomical structure deformity. The manipulations may include adjustments to one or more struts. In some examples, the adjustments to the struts may be determined based on configuration information indicating current and/or initial geometric configurations for the struts and other elements of the fixation apparatus, such as the configuration information provided in the PFM technique, the configuration information provided in the Standard technique, and the deformed setting configuration information provided in the AID technique. In some cases, for the PFM technique and/or for the Standard technique, the software may determine manipulations to the fixation apparatus using techniques such as those described above with respect to operation 338 of FIG. 3B. For example, in some cases, the software may determine angulations of the first and/or second anatomical structure segments such that their axes are brought into alignment. In some cases, the software may also determine positions of the first and/or second anatomical structure segments such that their fractured ends abut each other. The software may also, for example, use provided configuration information and/or treatment plan options to calculate strut adjustments and other manipulations to the fixation apparatus that may, for example, cause axes of the anatomical structure segments to be aligned and/or cause fractured ends of the anatomical structure segments to abut each other.

For the AID technique, the software may be unaware of the positions and orientations of the first and the second anatomical structure segments. Instead, as described above for the AID technique, the software may receive configuration information for both the deformed (e.g., initial) and the aligned (e.g., final) settings of the fixation apparatus. The software may then use the deformed and aligned setting information in combination with the provided treatment plan options to determine manipulations to the fixation apparatus, for example that will cause the fixation apparatus to be transformed from the deformed setting to the aligned setting in accordance with the provided treatment plan options. At operation 2918, the computing system may provide, to one or more users, indications of the manipulations to the fixation apparatus. As described in detail above, the indications may be provided using interfaces such as depicted in FIGS. 11-13, 18-20, 26-28 and/or PDF format, printed to hard copy, etc.

In some examples, the one or more graphical representations generated at operation 2914 may comprise day-by-day graphical representations of the position and the orientation of the rings of the fixation apparatus in three-dimensional space throughout treatment for the anatomical structure deformity. Also, in some examples, in combination with the rings of the fixation apparatus, the one or more graphical representation may also show a position and an orientation of the first and the second anatomical structure segments in three-dimensional space. The one or more graphical representations may also include day-by-day graphical representations of the position and the orientation of the first and the second anatomical structure segments in three-dimensional space throughout treatment for the anatomical structure deformity. The one or more graphical representations may also show a position and an orientation of the struts of the fixation apparatus in three-dimensional space.

In some examples, the received configuration information may include lengths of struts in a deformed setting and lengths of struts in an aligned setting, for example as shown in FIGS. 22 and 24. Also, in some examples, the one or more graphical representations may show the position and orientation of the rings and the struts of the fixation apparatus in three-dimensional space in a deformed setting and in an aligned setting, for example as shown in FIGS. 22 and 24.

In some examples, deformity parameters may be received, for example as shown in FIG. 15, and the manipulations to the fixation apparatus may be determined based, at least in part, on the deformity parameters. In some examples, the received deformity parameters may include translation parameters and/or angulation parameters. Also, in some examples, mounting parameters may be received, for example as shown in FIG. 17, and the manipulations to the fixation apparatus may be determined based, at least in part, on the mounting parameters. In some examples, the received mounting parameters may include offsets associated with a reference ring and a reference point.

Figure 30:
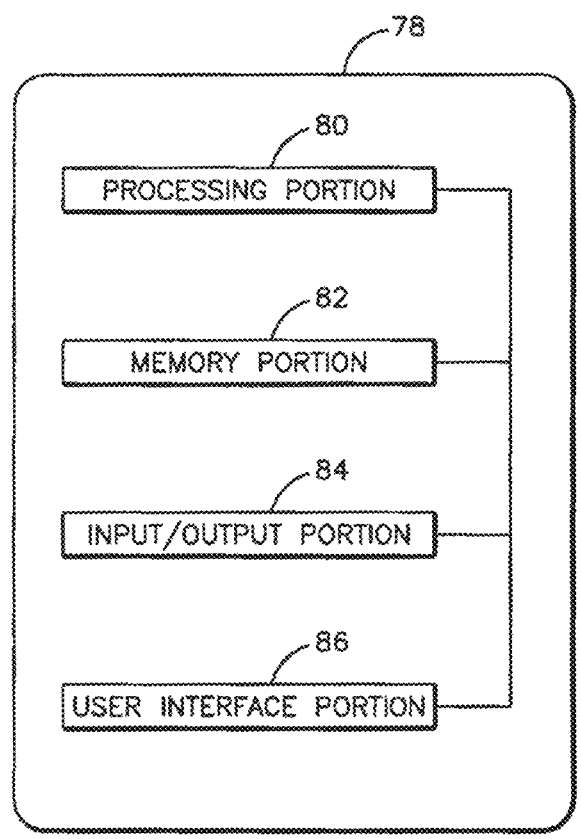
FIG. 30 is a block diagram of an example computing device for use in accordance with the present disclosure.

Referring to FIG. 30, a suitable computing device such as example computing device 78 can be configured to perform any or all of the fixation apparatus control and manipulation techniques set forth above. It will be understood that the computing device 78 can include any appropriate device, examples of which include a desktop computing device, a server computing device, or a portable computing device, such as a laptop, tablet, or smart phone.

In an example configuration, the computing device 78 includes a processing portion 80, a memory portion 82, an input/output portion 84, and a user interface (UI) portion 86. It is emphasized that the block diagram depiction of the computing device 78 is exemplary and not intended to imply a specific implementation and/or configuration. The processing portion 80, memory portion 82, input/output portion 84, and user interface portion 86 can be coupled together to allow communications therebetween. As should be appreciated, any of the above components may be distributed across one or more separate devices and/or locations.

In various embodiments, the input/output portion 84 includes a receiver of the computing device 78, a transmitter of the computing device 78, or a combination thereof. The input/output portion 84 is capable of receiving and/or providing information pertaining to communicate a network such as, for example, the Internet. As should be appreciated, transmit and receive functionality may also be provided by one or more devices external to the computing device 78.

The processing portion 80 may include one or more processors. Depending upon the exact configuration and type of processor, the memory portion 82 can be volatile (such as some types of RAM), non-volatile (such as ROM, flash memory, etc.), or a combination thereof. The computing device 78 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information and which can be accessed by the computing device 78.

The computing device 78 also can contain the user interface portion 86 allowing a user to communicate with the computing device 78. The user interface 86 can include inputs that provide the ability to control the computing device 78, via, for example, buttons, soft keys, a mouse, voice actuated controls, a touch screen, movement of the computing device 78, visual cues (e.g., moving a hand in front of a camera on the computing device 78), or the like. The user interface portion 86 can provide outputs, including visual information (e.g., via a display), audio information (e.g., via speaker), mechanically (e.g., via a vibrating mechanism), or a combination thereof. In various configurations, the user interface portion 86 can include a display, one or more graphical user interfaces, a touch screen, a keyboard, a mouse, an accelerometer, a motion detector, a speaker, a microphone, a camera, a tilt sensor, or any combination thereof. Thus, a computing system including, for example, one or more computing devices 78 can include a processor, a display coupled to the processor, and a memory in communication with the processor, one or more graphical user interfaces, and various other components. The memory can have stored therein instructions that, upon execution by the processor, cause the computer system to perform operations, such as the operations described above. As used herein, the term computing system can refer to a system that includes one or more computing devices 78. For instance, the computing system can include one or more server computing devices that communicate with one or more client computing devices.

While example embodiments of devices for executing the disclosed techniques are described herein, the underlying concepts can be applied to any computing device, processor, or system capable of communicating and presenting information as described herein. The various techniques described herein can be implemented in connection with hardware or software or, where appropriate, with a combination of both. Thus, the methods and apparatuses described herein can be implemented, or certain aspects or portions thereof, can take the form of program code (i.e., instructions) embodied in tangible non-transitory storage media, such as floppy diskettes, CD-ROMs, hard drives, or any other machine-readable storage medium (computer-readable storage medium), wherein, when the program code is loaded into and executed by a machine, such as a computer, the machine becomes an apparatus for performing the techniques described herein. In the case of program code execution on programmable computers, the computing device will generally include a processor, a storage medium readable by the processor (including volatile and non-volatile memory and/or storage elements), at least one input device, and at least one output device, for instance a display. The display can be configured to display visual information. The program(s) can be implemented in assembly or machine language, if desired. The language can be a compiled or interpreted language, and combined with hardware implementations.

It should be appreciated that the orthopedic fixation with imagery analysis techniques described herein provide not only for the use of non-orthogonal images, but also allow the use of overlapping images, images captured using different imaging techniques, images captured in different settings, and the like, thereby presenting a surgeon with greater flexibility when compared with existing fixation and imagery techniques.

The techniques described herein also can be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein can invariably be a combination of hardware and software.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

What is claimed:

1. A computer-implemented method for controlling manipulation of a fixation apparatus including rings and struts to correct an anatomical structure deformity of first and second anatomical structure segments comprising:
   receiving, using one or more graphical user interfaces of a computing system, configuration information associated with the fixation apparatus, the configuration information comprising one or more geometric characteristics of the rings and the struts of the fixation apparatus;
   determining, by the computing system, based at least in part on the configuration information, a position and an orientation of the rings of the fixation apparatus in three-dimensional space;
   generating, by the computing system, one or more graphical representations showing the position and the orientation of the rings of the fixation apparatus;
   determining, by the computing system, based at least in part on the configuration information, manipulations to the fixation apparatus for correction of the anatomical structure deformity, the manipulations comprising strut length changes and a strut size change; and
   providing, by the computing system, to one or more users, an interface that displays a plurality of areas each corresponding to a respective day of a plurality of days, wherein the interface displays one or more indications of a range of days within the plurality of days on which a strut swap is performable, wherein the one or more indications are included in a group of areas within the plurality of areas corresponding to the range of days, and wherein the strut swap corresponds to the strut size change.

2. The computer-implemented method of claim 1, wherein the one or more graphical representations comprise day-by-day graphical representations of the position and the orientation of the rings of the fixation apparatus throughout treatment for the anatomical structure deformity.

3. The computer-implemented method of claim 1, wherein the one or more graphical representations further show a position and an orientation of the first and the second anatomical structure segments.

4. The computer-implemented method of claim 3, wherein the one or more graphical representations comprise day-by-day graphical representations of the position and the orientation of the first and the second anatomical structure segments throughout treatment for the anatomical structure deformity.

5. The computer-implemented method of claim 1, wherein the configuration information comprises lengths of struts in a deformed setting and lengths of struts in an aligned setting.

6. The computer-implemented method of claim 5, wherein the one or more graphical representations show the position and the orientation of the rings and a position and an orientation of the struts in the deformed setting and in the aligned setting.

7. The computer-implemented method of claim 1, further comprising receiving deformity parameters comprising at least one of translation parameters or angulation parameters, wherein the manipulations to the fixation apparatus are determined based, at least in part, on the deformity parameters.

8. The computer-implemented method of claim 1, further comprising receiving mounting parameters comprising offsets associated with a reference ring and a reference point, wherein the manipulations to the fixation apparatus are determined based, at least in part, on the mounting parameters.

9. One or more non-transitory computer-readable storage media having stored thereon instructions that, upon execution by one or more computing devices, cause the one or more computing devices to perform operations for controlling manipulation of a fixation apparatus including rings and struts to correct an anatomical structure deformity of first and second anatomical structure segments, the operations comprising:
   receiving, using one or more graphical user interfaces of a computing system, configuration information associated with the fixation apparatus, the configuration information comprising one or more geometric characteristics of the rings and the struts of the fixation apparatus;
   determining, by the computing system, based at least in part on the configuration information, a position and an orientation of the rings of the fixation apparatus in three-dimensional space;
   generating, by the computing system, one or more graphical representations showing the position and the orientation of the rings of the fixation apparatus;
   determining, by the computing system, based at least in part on the configuration information, manipulations to the fixation apparatus for correction of the anatomical structure deformity, the manipulations comprising strut length changes and strut size change; and
   providing, by the computing system, to one or more users, an interface that displays a plurality of areas each corresponding to a respective day of a plurality of days, wherein the interface displays one or more indications of a range of days within the plurality of days on which a strut swap is performable, wherein the one or more indications are included in a group of areas within the plurality of areas corresponding to the range of days, and wherein the strut swap corresponds to the strut size change.

10. The one or more non-transitory computer-readable storage media of claim 9, wherein the one or more graphical representations comprise day-by-day graphical representations of the position and the orientation of the rings of the fixation apparatus throughout treatment for the anatomical structure deformity.

11. The one or more non-transitory computer-readable storage media of claim 9, wherein the one or more graphical representations further show a position and an orientation of the first and the second anatomical structure segments.

12. The one or more non-transitory computer-readable storage media of claim 11, wherein the one or more graphical representations comprise day-by-day graphical representations of the position and the orientation of the first and the second anatomical structure segments throughout treatment for the anatomical structure deformity.

13. The one or more non-transitory computer-readable storage media of claim 9, wherein the configuration information comprises lengths of struts in a deformed setting and lengths of struts in an aligned setting.

14. The one or more non-transitory computer-readable storage media of claim 13, wherein the one or more graphical representations show the position and the orientation of the rings and a position and an orientation of the struts in the deformed setting and in the aligned setting.

15. The one or more non-transitory computer-readable storage media of claim 9, wherein the operations further comprise receiving deformity parameters comprising at least one of translation parameters or angulation parameters, wherein the manipulations to the fixation apparatus are determined based, at least in part, on the deformity parameters.

16. The one or more non-transitory computer-readable storage media of claim 9, wherein the operations further comprise receiving mounting parameters comprising offsets associated with a reference ring and a reference point, wherein the manipulations to the fixation apparatus are determined based, at least in part, on the mounting parameters.

17. A computing system for controlling manipulation of a fixation apparatus including rings and struts to correct an anatomical structure deformity of first and second anatomical structure segments comprising:

one or more processors; and
one or more memories having stored therein instructions that, upon execution by the one or more processors, cause the computing system to perform operations comprising:
receiving, using one or more graphical user interfaces of the computing system, configuration information associated with the fixation apparatus, the configuration information comprising one or more geometric characteristics of rings and struts of the fixation apparatus;
determining, by the computing system, based at least in part on the configuration information, a position and an orientation of the rings of the fixation apparatus in three-dimensional space;
generating, by the computing system, one or more graphical representations showing the position and the orientation of the rings of the fixation apparatus;
determining, by the computing system, based at least in part on the configuration information, manipulations to the fixation apparatus for correction of the anatomical structure deformity, the manipulations comprising strut length changes and strut size change; and
providing, by the computing system, to one or more users, an interface that displays a plurality of areas each corresponding to a respective day of a plurality of days, wherein the interface displays one or more indications of a range of days within the plurality of days on which a strut swap is performable, wherein the one or more indications are included in a group of areas within the plurality of areas corresponding to the range of days, and wherein the strut swaps correspond swap corresponds to the strut size change.

18. The computing system of claim 17, wherein the one or more graphical representations comprise day-by-day graphical representations of the position and the orientation of the rings of the fixation apparatus throughout treatment for the anatomical structure deformity.

19. The computing system of claim 17, wherein the one or more graphical representations further show a position and an orientation of the first and the second anatomical structure segments.

20. The computing system of claim 19, wherein the one or more graphical representations comprise day-by-day graphical representations of the position and the orientation of the first and the second anatomical structure segments throughout treatment for the anatomical structure deformity.

* * * * *